United States Patent
Forman et al.

(10) Patent No.: US 11,918,606 B2
(45) Date of Patent: Mar. 5, 2024

(54) CD123-SPECIFIC CHIMERIC ANTIGEN RECEPTOR REDIRECTED T CELLS AND METHODS OF THEIR USE

(71) Applicant: City of Hope, Duarte, CA (US)

(72) Inventors: Stephen J. Forman, Duarte, CA (US); Armen Mardiros, Duarte, CA (US); Christine E. Brown, Duarte, CA (US)

(73) Assignee: City of Hope, Duarte, CA (US)

( * ) Notice: Subject to any disclaimer, the term of this patent is extended or adjusted under 35 U.S.C. 154(b) by 982 days.

(21) Appl. No.: 16/859,590

(22) Filed: Apr. 27, 2020

(65) Prior Publication Data

US 2020/0254023 A1 Aug. 13, 2020

Related U.S. Application Data

(60) Division of application No. 15/601,793, filed on May 22, 2017, now Pat. No. 10,660,916, which is a continuation of application No. 13/844,048, filed on Mar. 15, 2013, now Pat. No. 9,657,105.

(51) Int. Cl.
| | |
|---|---|
| A61K 35/17 | (2015.01) |
| C07K 14/725 | (2006.01) |
| C07K 16/28 | (2006.01) |
| A61K 39/00 | (2006.01) |

(52) U.S. Cl.
CPC .......... *A61K 35/17* (2013.01); *C07K 14/7051* (2013.01); *C07K 16/2866* (2013.01); *A61K 2039/505* (2013.01); *C07K 2317/622* (2013.01); *C07K 2319/00* (2013.01)

(58) Field of Classification Search
None
See application file for complete search history.

(56) References Cited

U.S. PATENT DOCUMENTS

| | | |
|---|---|---|
| 7,070,995 B2 | 7/2006 | Jensen |
| 9,657,105 B2 | 5/2017 | Forman et al. |
| 9,914,909 B2 | 3/2018 | Brown et al. |
| 10,660,916 B2 | 5/2020 | Forman et al. |
| 10,676,717 B2 | 6/2020 | Brown et al. |
| 2002/0102264 A1 | 8/2002 | Cheung |
| 2009/0252742 A1 | 10/2009 | Bergstein |
| 2012/0148552 A1 | 6/2012 | Jensen |
| 2012/0301447 A1 | 11/2012 | Jensen |
| 2013/0004514 A1 | 1/2013 | Zahn |
| 2013/0287798 A1 | 10/2013 | Cheung |
| 2013/0295116 A1 | 11/2013 | Zahn et al. |
| 2014/0271582 A1 | 9/2014 | Forman et al. |
| 2014/0271635 A1 | 9/2014 | Brogdon et al. |
| 2014/0322212 A1 | 10/2014 | Brogdon |
| 2015/0024482 A1 | 1/2015 | Frigault et al. |
| 2020/0040096 A1 | 2/2020 | Forman et al. |

FOREIGN PATENT DOCUMENTS

| | | |
|---|---|---|
| CN | 101952454 | 1/2011 |
| CN | 103492406 | 1/2014 |
| CN | 105392887 | 3/2016 |
| EA | 009873 | 4/2008 |
| JP | 2011-514150 | 5/2011 |
| JP | 2012-501180 | 1/2012 |
| JP | 2016-514457 | 5/2016 |
| WO | WO 2005/076843 | 8/2005 |
| WO | WO 2009/100309 | 8/2009 |
| WO | WO 2010/025177 | 3/2010 |
| WO | WO 2010/085682 | 7/2010 |
| WO | WO 2011/056894 | 5/2011 |
| WO | WO 2012/031744 | 3/2012 |
| WO | WO 2012/168199 | 12/2012 |
| WO | WO 2012/079000 | 8/2013 |
| WO | WO 2013/123061 | 8/2013 |
| WO | WO 2014/144622 | 9/2014 |

OTHER PUBLICATIONS

Aigner, M., et al., "T Lymphocytes Can Be Effectively Recruited for Ex Vivo and In Vivo Lysis of AML Blasts By a Novel CD33/CD3-Bispecific BITE Antibody Construct," Leukemia 27:1107-1115 (2013).
Appay, V., et al., "CD8+ T Cell Efficacy in Vaccination and Disease," Nat. Med. 14(6):623-628 (2008).
*Armen Mardiros v. City of Hope*, "Summons in a Civil Action," Case 2:19-cv-02196-CAS-MAA, Mar. 25, 2019, 83 pages.
Bhatia, R., et al., "Abnormal Function of the Bone Marrow Microenvironment in Chronic Myelogenous Leukemia:Role of Malignant Stromal Macrophages," Blood 85:3636-3645 (1995).
Brentjens, R. J., et al., "Eradication of Systemic B-Cell Tumors by Genetically Targeted Human T Lymphocytes Co-Stimulated by CD80 and Interleukin-15," Nat. Med. 9(3):279-286 (2003).

(Continued)

*Primary Examiner* — Michael D Pak
(74) *Attorney, Agent, or Firm* — Fish & Richardson P.C.

(57) ABSTRACT

A family of chimeric antigen receptors (CARs) containing a CD123 specific scFv was developed to target different epitopes on CD123. In some embodiments, such a CD123 chimeric antigen receptor (CD123CAR) gene includes an anti-CD123 scFv region fused in frame to a modified IgG4 hinge region comprising an S228P substitution, an L235E substitution, and optionally an N297Q substitution; a costimulatory signaling domain; and a T cell receptor (TCR) zeta chain signaling domain. When expressed in healthy donor T cells (CD4/CD8), the CD123CARs redirect T cell specificity and mediated potent effector activity against CD123+ cell lines as well as primary AML patient samples. Further, T cells obtained from patients with active AML can be modified to express CD123CAR genes and are able to lyse autologous AML blasts in vitro. Finally, a single dose of $5.0 \times 10^6$ CAR123 T cells results in significantly delayed leukemic progression in mice. These results suggest that CD123CAR-transduced T cells may be used as an immunotherapy for the treatment of high risk AML.

20 Claims, 26 Drawing Sheets

Specification includes a Sequence Listing.

(56) References Cited

OTHER PUBLICATIONS

Brentjens, R. J., et al., "Safety and Persistence of Adoptively Transferred Autologous CD19- Targeted T Cells in Patients with Relapsed or Chemotherapy Refractory B-Cell Leukemias, " Blood 118:4817-4828 (2011).

Brown, C. E., et al., "Recognition and Killing of Brain Tumor Stem-Like Initiating Cells by CD8+ Cytolytic T Cells," Cancer Res. 69:8886-8893 (2009).

Brown, E. J., et al., "Integrin-Associated Protein (CD47) and Its Ligands," Trends Cell Biol. 11(3):130-135 (2001).

Chinese First Office Action in Chinese Application No. 201480024929. 6, dated Feb. 1, 2018, 16 pages (with English Translation).

Cooper, L. J. N., et al., "T-Cell Clones can be Rendered Specific for CD19: Toward the Selective Augmentation of the Graft-Versus-B-Lineage Leukemia Effect," Blood 101:1637-1644 (2003).

Dohner, H., et al., "Diagnosis and Management of Acute Myeloid Leukemia in Adults: Recommendations from an International Expert Panel, on Behalf of the European LeukemiaNet," Blood 115:453-474 (2010).

Du, X., et al., "New Immunotoxins Targeting CD123, a Stem Cell Antigen on Acute Myeloid Leukemia Cells," J. Immunother. 30:607-613 (2007).

Dutour, A., et al., "In Vitro and In Vivo Antitumor Effect of Anti-CD33 Chimeric Receptor- Expressing EBV-CTL Against CD33+ Acute Myeloid Leukemia," Adv. Hematol. 2012:683065 (2012). EFS.

Eaves, C. J., et al., "Acute Myeloid Leukemia and the Wnt Pathway," New Eng. J. Med. 362(24):2326-2327 (2010).

European Application No. 14765454.5, Extended European Search Report, dated Dec. 6, 2016, 11 pages.

European Application No. 14877876.4, Extended European Search Report, dated Jul. 28, 2017, 10 pages.

European Office Action in European Application No. 14877876.4, dated Jul. 13, 2018, 7 pages.

European Search Report in European Application No. 19189084.7, dated Feb. 14, 2020, 6 pages.

European Search Report in European Application No. 19204610.0, dated Feb. 24, 2020, 13 pages.

Gattinoni, L., et al., "A Human Memory T-Cell Subset with Stem Cell-Like Properties," Nat. Med. 17(10):1290-1297 (2011).

Golden-Mason, L., et al., "Negative Immune Regulator Tim-3 Is Overexpressed on T Cells in Hepatitis C Virus Infection and Its Blockade Rescues Dysfunctional CD4+ and CD8+ T Cells," J. Virol. 83(18):9122-9130 (2009).

Hernandez-Caselles, T., et al., "A Study of CD33 (SIGLEC-3) Antigen Expression and Function on Activated Human land NK Cells: Two Isoforms of CD33 are Generated by Alternative Splicing," J. Leukocyte Biol. 79:46-58 (2006).

Hombach et al., "Adoptive immunotherapy with genetically engineered T cells: modification of the IgG1 Fc 'spacer' domain in the extracellular moiety of chimeric antigen receptors avoids 'off-target' activation and unintended initiation of an innate immune response," Gene therapy, Oct. 2010, 17(10):1206-1213.

Hudecek, M., et al., "The B-Cell Tumor-Associated Antigen ROR1 can be Targeted with T Cells Modified to Express a ROR1-Specific Chimeric Antigen Receptor," Blood 116:4532-4541(2010).

Hudecek et al., "The Non-Signaling Extracellular Spacer Domain of CD19-Specific Chimeric Antigen Receptors is Decisive for in vivo Anti-Tumor Activity", Meeting Abstract No. 951, Blood 2012, 120:951 (2012), 3 pages.

Hudecek et al., "Receptor Affinity and Extracellular Domain Modifications Affect Tumor Recognition by ROR1-Specific Chimeric Receptor T Cells," Clinical Cancer Research, 19(12):3153-3164, Apr. 19, 2013.

International Application No. PCT/US14/29109, Notification of Transmittal of the International Search Report and the Written Opinion of the International Searching Authority, dated Apr. 17, 2015, 16 pages.

International Application No. PCT/US2014/028961, Notification of Transmittal of the International Search Report and the Written Opinion of the International Searching Authority, dated Jul. 28, 2014, 9 pages.

Japanese Notice of Reasons for Rejection in Japanese Application No. 2016-502984, dated Feb. 13, 2018 14 pages (with English Translation).

Jena, B., et al., "Redirecting T-Cell Specificity by Introducing a Tumor-Specific Chimeric Antigen Receptor," Blood 116:1035-1044(2010).

Jensen, "Abstract IA22: Advanced T cell engineering for cancer immunotherapy," Cancer Research (2013) vol. 73, No. 1 Supplement, p.IA22 (Abstract IA22) (Published Jan. 2013) [online], Internet <URL: http://cancerres.aacrjournals.org/content/73/1_Supplement/IA22>, 5 pages.

Jensen, M. C., et al., "Human T Lymphocyte Genetic Modification with Naked DNA," Mol. Ther. 1(1):49-55 (2000).

Jin, H.T., et al., "Cooperation of Tim-3 and PD-1 in CD8 T-Cell Exhaustion During Chronic Viral Infection," PNAS 107 (33):14733-14738 (2010).

Jin, L., et al., "Monoclonal Antibody-Mediated Targeting of CD123, IL-3 Receptor Alpha Chain, Eliminates Human Acute Myeloid Leukemic Stem Cells," Cell Stem Cell 5:31-42 (2009).

Jonnalagadda et al., "Chimeric antigen receptors (CARs) incorporating mutations in the IgG4 Fc spacer region to eliminate Fc receptor recognition results in improved Car T cell persistence and anti-tumor efficacy", Journal for Immuno Therapy of Cancer 2013, 1(Suppl 1):P18, Nov. 7, 2013.

Jonnalagadda et al., "Chimeric Antigen Receptors With Mutated IgG4 Fc Spacer Avoid Fc Receptor Binding and Improve T Cell Persistence and Antitumor Efficacy", Molecular Therapy, vol. 23, No. 4, Apr. 2015, pp. 757-768.

Jordan, C.T., et al., "The Interleukin-3 Receptor Alpha Chain is a Unique Marker for Human Acute Myelogenous Leukemia Stem Cells," Leukemia 14:1777-1784 (2000).

Kalos M. et al. "T Cells with Chimeric Antigen Receptors Have Potent Antitumor Effects and Can Establish Memory in Patients with Advanced Leukemia," Sci. Transl. Med. 3:95ra73 (2011).

Kershaw et al., "Gene-engineered T cells for cancer therapy," Nature Reviews Cancer, Aug. 1, 2013, 13(8):525-541.

Kikushige, Y., et al., "TIM-3 Is a Promising Target to Selectively Kill Acute Myeloid Leukemia Stem Cells," Cell Stem Cell 7:708-717 (2010).

Kochenderfer, J. N., et al., "B-Cell Depletion and Remissions of Malignancy Along with Cytokine-Associated Toxicity in a Clinical Trial of Anti-CD 19 Chimeric-Antigen-Receptor- Transduced T Cells," Blood 119:2709-2720 (2012).

Kochenderfer, J. N., et al., "Construction and Pre-Clinical Evaluation of an Anti-CD19 Chimeric Antigen Receptor," J. Immunother. 32(7):689-702 (2009).

Le Dieu, R., et al., "Peripheral Blood T Cells in Acute Myeloid Leukemia (AML) Patients at Diagnosis Have Abnormal Phenotype and Genotype and Form Defective Immune Synapses with AML Blasts," Blood 114:3909-3916 (2009).

Majeti, R., "Monoclonal Antibody Therapy Directed Against Human Acute Myeloid Leukemia Stem Cells," Oncogene 30:1009-1019 (2011).

Majeti, R., et al., "CD47 Is an Adverse Prognostic Factor and Therapeutic Antibody Target on Human Acute Myeloid Leukemia Stem Cells," Cell 138:286-299 (2009).

Manz, M. G., et al., "Prospective Isolation of Human Clonogenic Common Myeloid Progenitors," PNAS 99 (18):11872-11877 (2002).

Mardiros et al., "CD123-Specific Chimeric Antigen Receptor Redirected T Cells Exhibit Potent Cytolytic Activity and Multiple Effector Functions Against Acute Myeloid Leukemia without Altering Normal Hematopoietic Colony Formation in Vitro", BLOOD, vol. 120, No. 21, Nov. 16, 2012, 2 pages.

Mardiros et al., "T cells expressing CD123-specific chimeric antigen receptors ehibit specific cytolytic effector functions and anti-tumor effects against human acute myeloid leukemia", Blood, Oct. 31, 2013, vol. 122, No. 18, pp. 3138-3148.

Mardiros et al., Materials and Methods, pp. 1-14, Supplement to "T cells expressing CD123-specific chimeric antigen receptors exhibit

(56) References Cited

OTHER PUBLICATIONS specific cytolytic effector functions and antitumor effects against human acute myeloid leukemia", Blood, Oct. 31, 2013, vol. 122, No. 18, pp. 3138-3148, published online Sep. 12, 2013.
Milone, M. C., et al., "Chimeric Receptors Containing CD 137 Signal Transduction Domains Mediate Enhanced Survival of T Cells and Increased Antileukemic Efficacy In Vivo," Mol. Ther. 17(8):1453-1464 (2009).
Moeller, M., et al., "Sustained Antigen-Specific Antitumor Recall Response Mediated by Gene- Modified CD4+ T Helper-1 and CD8+ T Cells," Cancer Res. 67:11428-11437 (2007).
Munoz, L., et al., "Interleukin-3 Receptor Alpha Chain (CD123) is Widely Expressed in Hematologic Malignancies," Haematologica 86:1261-1269 (2001).
Nakazawa et al., "PiggyBac-mediated cancer immunotherapy using EBV-specific cytotoxic T-cells expressing HER2-specific chimeric antigen receptor." Molecular Therapy. Dec. 1, 2011, 19(12):2133-43.
Nguyen, P., et al., "Identification of a Murine CD28 Dileucine Motif that Suppresses Single- Chain Chimeric T-Cell Receptor Expression and Function, " Blood 102:4320-4325 (2003).
Niwa et al., "IgG subclass-independent improvement of antibody-dependent cellular cytotoxicity by fucose removal from Asn297-linked oligosaccharides," J of Immunol Meth., 2005, 306:151-160.
Oka, Y., et al., Induction of WT1 (Wilms' Tumor Gene)-Specific Cytotoxic T Lymphocytes by VVT1 Peptide Vaccine and the Resultant Cancer Regression,' PNAS 101(38):13885-13890 (2004).
Park et al., "Abstract 1944: In vitro analysis of suicide gene expression and function in human T lymphocytes transduced to express a tumor targeted chimeric antigen receptor," Cancer Research (2010) vol. 70, No. 8 Supplement, p. 1944 (Abstract 1944) [online], Internet <URL:http://cancerres.aacrjournals.org/content/70/8_Supplement/1944>, 4 pages.
Peinert, S., et al., "Gene-Modified T Cells as Immunotherapy for Multiple Myeloma and Acute Myeloid Leukemia Expressing the Lewis Y Antigen," Gene Therapy 17:678-686 (2010).
Pelloquin, F., et al., "Human B Lymphocytes Immortalization by Epstein-Barr Virus in the Presence of Cyclosporin A," In Vitro Cell. Dev. Biol. 22(12):689-694 (1986).
Reddy, M. P., et al., "Elimination of Fc Receptor-Dependent Effector Functions of a Modified IgG4 Monoclonal Antibody to Human CD4," J. Immunol. 164:1925-1933 (2000).
Riddell, S. R., et al., "The use of Anti-CD3 and Anti-CD28 Monoclonal Antibodies to Clone and Expand Human Antigen-Specific T Cells," J. Immunol. Methods 128:189-201 (1990).

Russian Office Action in Russian Application No. 2015140624, dated Feb. 13, 2018, 14 pages (with English Translation).
Sato, N., et al., "Expression and Factor-Dependent Modulation of the Interleukin-3 Receptor Subunits on Human Hematopoietic Cells," Blood 82:752-761 (1993).
Savoldo, B., et al., "CD28 Costimulation Improves Expansion and Persistence of Chimeric Antigen Receptor-Modified T Cells in Lymphoma Patients," J. Clin. Invest. 121(5): 1822-1826 (2011).
Schietinger, A., et al., "Bystander Killing of Cancer Requires the Cooperation of CD4+ and CD8+ T Cells During the Effector Phase," J. Exp. Med. 207(11):2469-2477 (2010).
Seder, R. A., et al., "T-Cell Quality in Memory and Protection: Implications for Vaccine Design," Nat. Rev. Immunol. 8:247-258 (2008).
Sievers, E. L., et al.," Efficacy and Safety of Gemtuzumab Ozogamicin in Patients with CD33-Positive Acute Myeloid Leukemia in First Relapse," J. Clin. Oncol. 19:3244-3254 (2001).
Straathof, K. C., et al., "An Inducible Caspase 9 Safety Switch for 1-Cell Therapy," Blood 105:4247-4254 (2005).
Strohl, W. R., "Optimization of Fc-Mediated Effector Functions of Monoclonal Antibodies," Curr. Op. Biotech. 20:685-691 (2009).
Tettamanti et al., "Targeting of acute myeloid leukaemia by cytokine-induced killer cells redirected with a novel CD 123-specific chimeric antigen receptor," British journal of haematology, May 1, 2013, 161(3):389-401.
Thokala et al., "Targeting Leukemias by CD123 Specific Chimeric Antigen Receptor", BLOOD, vol. 118, No. 21, Nov. 18, 2011, 2 pages.
Till, B. G. et al., "CD20-Specific Adoptive Immunotherapy for Lymphoma Using a Chimeric Antigen Receptor with Both CD28 and 4-1BB Domains: Pilot Clinical Trial Results," Blood 119:3940-3950 (2012).
Tsimberidou, A.M., et al., "The Role of Gemtuzumab Ozogamicin in Acute Leukaemia Therapy," Br. J. Haematol. 132:398-409 (2005).
Walter, R. B., et al., "Acute Myeloid Leukemia Stem Cells and CD33-Targeted Immunotherapy," Blood 119:6198-6208 (2012).
Wang, X, et al., "A Transgene-Encoded Cell Surface Polypeptide for Selection, In Vivo Tracking, and Ablation of Engineered Cells," Blood 118:1255-1263 (2011).
Yoon, S.H., et al., "Adoptive Immunotherapy Using Human Peripheral Blood Lymphocytes Transferred with RNA Encoding Her-2/Neu-Specific Chimeric Immune Receptor in Ovarian Cancer Xenograft Model," Cancer Gene Ther. 16:489-497 (2009).
Flamar et al., "Non-covalent Assembly of Anti-Dendritic Cell Antibodies and Antigens for Evoking Immune Responses in vitro and in vivo," J Immunol., Sep. 1, 2012, 189(5):2645-2655.

Fig. 4
A
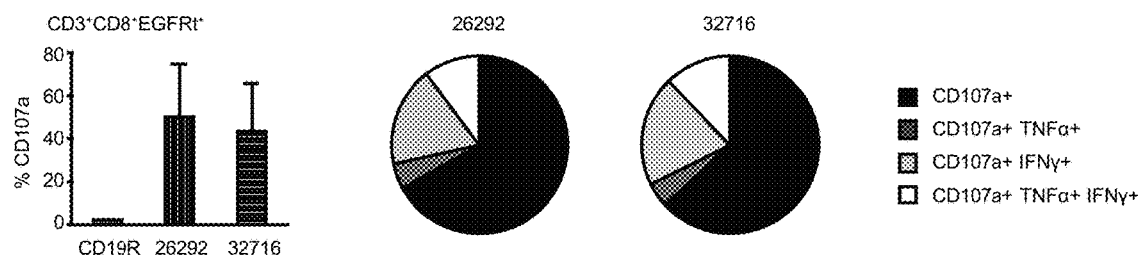
B
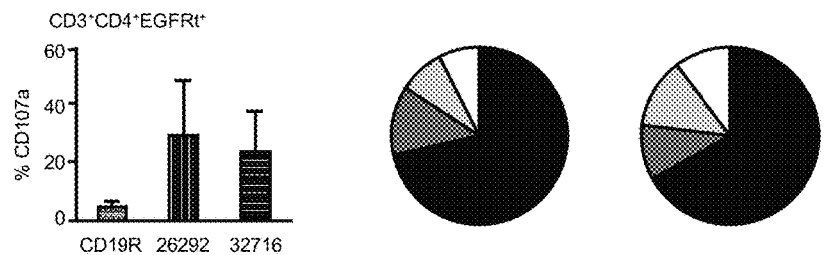
C
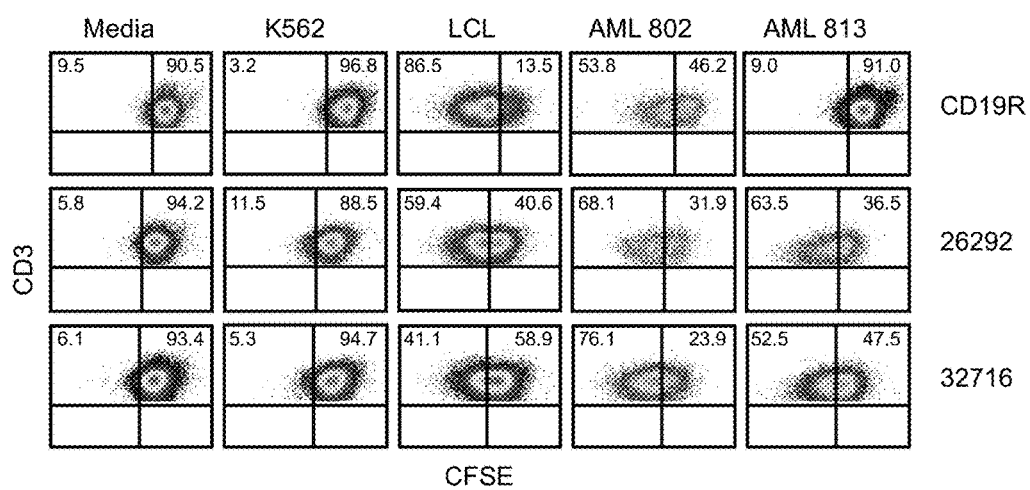

Fig. 10

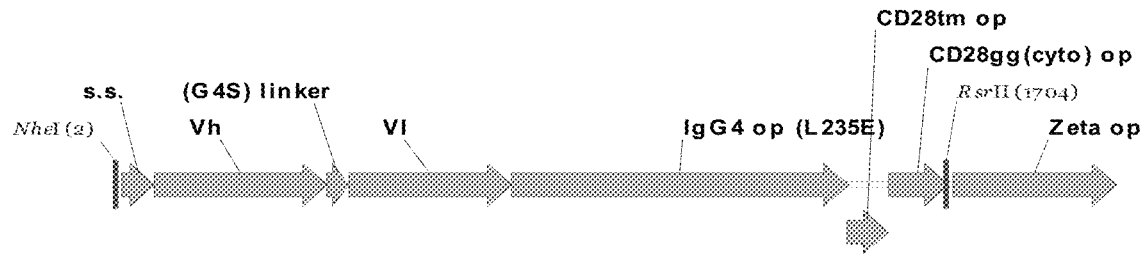

IL3scfv-IgG4(L235E)-CD28gg-Zeta (32716)- before CO
2052 bp

```
    NheI
    ↓~~~~~~        GMCSFR alpha signal sequence →
                 M   L   L   L   V   T   S   L   L   L   C   E   L   P   H
  1 GCTAGCGCCG CCACCATGCT GCTGCTGGTG ACCAGCCTGC TGCTGTGCGA GCTGCCCCAC
    CGATCGCGGC GGTGGTACGA CGACGACCAC TGGTCGGACG ACGACACGCT CGACGGGGTG
                 Vh (32716) →
     P   A   F   L   L   I   P   Q   I   Q   L   V   Q   S   G   P   E   L   K   K
 61 CCCGCCTTTC TGCTGATCCC CCAGATTCAG CTGGTGCAGA GCGGCCCGGA ACTGAAAAAA
    GGGCGGAAAG ACGACTAGGG GGTCTAAGTC GACCACGTCT CGCCGGGCCT TGACTTTTTT
     P   G   E   T   V   K   I   S   C   K   A   S   G   Y   I   F   T   N   Y   G
121 CCGGGCGAAA CCGTGAAAAT TAGCTGCAAA GCGAGCGGCT ATATTTTTAC CAACTATGGC
    GGCCCGCTTT GGCACTTTTA ATCGACGTTT CGCTCGCCGA TATAAAAATG GTTGATACCG
     M   N   W   V   K   Q   A   P   G   K   S   F   K   W   M   G   W   I   N   T
181 ATGAACTGGG TGAAACAGGC GCCGGGCAAA AGCTTTAAAT GGATGGGCTG GATTAACACC
    TACTTGACCC ACTTTGTCCG CGGCCCGTTT TCGAAATTTA CCTACCCGAC CTAATTGTGG
     Y   T   G   E   S   T   Y   S   A   D   F   K   G   R   F   A   F   S   L   E
241 TATACCGGCG AAAGCACCTA TAGCGCGGAT TTTAAAGGCC GCTTTGCGTT TAGCCTGGAA
    ATATGGCCGC TTTCGTGGAT ATCGCGCCTA AAATTTCCGG CGAAACGCAA ATCGGACCTT
     T   S   A   S   T   A   Y   L   H   I   N   D   L   K   N   E   D   T   A   T
301 ACCAGCGCGA GCACCGCGTA TCTGCATATT AACGATCTGA AAAACGAAGA TACCGCGACC
    TGGTCGCGCT CGTGGCGCAT AGACGTATAA TTGCTAGACT TTTTGCTTCT ATGGCGCTGG
     Y   F   C   A   R   S   G   Y   D   P   M   D   Y   W   G   Q   G   T   S
361 TATTTTTGCG CGCGCAGCGG CGGCTATGAT CCGATGGATT ATTGGGGCCA GGGCACCAGC
    ATAAAAACGC GCGCGTCGCC GCCGATACTA GGCTACCTAA TAACCCCGGT CCCGTGGTCG
                              G4S linker →
     V   T   V   S   S   G   G   G   G   S   G   G   G   G   S   G   G   G   G   S
421 GTGACCGTGA GCAGCGGCGG CGGCGGCAGC GGCGGCGGCG GCAGCGGCGG CGGCGGCAGC
    CACTGGCACT CGTCGCCGCC GCCGCCGTCG CCGCCGCCGC CGTCGCCGCC GCCGCCGTCG
                 Vl (32716) →
     D   I   V   L   T   Q   S   P   A   S   L   A   V   S   L   G   Q   R   A   T
481 GATATTGTGC TGACCCAGAG CCCGGCGAGC CTGGCGGTGA GCCTGGGCCA GCGCGCGACC
    CTATAACACG ACTGGGTCTC GGGCCGCTCG GACCGCCACT CGGACCCGGT CGCGCGCTGG
     I   S   C   R   A   S   E   S   V   D   N   Y   G   N   T   F   M   H   W   Y
541 ATTAGCTGCC GCGCGAGCGA AAGCGTGGAT AACTATGGCA ACACCTTTAT GCATTGGTAT
    TAATCGACGG CGCGCTCGCT TTCGCACCTA TTGATACCGT TGTGGAAATA CGTAACCATA
     Q   Q   K   P   G   Q   P   P   K   L   L   I   Y   R   A   S   N   L   E   S
601 CAGCAGAAAC CGGGCCAGCC GCCGAAACTG CTGATTTATC GCGCGAGCAA CCTGGAAAGC
    GTCGTCTTTG GCCCGGTCGG CGGCTTTGAC GACTAAATAG CGCGCTCGTT GGACCTTTCG
     G   I   P   A   R   F   S   G   S   G   S   R   T   D   F   T   L   T   I   N
661 GGCATTCCGG CGCGCTTTAG CGGCAGCGGC AGCCGCACCG ATTTTACCCT GACCATTAAC
    CCGTAAGGCC GCGCGAAATC GCCGTCGCCG TCGGCGTGGC TAAAATGGGA CTGGTAATTG
```

Fig. 10 (cont.)

```
              P   V   E   A   D   D   V   A   T   Y   Y   C   Q   Q   S   N   E   D   P   P
    721   CCGGTGGAAG CGGATGATGT GGCGACCTAT TATTGCCAGC AGAGCAACGA AGATCCGCCG
          GGCCACCTTC GCCTACTACA CCGCTGGATA ATAACGGTCG TCTCGTTGCT TCTAGGCGGC
                                                          IgG4op(L235E)→
              T   F   G   A   G   T   K   L   E   L   K   E   S   K   Y   G   P   P   C   P
    781   ACCTTTGGCG CGGGCACCAA ACTGGAACTG AAAGAGAGCA AGTACGGCCC TCCCTGCCCC
          TGGAAACCGC GCCCGTGGTT TGACCTTGAC TTTCTCTCGT TCATGCCGGG AGGGACGGGG
              P   C   P   A   P   E   F   E   G   G   P   S   V   F   L   F   P   P   K   P
    841   CCTTGCCCTG CCCCCGAGTT CGAGGGCGGA CCCAGCGTGT TCCTGTTCCC CCCCAAGCCC
          GGAACGGGAC GGGGGCTCAA GCTCCCGCCT GGGTCGCACA AGGACAAGGG GGGGTTCGGG
              K   D   T   L   M   I   S   R   T   P   E   V   T   C   V   V   V   D   V   S
    901   AAGGACACCC TGATGATCAG CCGGACCCCC GAGGTGACCT GCGTGGTGGT GGACGTGAGC
          TTCCTGTGGG ACTACTAGTC GGCCTGGGGG CTCCACTGGA CGCACCACCA CCTGCACTCG
              Q   E   D   P   E   V   Q   F   N   W   Y   V   D   G   V   E   V   H   N   A
    961   CAGGAAGATC CCGAGGTCCA GTTCAATTGG TACGTGGACG GCGTGGAAGT GCACAACGCC
          GTCCTTCTAG GGCTCCAGGT CAAGTTAACC ATGCACCTGC CGCACCTTCA CGTGTTGCGG
              K   T   K   P   R   E   E   Q   F   N   S   T   Y   R   V   V   S   V   L   T
    1021  AAGACCAAGC CCAGAGAGGA ACAGTTCAAC AGCACCTACC GGGTGGTGTC TGTGCTGACC
          TTCTGGTTCG GGTCTCTCCT TGTCAAGTTG TCGTGGATGG CCCACCACAG ACACGACTGG
              V   L   H   Q   D   W   L   N   G   K   E   Y   K   C   K   V   S   N   K   G
    1081  GTGCTGCACC AGGACTGGCT GAACGGCAAA GAATACAAGT GCAAGGTGTC CAACAAGGGC
          CACGACGTGG TCCTGACCGA CTTGCCGTTT CTTATGTTCA CGTTCCACAG GTTGTTCCCG
              L   P   S   S   I   E   K   T   I   S   K   A   K   G   Q   P   R   E   P   Q
    1141  CTGCCCAGCA GCATCGAAAA GACCATCAGC AAGGCCAAGG GCCAGCCTCG CGAGCCCCAG
          GACGGGTCGT CGTAGCTTTT CTGGTAGTCG TTCCGGTTCC CGGTCGGAGC GCTCGGGGTC
              V   Y   T   L   P   P   S   Q   E   E   M   T   K   N   Q   V   S   L   T   C
    1201  GTGTACACCC TGCCTCCCTC CCAGGAAGAG ATGACCAAGA ACCAGGTGTC CCTGACCTGC
          CACATGTGGG ACGGAGGGAG GGTCCTTCTC TACTGGTTCT TGGTCCACAG GGACTGGACG
              L   V   K   G   F   Y   P   S   D   I   A   V   E   W   E   S   N   G   Q   P
    1261  CTGGTGAAGG GCTTCTACCC CAGCGACATC GCCGTGGAGT GGGAGAGCAA CGGCCAGCCT
          GACCACTTCC CGAAGATGGG GTCGCTGTAG CGGCACCTCA CCCTCTCGTT GCCGGTCGGA
              E   N   N   Y   K   T   T   P   P   V   L   D   S   D   G   S   F   F   L   Y
    1321  GAGAACAACT ACAAGACCAC CCCTCCCGTG CTGGACAGCG ACGGCAGCTT CTTCCTGTAC
          CTCTTGTTGA TGTTCTGGTG GGGAGGGCAC GACCTGTCGC TGCCGTCGAA GAAGGACATG
              S   R   L   T   V   D   K   S   R   W   Q   E   G   N   V   F   S   C   S   V
    1381  AGCCGGCTGA CCGTGGACAA GAGCCGGTGG CAGGAAGGCA ACGTCTTTAG CTGCAGCGTG
          TCGGCCGACT GGCACCTGTT CTCGGCCACC GTCCTTCCGT TGCAGAAATC GACGTCGCAC
              M   H   E   A   L   H   N   H   Y   T   Q   K   S   L   S   L   S   L   G   K
    1441  ATGCACGAGG CCCTGCACAA CCACTACACC CAGAAGAGCC TGAGCCTGTC CCTGGGCAAG
          TACGTGCTCC GGGACGTGTT GGTGATGTGG GTCTTCTCGG ACTCGGACAG GGACCCGTTC
          CD28tm op→
              M   F   W   V   L   V   V   V   G   G   V   L   A   C   Y   S   L   L   V   T
    1501  ATGTTCTGGG TGCTGGTGGT GGTGGGCGGA GTGCTGGCCT GCTACAGCCT GCTGGTGACA
          TACAAGACCC ACGACCACCA CCACCCGCCT CACGACCGGA CGATGTCGGA CGACCACTGT
                                                          CD28gg(cyto) op→
              V   A   F   I   I   F   W   V   R   S   K   R   S   R   G   G   H   S   D   Y
    1561  GTGGCCTTCA TCATCTTTTG GGTGCGGAGT AAGCGAAGCA GAGGCGGACA TAGCGACTAC
          CACCGGAAGT AGTAGAAAAC CCACGCCTCA TTCGCTTCGT CTCCGCCTGT ATCGCTGATG
              M   N   M   T   P   R   R   P   G   P   T   R   K   H   Y   Q   P   Y   A   P
    1621  ATGAACATGA CCCCAAGACG GCCTGGCCCT ACCCGGAAGC ACTACCAGCC CTACGCCCCA
          TACTTGTACT GGGGTTCTGC CGGACCGGGA TGGGCCTTCG TGATGGTCGG GATGCGGGGT
```

Fig. 10 (cont.)

```
                              RsrII                    Zeta op→
           P   R   D   F   A   A   Y   R   S   G   G   G   R   V   K   F   S   R   S   A
1681     CCCAGGGACT TTGCGGCCTA CCGGTCCGGC GGAGGGCGGG TGAAGTTCAG CAGAAGCGCC
         GGGTCCCTGA AACGCCGGAT GGCCAGGCCG CCTCCCGCCC ACTTCAAGTC GTCTTCGCGG
           D   A   P   A   Y   Q   Q   G   Q   N   Q   L   Y   N   E   L   N   L   G   R
1741     GACGCCCCTG CCTACCAGCA GGGCCAGAAT CAGCTGTACA ACGAGCTGAA CCTGGGCAGA
         CTGCGGGGAC GGATGGTCGT CCCGGTCTTA GTCGACATGT TGCTCGACTT GGACCCGTCT
           R   E   E   Y   D   V   L   D   K   R   R   G   R   D   P   E   M   G   G   K
1801     AGGGAAGAGT ACGACGTCCT GGATAAGCGG AGAGGCCGGG ACCCTGAGAT GGGCGGCAAG
         TCCCTTCTCA TGCTGCAGGA CCTATTCGCC TCTCCGGCCC TGGGACTCTA CCCGCCGTTC
           P   R   R   K   N   P   Q   E   G   L   Y   N   E   L   Q   K   D   K   M   A
1861     CCTCGGCGGA AGAACCCCCA GGAAGGCCTG TATAACGAAC TGCAGAAAGA CAAGATGGCC
         GGAGCCGCCT TCTTGGGGGT CCTTCCGGAC ATATTGCTTG ACGTCTTTCT GTTCTACCGG
           E   A   Y   S   E   I   G   M   K   G   E   R   R   R   G   K   G   H   D   G
1921     GAGGCCTACA GCGAGATCGG CATGAAGGGC GAGCGGAGGC GGGGCAAGGG CCACGACGGC
         CTCCGGATGT CGCTCTAGCC GTACTTCCCG CTCGCCTCCG CCCCGTTCCC GGTGCTGCCG
           L   Y   Q   G   L   S   T   A   T   K   D   T   Y   D   A   L   H   M   Q   A
1981     CTGTATCAGG GCCTGTCCAC CGCCACCAAG GATACCTACG ACGCCCTGCA CATGCAGGCC
         GACATAGTCC CGGACAGGTG GCGGTGGTTC CTATGGATGC TGCGGGACGT GTACGTCCGG
           L   P   P   R
2041     CTGCCCCCAA GG
         GACGGGGGTT CC
```

Fig. 11

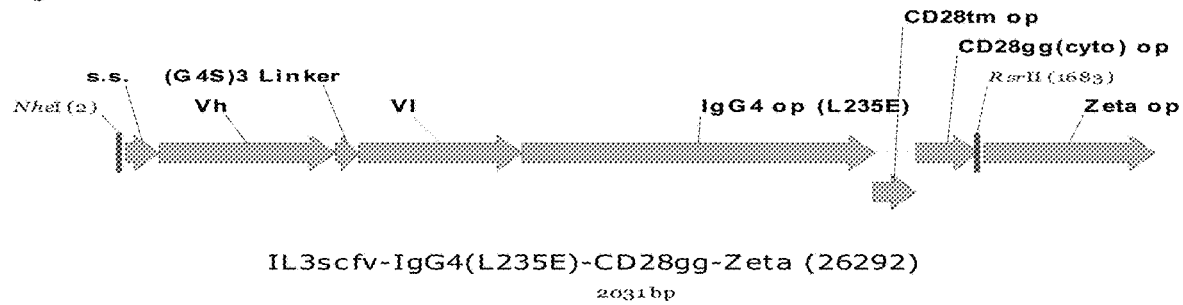

IL3scfv-IgG4(L235E)-CD28gg-Zeta (26292)
2031bp

```
       NheI
        ↓~~~~~~~      GMCSFR alpha signal sequence →
                     M   L   L   L   V   T   S   L   L     L   C   E   L   P   H
   1   GCTAGCGCCG CCACCATGCT GCTGCTGGTG ACCAGCCTGC TGCTGTGCGA GCTGCCCCAC
       CGATCGCGGC GGTGGTACGA CGACGACCAC TGGTCGGACG ACGACACGCT CGACGGGGTG
                             Vh (26292) →
        P   A   F   L   L   I   P     Q   V   Q   L   Q   Q   P   G   A   E   L   V   R
  61   CCCGCCTTTC TGCTGATCCC CCAGGTGCAG CTGCAGCAGC CGGGCGCGGA ACTGGTGCGC
       GGGCGGAAAG ACGACTAGGG GGTCCACGTC GACGTCGTCG GCCCGCGCCT TGACCACGCG
        P   G   A   S   V   K   L     S   C   K   A   S   G   Y   T   F   T   S   Y   W
 121   CCGGGCGCCA GCGTGAAACT GAGCTGCAAA GCGAGCGGCT ATACCTTTAC CAGCTATTGG
       GGCCCGCGGT CGCACTTTGA CTCGACGTTT CGCTCGCCGA TATGGAAATG GTCGATAACC
        M   N   W   V   K   Q   R     P   D   Q   G   L   E   W   I   G   R   I   D   P
 181   ATGAACTGGG TGAAACAGCG CCCGGATCAG GGCTGGAAT GGATTGGCCG CATTGATCCG
       TACTTGACCC ACTTTGTCGC GGGCCTAGTC CCGGACCTTA CCTAACCGGC GTAACTAGGC
        Y   D   S   E   T   H   Y     N   Q   K   F   K   D   K   A   I   L   T   V   D
 241   TATGATAGCG AAACCCATTA TAACCAGAAA TTTAAGATA AAGCGATTCT GACCGTGGAT
       ATACTATCGC TTTGGGTAAT ATTGGTCTTT AAATTCTAT TTCGCTAAGA CTGGCACCTA
        K   S   S   T   A   Y   M     Q   L   S   S   L   T   S   E   D   S   A   V
 301   AAAAGCAGCA GCACCGCGTA TATGCAGCTG AGCAGCCTGA CCAGCGAAGA TAGCGCGGTG
       TTTTCGTCGT CGTGGCGCAT ATACGTCGAC TCGTCGGACT GGTCGCTTCT ATCGCGCCAC
        Y   Y   C   A   R   G   N     W   D   D   Y   W   G   Q   G   T   T   L   T   V
 361   TATTATTGCG CGCGCGGCAA CTGGGATGAT TATTGGGGCC AGGGCACCAC CCTGACCGTG
       ATAATAACGC GCGCGCCGTT GACCCTACTA ATAACCCCGG TCCCGTGGTG GGACTGGCAC
                    G4S linker→                                                  Vl (26292) →
        S   S   G   G   G   S   G   G   G   G   S   G   G   G   G   S     D   V   Q
 421   AGCAGCGGCG GCGGCGGCAG CGGCGGCGGC GGCAGCGGCG GCGGCGGCAG CGATGTGCAG
       TCGTCGCCGC CGCCGCCGTC GCCGCCGCCG CCGTCGCCGC CGCCGCCGTC GCTACACGTC
        I   T   Q   S   P   S   Y     L   A   A   S   P   G   E   T   I   T   I   N   C
 481   ATTACCCAGA GCCCGAGCTA TCTGGCGGCG AGCCCGGGCG AAACCATTAC CATTAACTGC
       TAATGGGTCT CGGGCTCGAT AGACCGCCGC TCGGGCCCGC TTTGGTAATG GTAATTGACG
        R   A   S   K   S   I   S     K   D   L   A   W   Y   Q   E   K   P   G   K   T
 541   CGCGCGAGCA AAAGCATTAG CAAAGATCTG GCGTGGTATC AGAAAAAACC GGGCAAAACC
       GCGCGCTCGT TTTCGTAATC GTTTCTAGAC CGCACCATAG TCTTTTTTGG CCCGTTTTGG
        N   K   L   L   I   Y   S     G   T   L   Q   S   G   I   P   S   R   F   S
 601   AACAAACTGC TGATTTATAG CGGCAGCACC CTGCAGAGCG GCATTCCGAG CCGCTTTAGC
       TTGTTTGACG ACTAAATATC GCCGTCGTGG GACGTCTCGC CGTAAGGCTC GGCGAAATCG
        G   S   G   S   G   T   D     F   T   L   T   I   S   S   L   E   P   E   D   F
 661   GGCAGCGGCA GCGGCACCGA TTTTACCCTG ACCATTAGCA GCCTGGAACC GGAAGATTTT
       CCGTCGCCGT CGCCGTGGCT AAAATGGGAC TGGTAATCGT CGGACCTTGG CCTTCTAAAA
        A   M   Y   Y   C   Q   Q     H   N   K   Y   P   Y   T   F   G   G   G   T   K
 721   GCGATGTATT ATTGCCAGCA GCATAACAAA TATCCGTATA CCTTTGGCGG CGGCACCAAA
       CGCTACATAA TAACGGTCGT CGTATTGTTT ATAGGCATAT GGAAACCGCC GCCGTGGTTT
```

Fig. 11 (cont.)

```
             IgG4op(L235E)→
           L  E  I  K  E  S  K  Y  G  P     P  C  P  P  C  P  A  P  E  F
      781  CTGGAAATTA AAGAGAGCAA GTACGGCCCT CCGTGCCCGC CTTGCCCGGC CGCCGGAGTTC
           GACCTTTAAT TTCTCTCGTT CATGCCGGGA GGACGGGCG GAACGGGCCG GCGGCTCAAG
           E  G  G  P  S  V  F  L  F  P     P  K  P  K  D  T  L  M  I  S
      841  GAGGGCGGAC CTAGCGTGTT CCTGTTCCCG CCCAAGCCCA AGGACACCCT GATGATCAGC
           CTCCCGCCTG GATCGCACAA GGACAAGGGC GGGTTCGGGT TCCTGTGGA CTACTAGTCG
           R  T  P  E  V  T  C  V  V  V     D  V  S  Q  E  D  P  E  V  Q
      901  CGGACTCCG AGGTGACCTG CGTGGTGGTG GACGTCAGCC AGGAAGATCC GGAGGTCCAG
           GCCTGAGGGC TCCACTGGAC GCACCACCAC CTGCAGTCGG TCCTTCTAGG CCTCCAGGTC
           F  N  W  Y  V  D  G  V  E  V     H  N  A  K  T  K  P  R  E  E
      961  TTCAATTGGT ACGTGGACGG CGTGGAAGTG CACAACGCCA AGACAAAGCC CAGAGAGGAA
           AAGTTAACCA TGCACCTGCC GCACCTTCAC GTGTTGCGGT TCTGTTTCGG GTCTCTCCTT
           Q  F  N  S  T  Y  R  V  V  S     V  L  T  V  L  H  Q  D  W  L
     1021  CAGTTCAACA GCACCTACCG GGTGGTGTCT GTGCTGACCG TGCTGCACCA GGACTGGCTG
           GTCAAGTTGT CGTGGATGGC CCACCACAGA CACGACTGGC ACGACGTGGT CCTGACCGAC
           N  G  K  E  Y  K  C  K  V  S     N  K  G  L  P  S  S  I  E  K
     1081  AACGGCAAAG AGTACAAGTG CAAGGTGTCC AACAAAGGCC TGCCCAGCAG CATCGAAAAG
           TTGCCGTTTC TCATGTTCAC GTTCCACAGG TTGTTTCCGG ACGGGTCGTC GTAGCTTTC
           T  I  S  K  A  K  G  Q  P  R     E  P  Q  V  Y  T  L  P  P  S
     1141  ACCATCAGCA AGGCCAAGGG CCAGCCTCGC GAGCCCCAGG TGTACACCCT GCCTCCTAGC
           TGGTAGTCGT TCCGGTTCCC GGTCGGAGCG CTCGGGGTCC ACATGTGGGA CGGAGGATCG
           Q  E  E  M  T  K  N  Q  V  S     L  T  C  L  V  K  G  F  Y  P
     1201  CAGGAAGAGA TGACCAAGAA CCAGGTGTCC CTGACCTGCC TGGTCAAGGG CTTCTACCCG
           GTCCTTCTCT ACTGGTTCTT GGTCCACAGG GACTGGACGG ACCAGTTCCC GAAGATGGGC
           S  D  I  A  V  E  W  E  S  N     G  Q  P  E  N  N  Y  K  T  T
     1261  AGCGACATCG CCGTGGAGTG GGAGAGCAAC GGCCAGCCTG AGAACAACTA CAAGACCACC
           TCGCTGTAGC GGCACCTCAC CCTCTCGTTG CCGGTCGGAC TCTTGTTGAT GTTCTGGTGG
           P  P  V  L  D  S  D  G  S  F     F  L  Y  S  R  L  T  V  D  K
     1321  CCTCCTGTGC TGGACAGCGA CGGCAGCTTC TTCCTGTACA GCCGGCTGAC CGTGGACAAG
           GGAGGACACG ACCTGTCGCT GCCGTCGAAG AAGGACATGT CGGCCGACTG GCACCTGTTC
           S  R  W  Q  E  G  N  V  F  S     C  S  V  M  H  E  A  L  H  N
     1381  AGCCGCTGGC AGGAAGGCAA CGTCTTTAGC TGCAGCGTGA TGCACGAGGC CCTGCACAAC
           TCGGCGACCG TCCTTCCGTT GCAGAAATCG ACGTCGCACT ACGTGCTCCG GGACGTGTTG
                                                       CD28tm op→
           H  Y  T  Q  K  S  L  S  L  S     L  G  K  M  F  W  V  L  V  V
     1441  CACTACACCC AGAAGAGCCT GAGCCTGTCT CTGGGCAAGA TGTTCTGGGT GCTGGTGGTG
           GTGATGTGGG TCTTCTCGGA CTCGGACAGA GACCCGTTCT ACAAGACCCA CGACCACCAC
           V  G  G  V  L  A  C  Y  S  L     L  V  T  V  A  F  I  I  F  W
     1501  GTGGGCGGGG TGCTGGCCTG CTACAGCCTG CTGGTGACAG TGGCCTTCAT CATCTTTTGG
           CACCCGCCCC ACGACCGGAC GATGTCGGAC GACCACTGTC ACCGGAAGTA GTAGAAAACC
             CD28gg(cyto) op→
           V  R  S  K  R  S  R     G  G  H  S  D  Y  M  N  M  T  P  R  R
     1561  GTGCGGAGCA AGCGGAGCAG AGGCGGCCAC AGCGACTACA TGAACATGAC CCCCAGACGG
           CACGCCTCGT TCGCCTCGTC TCCGCCGGTG TCGCTGATGT ACTTGTACTG GGGGTCTGCC
           P  G  P  T  R  K  H  Y  Q  P     Y  A  P  P  R  D  F  A  A  Y
     1621  CCTGGCCCCA CCCGGAAGCA CTACCAGCCC TACGCCCCAC CAGGGACTT TGCCGCCTAC
           GGACCGGGGT GGGCCTTCGT GATGGTCGGG ATGCGGGGTG GTCCCTGAA ACGGCGGATG
           RsrII
           ~~~~~~↓       Zeta op→
           R  S  G  G     G  R  V  K  F  S  R  S  A  D  A  P  A  Y  Q  Q
     1681  CGGTCCGGCG GAGGGCGGGT GAAGTTCAGC AGAAGCGCCG ACGCCCCTGC CTACCAGCAG
           GCCAGGCCGC CTCCCGCCCA CTTCAAGTCG TCTTCGCGGC TGCGGGGACG GATGGTCGTC
```

Fig. 11 (cont.)

```
           G  Q  N  Q     L  Y  N     E  L  N     L  G  R  R     E  E  Y     D  V  L
1741   GGCCAGAATC AGCTGTACAA CGAGCTGAAC CTGGGCAGAA GGGAAGAGTA CGACGTCCTG
       CCGGTCTTAG TCGACATGTT GCTCGACTTG GACCCGTCTT CCCTTCTCAT GCTGCAGGAC
           D  K  R  R     G  R  D     P  E  M     G  G  K  P     R  R  K     N  P  Q
1801   GATAAGCGGA GAGGCCGGGA CCCTGAGATG GGCGGCAAGC CTCGGCGGAA GAACCCCCAG
       CTATTCGCCT CTCCGGCCCT GGGACTCTAC CCGCCGTTCG GAGCCGCCTT CTTGGGGGTC
           E  G  L  Y     N  E  L     Q  K  D     K  M  A  E     A  Y  S     E  I  G
1861   GAAGGCCTGT ATAACGAACT GCAGAAAGAC AAGATGGCCG AGGCCTACAG CGAGATCGGC
       CTTCCGGACA TATTGCTTGA CGTCTTTCTG TTCTACCGGC TCCGGATGTC GCTCTAGCCG
           M  K  G  E     R  R  R     G  K  G     H  D  G  L     Y  Q  G     L  S  T
1921   ATGAAGGGCG AGCGGAGGCG GGGCAAGGGC CACGACGGCC TGTATCAGGG CCTGTCCACC
       TACTTCCCGC TCGCCTCCGC CCCGTTCCCG GTGCTGCCGG ACATAGTCCC GGACAGGTGG
           A  T  K  D     T  Y  D     A  L  H     M  Q  A  L     P  P  R
1981   GCCACCAAGG ATACCTACGA CGCCCTGCAC ATGCAGGCCC TGCCCCCAAG G
       CGGTGGTTCC TATGGATGCT GCGGGACGTG TACGTCCGGG ACGGGGGTTC C
```

Fig. 12

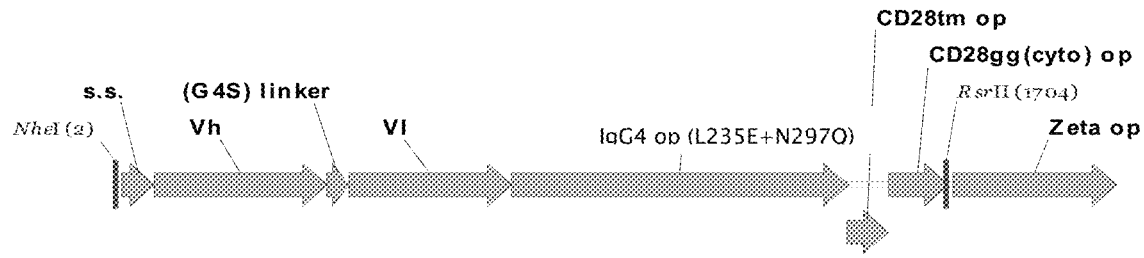

IL3scfv-IgG4(L235E+N297Q)-CD28gg-Zeta (32716)-before CO 2052 bp

```
    NheI
    ↓~~~~~~        GMCSFR alpha signal sequence →
                M   L   L   V   T   S   L   L   L   C   E   L   P   H
  1 GCTAGCGCCG CCACCATGCT GCTGCTGGTG ACCAGCCTGC TGCTGTGCGA GCTGCCCCAC
    CGATCGCGGC GGTGGTACGA CGACGACCAC TGGTCGGACG ACGACACGCT CGACGGGGTG
                       Vh (32716) →
        P   A   F   L   L   I   P   Q   I   Q   L   V   Q   S   G   P   E   L   K   K
 61 CCCGCCTTTC TGCTGATCCC CCAGATTCAG CTGGTGCAGA GCGGCCCGGA ACTGAAAAAA
    GGGCGGAAAG ACGACTAGGG GGTCTAAGTC GACCACGTCT CGCCGGGCCT TGACTTTTTT
        P   G   E   T   V   K   I   S   C   K   A   S   G   Y   I   F   T   N   Y   G
121 CCGGGCGAAA CCGTGAAAAT TAGCTGCAAA GCGAGCGGCT ATATTTTTAC CAACTATGGC
    GGCCCGCTTT GGCACTTTTA ATCGACGTTT CGCTCGCCGA TATAAAAATG GTTGATACCG
        M   N   W   V   K   Q   A   P   G   K   S   F   K   W   M   G   W   I   N   T
181 ATGAACTGGG TGAAACAGGC GCCGGGCAAA AGCTTTAAAT GGATGGGCTG GATTAACACC
    TACTTGACCC ACTTTGTCCG CGGCCCGTTT TCGAAATTTA CCTACCCGAC CTAATTGTGG
        Y   T   G   E   S   T   Y   S   A   D   F   K   G   R   F   A   F   S   L   E
241 TATACCGGCG AAAGCACCTA TAGCGCGGAT TTTAAAGGCC GCTTTGCGTT TAGCCTGGAA
    ATATGGCCGC TTTCGTGGAT ATCGCGCCTA AAATTTCCGG CGAAACGCAA ATCGGACCTT
        T   S   A   S   T   A   Y   L   H   I   N   D   L   K   N   E   D   T   A   T
301 ACCAGCGCGA GCACCGCGTA TCTGCATATT AACGATCTGA AAAACGAAGA TACCGCGACC
    TGGTCGCGCT CGTGGCGCAT AGACGTATAA TTGCTAGACT TTTTGCTTCT ATGGCGCTGG
        Y   F   C   A   R   S   G   Y   D   P   M   D   Y   W   G   Q   G   T   S
361 TATTTTTGCG CGCGCAGCGG CGGCTATGAT CCGATGGATT ATTGGGGCCA GGGCACCAGC
    ATAAAAACGC GCGCGTCGCC GCCGATACTA GGCTACCTAA TAACCCCGGT CCCGTGGTCG
                       G4S linker →
        V   T   V   S   S   G   G   G   G   S   G   G   G   G   S   G   G   G   G   S
421 GTGACCGTGA GCAGCGGCGG CGGCGGCAGC GGCGGCGGCG GCAGCGGCGG CGGCGGCAGC
    CACTGGCACT CGTCGCCGCC GCCGCCGTCG CCGCCGCCGC CGTCGCCGCC GCCGCCGTCG
                       Vl (32716) →
        D   I   V   L   T   Q   S   P   A   S   L   A   V   S   L   G   Q   R   A   T
481 GATATTGTGC TGACCCAGAG CCCGGCGAGC CTGGCGGTGA GCCTGGGCCA GCGCGCGACC
    CTATAACACG ACTGGGTCTC GGGCCGCTCG GACCGCCACT CGGACCCGGT CGCGCGCTGG
        I   S   C   R   A   S   E   S   V   D   N   Y   G   N   T   F   M   H   W   Y
541 ATTAGCTGCC GCGCGAGCGA AAGCGTGGAT AACTATGGCA ACACCTTTAT GCATTGGTAT
    TAATCGACGG CGCGCTCGCT TTCGCACCTA TTGATACCGT TGTGGAAATA CGTAACCATA
        Q   Q   K   P   G   Q   P   P   K   L   L   I   Y   R   A   S   N   L   E   S
601 CAGCAGAAAC CGGGCCAGCC GCCGAAACTG CTGATTTATC GCGCGAGCAA CCTGGAAAGC
    GTCGTCTTTG GCCCGGTCGG CGGCTTTGAC GACTAAATAG CGCGCTCGTT GGACCTTTCG
        G   I   P   A   R   F   S   G   S   G   S   R   T   D   F   T   L   T   I   N
661 GGCATTCCGG CGCGCTTTAG CGGCAGCGGC AGCCGCACCG ATTTTACCCT GACCATTAAC
    CCGTAAGGCC GCGCGAAATC GCCGTCGCCG TCGGCGTGGC TAAAATGGGA CTGGTAATTG
```

Fig. 12 (cont.)

```
            P   V   E   A   D   D   V   A   T   Y    Y   C   Q   Q    S   N   E   D   P   P
      721   CCGGTGGAAG CGGATGATGT GGCGACCTAT TATTGCCAGC AGAGCAACGA AGATCCGCCG
            GGCCACCTTC GCCTACTACA CCGCTGGATA ATAACGGTCG TCTCGTTGCT TCTAGGCGGC
                                                     IgG4op(L235E+NJ297Q)→
            T   F   G   A   G   T   K    L   E   L   K   E   S   K    Y   G   P   P   C   P
      781   ACCTTTGGCG CGGGCACCAA ACTGGAACTG AAAGAGAGCA AGTACGGCCC TCCCTGCCCC
            TGGAAACCGC GCCCGTGGTT TGACCTTGAC TTTCTCTCGT TCATGCCGGG AGGGACGGGG
            P   C   P   A   P   E   F   E    G   G    P   S   V   F   L   F   P   P   K   P
      841   CCTTGCCCTG CCCCCGAGTT CGAGGGCGGA CCCAGCGTGT TCCTGTTCCC CCCCAAGCCC
            GGAACGGGAC GGGGGCTCAA GCTCCCGCCT GGGTCGCACA AGGACAAGGG GGGGTTCGGG
            K   D   T   L    M   I   S   R   T   P    E   V   T   C    V   V   V   D   V   S
      901   AAGGACACCC TGATGATCAG CCGGACCCCC GAGGTGACCT GCGTGGTGGT GGACGTGAGC
            TTCCTGTGGG ACTACTAGTC GGCCTGGGGG CTCCACTGGA CGCACCACCA CCTGCACTCG
            Q   E   D   P    E   V   Q   F   N   W    Y   V   D   G    V   E   V   H   N   A
      961   CAGGAAGATC CCGAGGTCCA GTTCAATTGG TACGTGGACG GCGTGGAAGT GCACAACGCC
            GTCCTTCTAG GGCTCCAGGT CAAGTTAACC ATGCACCTGC CGCACCTTCA CGTGTTGCGG
            K   T   K   P   R   E   E    Q   F   Q    S   T   Y   R    V   V   S   V   L   T
     1021   AAGACCAAGC CCAGAGAGGA ACAGTTCCAA AGCACCTACC GGGTGGTGTC TGTGCTGACC
            TTCTGGTTCG GGTCTCTCCT TGTCAAGGTT TCGTGGATGG CCCACCACAG ACACGACTGG
            V   L   H   Q    D   W   L   N   G   K    E   Y   K   C    K   V   S   N   K   G
     1081   GTGCTGCACC AGGACTGGCT GAACGGCAAA GAATACAAGT GCAAGGTGTC CAACAAGGGC
            CACGACGTGG TCCTGACCGA CTTGCCGTTT CTTATGTTCA CGTTCCACAG GTTGTTCCCG
            L   P   S   S    I   E   K   T   I   S    K   A   K   G    Q   P   R   E   P   Q
     1141   CTGCCCAGCA GCATCGAAAA GACCATCAGC AAGGCCAAGG GCCAGCCTCG CGAGCCCCAG
            GACGGGTCGT CGTAGCTTTT CTGGTAGTCG TTCCGGTTCC CGGTCGGAGC GCTCGGGGTC
            V   Y   T   L    P   P   S   Q   E   E    M   T   K   N    Q   V   S   L   T   C
     1201   GTGTACACCC TGCCTCCCTC CCAGGAAGAG ATGACCAAGA ACCAGGTGTC CCTGACCTGC
            CACATGTGGG ACGGAGGGAG GGTCCTTCTC TACTGGTTCT TGGTCCACAG GGACTGGACG
            L   V   K   G   F   Y   P    S   D   I    A   V   E   W    E   S   N   G   Q   P
     1261   CTGGTGAAGG GCTTCTACCC CAGCGACATC GCCGTGGAGT GGGAGAGCAA CGGCCAGCCT
            GACCACTTCC CGAAGATGGG GTCGCTGTAG CGGCACCTCA CCCTCTCGTT GCCGGTCGGA
            E   N   N   Y   K   T   T    P   P   V    L   D   S   D    G   S   F   F   L   Y
     1321   GAGAACAACT ACAAGACCAC CCCTCCCGTG CTGGACAGCG ACGGCAGCTT CTTCCTGTAC
            CTCTTGTTGA TGTTCTGGTG GGGAGGGCAC GACCTGTCGC TGCCGTCGAA GAAGGACATG
            S   R   L   T    V   D   K   S   R   W    Q   E   G   N    V   F   S   C   S   V
     1381   AGCCGGCTGA CCGTGGACAA GAGCCGGTGG CAGGAAGGCA ACGTCTTTAG CTGCAGCGTG
            TCGGCCGACT GGCACCTGTT CTCGGCCACC GTCCTTCCGT TGCAGAAATC GACGTCGCAC
            M   H   E   A    L   H   N   H   Y   T    Q   K   S   L    S   L   S   L   G   K
     1441   ATGCACGAGG CCCTGCACAA CCACTACACC CAGAAGAGCC TGAGCCTGTC CCTGGGCAAG
            TACGTGCTCC GGGACGTGTT GGTGATGTGG GTCTTCTCGG ACTCGGACAG GGACCCGTTC
            CD28tm op→
            M   F   W   V    L   V   V   V   G   G    V   L   A   C    Y   S   L   L   V   T
     1501   ATGTTCTGGG TGCTGGTGGT GGTGGGCGGA GTGCTGGCCT GCTACAGCCT GCTGGTGACA
            TACAAGACCC ACGACCACCA CCACCCGCCT CACGACCGGA CGATGTCGGA CGACCACTGT
                                                      CD28gg(cyto) op→
            V   A   F   I   I   F   W    V   R   S    K   R   S   R    G   G   H   S   D   Y
     1561   GTGGCCTTCA TCATCTTTTG GGTGCGCAGC AAGCGAAGCA GAGGCGGCCA CAGCGACTAC
            CACCGGAAGT AGTAGAAAAC CCACGCGTCG TTCGCTTCGT CTCCGCCGGT GTCGCTGATG
            M   N   M   T   P   R   R    P   G   P    T   R   K   H    Y   Q   P   Y   A   P
     1621   ATGAACATGA CCCCCAGACG GCCTGGCCCT ACCCGGAAGC ACTACCAGCC CTACGCCCCA
            TACTTGTACT GGGGGTCTGC CGGACCGGGA TGGGCCTTCG TGATGGTCGG GATGCGGGGT
```

Fig. 12 (cont.)

```
                                     RsrII
                                     ~~~~~~~↓       Zeta op→
           P   R   D   F   A   A   Y   R   S   G   G   G   R   V   K   F   S   R   S   A
     1681  CCCAGGGACT TGCCGCCTA CCGGTCCGGC GGAGGGCGGG TGAAGTTCAG CAGAAGCGCC
           GGGTCCCTGA ACGGCGGAT GGCCAGGCCG CCTCCCGCCC ACTTCAAGTC GTCTTCGCGG
           D   A   P   A   Y   Q   Q   G   Q   N   Q   L   Y   N   E   L   N   L   G   R
     1741  GACGCCCTG CCTACCAGCA GGGCCAGAAT CAGCTGTACA ACGAGCTGAA CCTGGGCAGA
           CTGCGGGAC GGATGGTCGT CCCGGTCTTA GTCGACATGT TGCTCGACTT GGACCCGTCT
           R   E   E   Y   D   V   L   D   K   R   R   G   R   D   P   E   M   G   G   K
     1801  AGGGAAGAGT ACGACGTCCT GGATAAGCGG AGAGGCCGGG ACCCTGAGAT GGGCGGCAAG
           TCCCTTCTCA TGCTGCAGGA CCTATTCGCC TCTCCGGCCC TGGGACTCTA CCCGCCGTTC
           P   R   R   K   N   P   Q   E   G   L   Y   N   E   L   Q   K   D   K   M   A
     1861  CCTCGGCGGA AGAACCCCCA GGAAGGCCTG TATAACGAAC TGCAGAAAGA CAAGATGGCC
           GGAGCCGCCT TCTTGGGGGT CCTTCCGGAC ATATTGCTTG ACGTCTTTCT GTTCTACCGG
           E   A   Y   S   E   I   G   M   K   G   E   R   R   R   G   K   G   H   D   G
     1921  GAGGCCTACA GCGAGATCGG CATGAAGGGC GAGCGGAGGC GGGGCAAGGG CCACGACGGC
           CTCCGGATGT CGCTCTAGCC GTACTTCCCG CTCGCCTCCG CCCCGTTCCC GGTGCTGCCG
           L   Y   Q   G   L   S   T   A   T   K   D   T   Y   D   A   L   H   M   Q   A
     1981  CTGTATCAGG GCCTGTCCAC CGCCACCAAG GATACCTACG ACGCCCTGCA CATGCAGGCC
           GACATAGTCC CGGACAGGTG GCGGTGGTTC CTATGGATGC TGCGGGACGT GTACGTCCGG
           L   P   P   R
     2041  CTGCCCCCAA GG
           GACGGGGGTT CC
```

Fig. 13

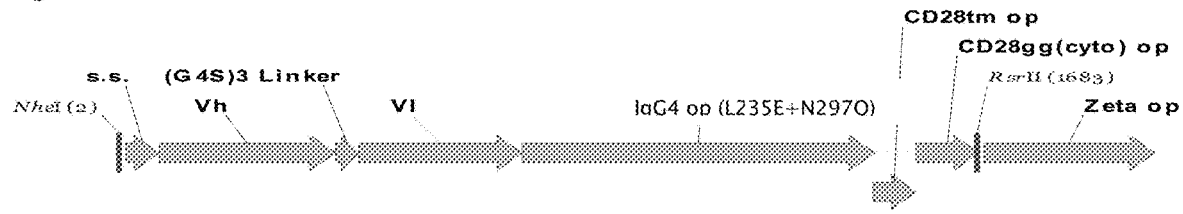

IL3scfv-IgG4(L235E+N297Q)-CD28gg-Zeta (26292)-before CO
2031bp

```
      NheI
      ↓~~~~~        GMCSFR alpha signal sequence →
                    M   L   L   L   V   T   S   L   L   L   C   E   L   P   H
   1  GCTAGCGCCG CCACCATGCT GCTGCTGGTG ACCAGCCTGC TGCTGTGCGA GCTGCCCCAC
      CGATCGCGGC GGTGGTACGA CGACGACCAC TGGTCGGACG ACGACACGCT CGACGGGGTG
                                    Vh (26292) →
                    P   A   F   L   L   I   P   Q   V   Q   L   Q   Q   P   G   A   E   L   V   R
  61  CCCGCCTTTC TGCTGATCCC CCAGGTGCAG CTGCAGCAGC CGGGCGCGGA ACTGGTGCGC
      GGGCGGAAAG ACGACTAGGG GGTCCACGTC GACGTCGTCG GCCCGCGCCT TGACCACGCG
                    P   G   A   S   V   K   L   S   C   K   A   S   G   Y   T   F   T   S   Y   W
 121  CCGGGCGCGA GCGTGAAACT GAGCTGCAAA GCGAGCGGCT ATACCTTTAC CAGCTATTGG
      GGCCCGCGCT CGCACTTTGA CTCGACGTTT CGCTCGCCGA TATGGAAATG GTCGATAACC
                    M   N   W   V   K   Q   R   P   D   Q   G   L   E   W   I   G   R   I   D   P
 181  ATGAACTGGG TGAAACAGCG CCCGGATCAG GGCCTGGAAT GGATTGGCCG CATTGATCCG
      TACTTGACCC ACTTTGTCGC GGGCCTAGTC CCGGACCTTA CCTAACCGGC GTAACTAGGC
                    Y   D   S   E   T   H   Y   N   Q   K   F   K   D   K   A   I   L   T   V   D
 241  TATGATAGCG AAACCCATTA TAACCAGAAA TTTAAAGATA AAGCGATTCT GACCGTGGAT
      ATACTATCGC TTTGGGTAAT ATTGGTCTTT AAATTTCTAT TTCGCTAAGA CTGGCACCTA
                    K   S   S   S   T   A   Y   M   Q   L   S   S   L   T   S   E   D   S   A   V
 301  AAAAGCAGCA GCACCGCGTA TATGCAGCTG AGCAGCCTGA CCAGCGAAGA TAGCGCGGTG
      TTTTCGTCGT CGTGGCGCAT ATACGTCGAC TCGTCGGACT GGTCGCTTCT ATCGCGCCAC
                    Y   Y   C   A   R   G   N   W   D   D   Y   W   G   Q   G   T   T   L   T   V
 361  TATTATTGCG CGCGCGGCAA CTGGGATGAT TATTGGGGCC AGGGCACCAC CCTGACCGTG
      ATAATAACGC GCGCGCCGTT GACCCTACTA ATAACCCCGG TCCCGTGGTG GGACTGGCAC
                    G4S linker→                                                  Vl (26292) →
                    S   S   G   G   G   G   S   G   G   G   G   S   G   G   G   G   S   D   V   Q
 421  AGCAGCGGCG GCGGCGGCAG CGGCGGCGGC GGCAGCGGCG GCGGCGGCAG CGATGTGCAG
      TCGTCGCCGC CGCCGCCGTC GCCGCCGCCG CCGTCGCCGC CGCCGCCGTC GCTACACGTC
                    I   T   Q   S   P   S   Y   L   A   A   S   P   G   E   T   I   T   I   N   C
 481  ATTACCCAGA GCCCGAGCTA TCTGGCGGCG AGCCCGGGCG AAACCATTAC CATTAACTGC
      TAATGGGTCT CGGGCTCGAT AGACCGCCGC TCGGGCCCGC TTTGGTAATG GTAATTGACG
                    R   A   S   K   S   I   S   K   D   L   A   W   Y   Q   E   K   P   G   K   T
 541  CGCGCGAGCA AAAGCATTAG CAAAGATCTG GCGTGGTATC AGGAAAAACC GGGCAAAACC
      GCGCGCTCGT TTTCGTAATC GTTTCTAGAC CGCACCATAG TCCTTTTTGG CCCGTTTTGG
                    N   K   L   L   I   Y   S   G   S   T   L   Q   S   G   I   P   S   R   F   S
 601  AACAAACTGC TGATTTATAG CGGCAGCACC CTGCAGAGCG GCATTCCGAG CCGCTTTAGC
      TTGTTTGACG ACTAAATATC GCCGTCGTGG GACGTCTCGC CGTAAGGCTC GGCGAAATCG
                    G   S   G   S   G   T   D   F   T   L   T   I   S   S   L   E   P   E   D   F
 661  GGCAGCGGCA GCGGCACCGA TTTTACCCTG ACCATTAGCA GCCTGGAACC GGAAGATTTT
      CCGTCGCCGT CGCCGTGGCT AAAATGGGAC TGGTAATCGT CGGACCTTGG CCTTCTAAAA
                    A   M   Y   Y   C   Q   Q   H   N   K   Y   P   Y   T   F   G   G   G   T   K
 721  GCGATGTATT ATTGCCAGCA GCATAACAAA TATCCGTATA CCTTTGGCGG CGGCACCAAA
      CGCTACATAA TAACGGTCGT CGTATTGTTT ATAGGCATAT GGAAACCGCC GCCGTGGTTT
```

Fig. 13 (cont.)

```
                              IgG4op(L235E)→
         L  E  I  K   E  S  K  Y   G  P  P  C   P  P  C  P   A  P  E  F
 781   CTGGAAATTA AAGAGCAGAA GTACGGCCCT CCCTGCCCCC CTTGCCCTGC CCCCGAGTTC
       GACCTTTAAT TTCTCGTCTT CATGCCGGGA GGGACGGGGG GAACGGGACG GGGCTCAAG
          E  G  G  P   S  V  F  L   F  P  P  K   P  K  D  T   L  M  I  S
 841   GAGGGCGGAC CCAGCGTGTT CCTGTTCCCC CCAAAGCCCA AGGACACCCT GATGATCAGC
       CTCCCGCCTG GGTCGCACAA GGACAAGGGG GGTTTCGGGT TCCTGTGGGA CTACTAGTCG
         R  T  P  E   V  T  C  V   V  V  D  V   S  Q  E  D   P  E  V  Q
 901   CGGACCCCCG AGGTGACCTG CGTGGTGGTG GACGTGAGCC AGGAAGATCC CGAGGTCCAG
       GCCTGGGGGC TCCACTGGAC GCACCACCAC CTGCACTCGG TCCTTCTAGG GCTCCAGGTC
         F  N  W  Y   V  D  G  V   E  V  H  N   A  K  T  K   P  R  E  E
 961   TTCAATTGGT ACGTGGACGG CGTGGAAGTG CACAACGCCA AGACCAAGCC CAGAGAGGAA
       AAGTTAACCA TGCACCTGCC GCACCTTCAC GTGTTGCGGT TCTGGTTCGG GTCTCTCCTT
         Q  F  Q  S   T  Y  R  V   V  S  V  L   T  V  L  H   Q  D  W  L
1021   CAGTTCCAGT CCACCTACCG GGTGGTGTCT GTGCTGACCG TGCTGCACCA GGACTGGCTG
       GTCAAGGTCA GGTGGATGGC CCACCACAGA CACGACTGGC ACGACGTGGT CCTGACCGAC
         N  G  K  E   Y  K  C  K   V  S  N  K   G  L  P  S   S  I  E  K
1081   AACGGCAAGG AATACAAGTG CAAGGTGTCC AACAAAGGCC TGCCCAGCAG CATCGAAAAG
       TTGCCGTTCC TTATGTTCAC GTTCCACAGG TTGTTTCCGG ACGGGTCGTC GTAGCTTTTC
         T  I  S  K   A  K  G  Q   P  R  E  P   Q  V  Y  T   L  P  P  S
1141   ACCATCAGCA AGGCCAAGGG CCAGCCTCGC GAGCCCCAGG TGTACACCCT GCCTCCTAGC
       TGGTAGTCGT TCCGGTTCCC GGTCGGAGCG CTCGGGGTCC ACATGTGGGA CGGAGGATCG
         Q  E  E  M   T  K  N  Q   V  S  L  T   C  L  V  K   G  F  Y  P
1201   CAGGAAGAGA TGACCAAGAA CCAGGTGTCC CTGACCTGTC TGGTCAAGGG CTTCTACCCC
       GTCCTTCTCT ACTGGTTCTT GGTCCACAGG GACTGGACAG ACCAGTTCCC GAAGATGGGG
         S  D  I  A   V  E  W  E   S  N  G  Q   P  E  N  N   Y  K  T  T
1261   AGCGACATCG CCGTGGAGTG GGAGAGCAAT GGCCAGCCTG AGAACAACTA CAAGACCACC
       TCGCTGTAGC GGCACCTCAC CCTCTCGTTA CCGGTCGGAC TCTTGTTGAT GTTCTGGTGG
         P  P  V  L   D  S  D  G   S  F  F  L   Y  S  R  L   T  V  D  K
1321   CCTCCTGTGC TGGACAGCGA CGGCAGCTTC TTCCTGTACA GCCGGCTGAC CGTGGACAAG
       GGAGGACACG ACCTGTCGCT GCCGTCGAAG AAGGACATGT CGGCCGACTG GCACCTGTTC
         S  R  W  Q   E  G  N  V   F  S  C  S   V  M  H  E   A  L  H  N
1381   AGCCGGTGGC AGGAAGGGAA CGTCTTTAGC TGCAGCGTGA TGCACGAGGC CCTGCACAAC
       TCGGCCACCG TCCTTCCCTT GCAGAAATCG ACGTCGCACT ACGTGCTCCG GGACGTGTTG
                                                           CD28tm op→
         H  Y  T  Q   K  S  L  S   L  S  L  G   K  M  F  W   V  L  V  V
1441   CACTACACCC AGAAGAGCCT GAGCCTGTCC CTGGGTAAGA TGTTCTGGGT GCTGGTGGTG
       GTGATGTGGG TCTTCTCGGA CTCGGACAGG GACCCATTCT ACAAGACCCA CGACCACCAC
         V  G  G  V   L  A  C  Y   S  L  L  V   T  V  A  F   I  I  F  W
1501   GTGGGCGGGG TGCTGGCCTG CTACAGCCTG CTGGTGACAG TGGCCTTCAT CATCTTTTGG
       CACCCGCCCC ACGACCGGAC GATGTCGGAC GACCACTGTC ACCGGAAGTA GTAGAAAACC
       CD28gg(cyto) op→
         V  R  S  K   R  S  R   G  G   H  S  D  Y   M  N  M  T   P  R  R
1561   GTGCGGAGCA AGCGGAGCAG AGGCGGCCAC AGCGACTACA TGAACATGAC CCCCAGACGG
       CACGCCTCGT TCGCCTCGTC TCCGCCGGTG TCGCTGATGT ACTTGTACTG GGGGTCTGCC
         P  G  P  T   R  K  H  Y   Q  P  Y  A   P  P  R  D   F  A  A  Y
1621   CCTGGCCCCA CCCGGAAGCA CTACCAGCCC TACGCCCCAC CAGGGACTT TGCCGCCTAC
       GGACCGGGGT GGGCCTTCGT GATGGTCGGG ATGCGGGGTG GTCCCTGAA ACGGCGGATG
       RsrII
       ~~~~~~↓            Zeta op→
         R  S  G  G   G  R  V  K   F  S  R  S   A  D  A  P   A  Y  Q  Q
1681   CGGTCCGGCG GAGGGCGGGT GAAGTTCAGC AGAAGCGCCG ACGCCCCTGC CTACCAGCAG
       GCCAGGCCGC CTCCCGCCCA CTTCAAGTCG TCTTCGCGGC TGCGGGGACG GATGGTCGTC
```

Fig. 13 (cont.)

```
           G  Q  N  Q  L  Y  N     E  L  N     L  G  R  R     E  E  Y     D  V  L
1741  GGCCAGAATC AGCTGTACAA CGAGCTGAAC CTGGGCAGAA GGGAAGAGTA CGACGTCCTG
      CCGGTCTTAG TCGACATGTT GCTCGACTTG GACCCGTCTT CCCTTCTCAT GCTGCAGGAC
           D  K  R  R     G  R  D     P  E  M     G  G  K     P  R  R  K     N  P  Q
1801  GATAAGCGGA GAGGCCGGA CCCTGAGATG GGCGGCAAGC CTCGGCGGAA GAACCCCCAG
      CTATTCGCCT CTCCGGCCCT GGGACTCTAC CCGCCGTTCG GAGCCGCCTT CTTGGGGGTC
           E  G  L  Y     N  E  L     Q  K  D     K  M  A  E     A  Y  S     E  I  G
1861  GAAGGCCTGT ATAACGAACT GCAGAAAGAC AAGATGGCCG AGGCCTACAG CGAGATCGGC
      CTTCCGGACA TATTGCTTGA CGTCTTTCTG TTCTACCGGC TCCGGATGTC GCTCTAGCCG
           M  K  G  E     R  R  R     G  K  G     H  D  G  L     Y  Q  G     L  S  T
1921  ATGAAGGGCG AGCGGAGGCG GGGCAAGGGC CACGACGGCC TGTATCAGGG CCTGTCCACC
      TACTTCCCGC TCGCCTCCGC CCCGTTCCCG GTGCTGCCGG ACATAGTCCC GGACAGGTGG
           A  T  K  D     T  Y  D     A  L  H     M  Q  A  L     P  P  R
1981  GCCACCAAGG ATACCTACGA CGCCCTGCAC ATGCAGGCCC TGCCCCCAAG G
      CGGTGGTTCC TATGGATGCT GCGGGACGTG TACGTCCGGG ACGGGGGTTC C
```

Fig. 14
A
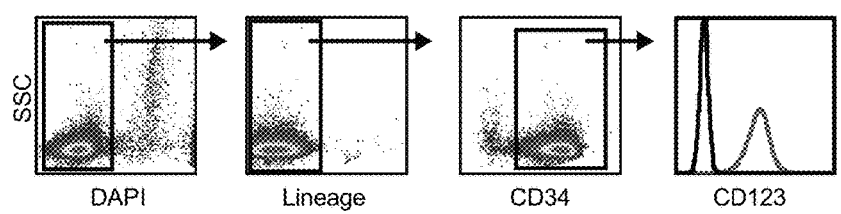
B
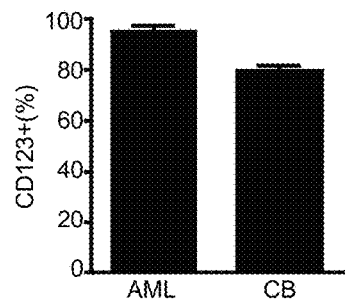
C
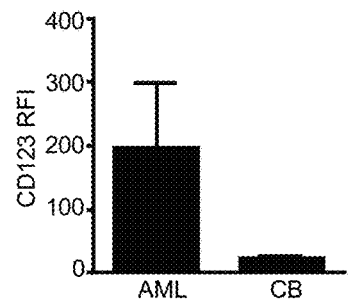
D
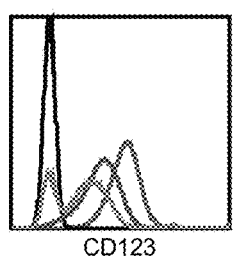

Fig. 16
A
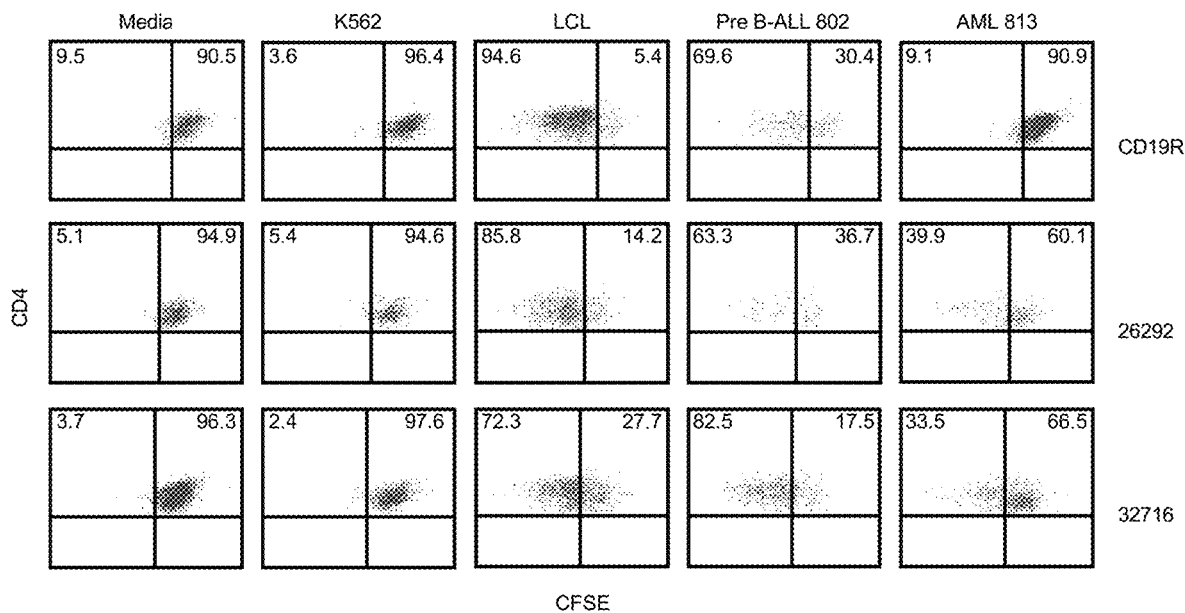
B
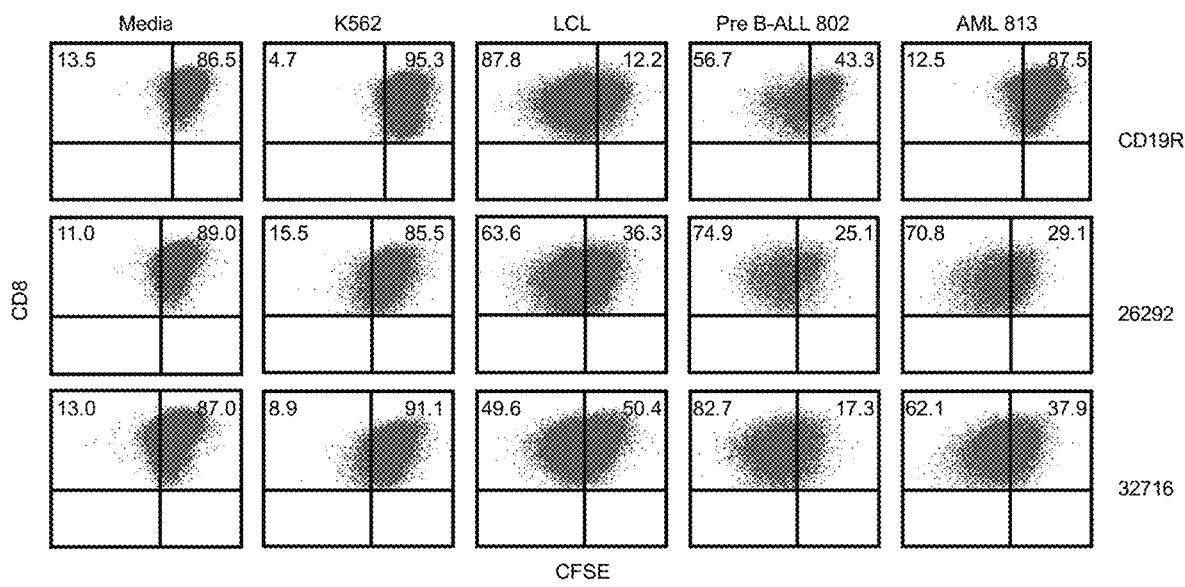

CD123-SPECIFIC CHIMERIC ANTIGEN RECEPTOR REDIRECTED T CELLS AND METHODS OF THEIR USE

CROSS-REFERENCE TO RELATED APPLICATION

This application is a divisional of U.S. application Ser. No. 15/601,793, filed on May 22, 2017, which is a continuation application of and claims priority to U.S. application Ser. No. 13/844,048, filed on Mar. 15, 2013, the entire contents of each of which are herein incorporated by reference.

GOVERNMENT INTEREST

This invention was made with government support under P50 CA107399, and P01 CA030206 awarded by the National Institutes of Health. The government has certain rights in the invention.

BACKGROUND

Acute myeloid leukemia (AML) is a disease characterized by the rapid proliferation of immature myeloid cells in the bone marrow resulting in dysfunctional hematopoiesis [1]. First-line treatments for acute myeloid leukemia (AML) have remained largely unchanged for nearly 50 years and AML remains a disease of poor prognosis. Although standard induction chemotherapy can induce complete remissions, many patients eventually relapse and succumb to the disease [2]. Therefore, the development of novel therapeutics for AML is crucial.

Allogeneic hematopoietic cell transplantation can achieve cure of the disease in selected patients and highlights the susceptibility of AML to donor derived immunotherapy. Additionally, the interleukin 3 receptor alpha chain (CD123) has been identified as a potential immunotherapeutic target since it is over-expressed on AML compared to normal hematopoietic stem cells.

Recent advances in the immunophenotyping of AML cells have revealed several AML associated cell surface antigens that may act as targets for future therapies [3]. Indeed, pre-clinical investigations using antibodies targeting CD44, CD47, T cell immunoglobulin mucin-3 (TIM-3) and the interleukin 3 receptor alpha chain (IL-3Rα; CD123) for the treatment of AML have been described and demonstrated promising anti-leukemic activity in murine models [3, 4]. CD123 is expressed on various malignancies including acute and chronic myeloid leukemia, hairy cell leukemia, B-cell lineage acute lymphoblastic leukemia, and blastic plasmacytoid dendritic cell neoplasms. Additionally, CD123 is not typically expressed on normal hematopoietic stem cells, thus making CD123 an ideal immunotherapeutic target. Additionally, two phase I trials for CD123-specific therapeutics have been completed with both drugs displaying good safety profiles (ClinicalTrials.gov ID: NCT00401739 and NCT00397579). Unfortunately, these CD123 targeting drugs had limited efficacy suggesting that alternative, and more potent therapies targeting CD123 may be required to observe anti-leukemic activity.

A possibly more potent alternative therapy for the treatment of AML is the use of T cells expressing chimeric antigen receptors (CARs) that redirect T cell specificity towards cell surface tumor associated antigens (TAAs) in an MHC-independent manner [5]. In most cases, CARs include a single-chain variable fragment (scFv) from a monoclonal antibody fused to the signaling domain of CD3ζ and may contain a costimulatory endodomain [5]. Several groups have developed CARs targeting various antigens for the treatment of B-cell malignancies [6-10] and many have gone on to evaluating CAR expressing T cells in phase I clinical trials [11-15]. In contrast, CAR engineered T cells for the treatment of AML remain scarce [16, 17].

Although current treatment regimes for AML can achieve complete responses in select patients, many will eventually relapse underscoring the need for novel therapeutics which may lead to more durable responses. Various AML targeting immunotherapies including antigen specific cytotoxic T lymphocytes, alloreactive natural killer cells, and dendritic cell vaccines are currently being developed. For example, Oka and colleagues have demonstrated that Wilms' Tumor 1 peptide vaccination can lead to clinical and immunological responses in AML patients [33]. However, these targeting therapies are HLA-dependent. To this end, it would be desirable to design a targeted therapeutic, such as a CAR, that can redirect T cell specificity to selectively target AML cells in an HLA-independent manner.

SUMMARY

A family of chimeric antigen receptors (CARs) containing a CD123 specific scFv was developed to target different epitopes on CD123. In some embodiments, such a CD123 chimeric antigen receptor (CD123CAR) gene includes an anti-CD123 scFv region fused in frame to a modified IgG4 hinge region comprising an alteration of an IgG4 spacer region that would eliminate Fc receptor binding. In one embodiment, the modified IgG4 hinge region includes an S228P substitution, an L235E substitution, and optionally an N297Q substitution. The CD123CAR gene also includes at least one costimulatory signaling domain; and a T cell receptor (TCR) zeta chain signaling domain. In some embodiments, the CD123CAR gene includes a nucleotide sequence selected from SEQ ID NO:1, SEQ ID NO:2, SEQ ID NO:3, or SEQ ID NO:4. In other embodiments, the CD123CAR gene encodes an amino acid sequence that includes SEQ ID NO:9; SEQ ID NO:10, SEQ ID NO:11, or SEQ ID NO:12.

According to the embodiments described below, the CD123CAR genes may be part of an expression cassette that is inserted within a vector (e.g., a viral vector). As such, a population of human T cells may be transduced by the vector, resulting the expression of the CD123CAR genes by the T cells. When expressed in healthy donor T cells (CD4/CD8), the CD123CARs redirect T cell specificity and mediated potent effector activity against CD123+ cell lines as well as primary AML patient samples. CD123CAR T cells did not significantly alter granulocyte/macrophage and erythroid colony formation in vitro, suggesting a differential effect on AML cells as opposed to immune cells.

Further, T cells obtained from patients with active AML can be modified to express CD123CAR genes and are able to lyse autologous AML blasts in vitro. These results suggest that CD123CAR-transduced T cells may be used as an immunotherapy for the treatment of high risk AML. Thus, according to some embodiments, methods of treating AML in a subject are provided, wherein such methods include a step of administering a first population of T cells transduced with a first CD123CAR gene to the subject. The methods may further comprise an additional step of administering the first population of T cells transfected with the first CD123CAR gene in combination with a second population of T cells transduced with a second CD123CAR gene to the subject. In some embodiments, the first CD123CAR gene include a nucleotide sequence selected from SEQ ID NO:3 or SEQ ID NO:4. The second CD123CAR gene may also include a nucleotide sequence selected from SEQ ID NO:3 or SEQ ID NO:4, however, the nucleotide sequence of the second CD123CAR gene may not the same as that selected for the first CD123CAR gene. This results in a combination treatment of AML using two or more different CD123CAR-transduced T cell populations, which may cause a synergistic effect when compared to using a single CD123CAR-transduced T cell population.

BRIEF DESCRIPTION OF THE DRAWINGS

FIG. 4 shows activation of multiple CD4 and CD8 effector functions by CD123 specific CARs following co-culture with primary AML samples. Pair-matched CAR engineered T cells were co-cultured for six hours with three different primary AML patient samples (AML 179, 373, and 605) and analyzed for surface CD107a expression and intracellular IFN-γ or TNF-α production. (A, bar graphs) Percentage of DAPI-CD3+ CD8+ EGFRt+ cells expressing CD107a. Data represents mean values+S.D. (A, pie charts). The fractions of CD3+ CD8+ EGFRt+ cells undergoing degranulation and producing IFN-γ and/or TNF-α are plotted in the pie charts. (B) DAPI-CD3+CD4+ EGFRt+ population data from the same experiment as described in A and B. (C) Pair-matched CFSE labeled CD19 or CD123-specific T cells were co-cultured with the indicated stimulator cells for 72 hours at an E:T of 2:1, and analyzed by flow cytometry for CFSE dilution in the DAPICD3+ EGFRt+ population. LCL and K562 cell lines serve as positive and negative 27 controls, respectively. Pre B-ALL 802 is a primary patient sample double positive for CD19 and CD123. Quadrant placement is based on unstimulated T cells.

FIG. 10 shows a schematic diagram of the 32716CAR construct having an L235E mutation and an S228P mutation ("32716CAR(S228P+L235E)") along with the nucleotide sequence of the 32716CAR(S228P+L235E) construct (SEQ ID NO:1—antisense strand (top numbered strand); SEQ ID NO:5—sense strand (bottom unnumbered strand)) and the amino acid sequence of the 32716CAR(S228P+L235E) construct (SEQ ID NO:9) according to some embodiments. Mutations are shown in bold.

FIG. 11 shows a schematic diagram of the 26292CAR construct having an L235E mutation and an S228P mutation ("26292CAR(S228P+L235E)") along with the nucleotide sequence of the 26292CAR(S228P+L235E) construct (SEQ ID NO:2—antisense strand (top numbered strand); SEQ ID NO:6—sense strand (bottom unnumbered strand)) and the amino acid sequence of the 26292CAR(S228P+L235E) construct (SEQ ID NO:10) according to some embodiments. Mutations are shown in bold.

FIG. 12 shows a schematic diagram of the 32716CAR construct having an L235E mutation, an S228P mutation and an N297Q mutation ("32716CAR(S228P+L235E+N297Q)") along with the nucleotide sequence of the 32716CAR(S228P+L235E+N297Q) construct (SEQ ID NO:3—antisense strand (top numbered strand); SEQ ID NO:7—sense strand (bottom unnumbered strand)) and the amino acid sequence of the 32716CAR(S228P+L235E+N297Q) construct (SEQ ID NO:11) according to some embodiments. Mutations are shown highlighted, in bold and underlined. IUPAC base code R corresponds to an A or G, and IUPAC base code Y corresponds to a T or C.

FIG. 13 shows a schematic diagram of the 26292CAR construct having an L235E mutation, an S228P mutation and an N297Q mutation ("26292CAR(S228P+L235E+N297Q)") along with the nucleotide sequence of the 26292CAR(S228P+L235E+N297Q) construct (SEQ ID NO:4—antisense strand (top numbered strand); SEQ ID NO:8—sense strand (bottom unnumbered strand)) and the amino acid sequence of the 26292CAR(S228P+L235E+N297Q) construct (SEQ ID NO:12) according to some embodiments. Mutations are shown in bold. IUPAC base code R corresponds to an A or G, and IUPAC base code Y corresponds to a T or C.

FIG. 14 shows CD123 expression on primary AML samples and cord blood. (A) Representative example of CD123 expression on primary AML cells. Cells were gated on the DAPI$^-$lineage$^-$CD34$^+$ population and assessed for CD123 expression (black—isotype control, red—anti-CD123). (B) Percentage of CD123 positive cells expressed in the DAPI$^-$lineage$^-$CD34$^+$ population. Each point represents an individual sample. (C) CD123 relative fluorescence index (RFI) in the DAPI$^-$lineage$^-$CD34$^{30}$ population. RFI is calculated by dividing the median of anti-CD123 cells by the median of isotype control stained cells. (D) Histogram overlay of CD123 expression on AML 605 (red), AML 722 (blue), and a cord blood sample (gray). Isotype control shown in black.

FIG. 16 shows CFSE that is diluted in both the CD4 and CD8 populations of CAR-expressing T cells. The CD4 (A) and CD8 (B) subpopulations of the cells shown in FIG. 5C are shown here. Following an initial gate on DAPI$^-$CD3$^+$ EGFRt$^+$ cells, CD4 and CD8 cells were analyzed for CFSE dilution following co-culture with primary AML patient samples. Quadrant placement is based on unstimulated T cells.

DETAILED DESCRIPTION

Certain embodiments of the invention are described in detail, using specific examples, sequences, and drawings. The enumerated embodiments are not intended to limit the invention to those embodiments, as the invention is intended to cover all alternatives, modifications, and equivalents, which may be included within the scope of the present invention as defined by the claims. One skilled in the art will recognize many methods and materials similar or equivalent to those described herein, which could be used in the practice of the present invention.

In some embodiments, a gene encoding a tumor targeting chimeric antigen receptor (CAR) is provided. According to certain embodiments, the gene encodes a CD123-specific CAR (CD123CAR). A CD123CAR gene includes an anti-CD123 single-chain Fv (scFv) region and one or more of the following domains: a hinge region, a costimulatory signaling domain, an intracellular signaling domain, or a combination thereof.

In some embodiments, a CD123CAR gene may include, but is not limited to, an anti-CD123 single-chain Fv (scFv) region, a hinge region, optionally, at least one costimulatory signaling domain, and optionally, an intracellular signaling domain.

Figure 9:
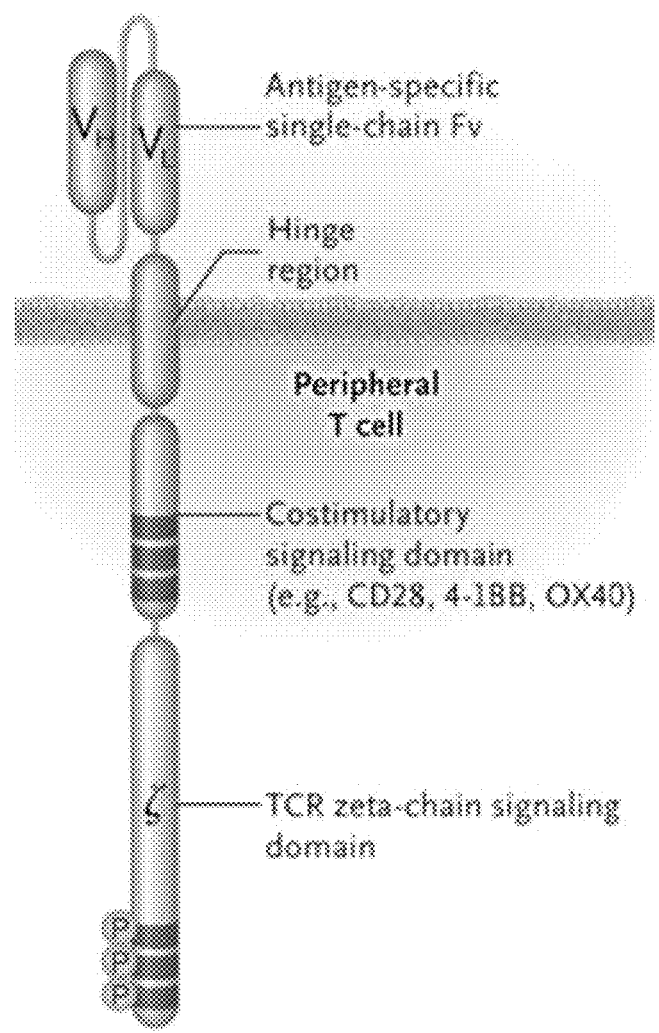
FIG. 9 shows a schematic diagram of a chimeric antigen receptor (CAR) having an antigen-specific single-chain Fv, a hinge region, a costimulatory signaling domain, and T cell Receptor zeta-chain signaling domain in accordance with some embodiments. (Image from Urba W J and Longo D L N Engl J Med 2011; 365:754-757).

In certain embodiments, a CD123CAR gene may include, but is not limited to, an anti-CD123 single-chain Fv (scFv) region, a hinge region, at least one costimulatory signaling domain, and an intracellular signaling domain (FIG. 9).

The anti-CD123 scFv region may include a nucleotide sequence that, when expressed, may bind an epitope of CD123. In some embodiments, the scFv anti-CD123 scFv region includes a nucleotide which encodes a VH and a VL domain of recombinant immunotoxins (RITs) 26292 and 32716 [18]. A CD123CAR gene that targets 26292 and a CD123CAR gene that targets 32716 is also referred to herein as a 26292CAR and a 32716CAR, respectively. In certain embodiments, an anti-CD123 scFv region may include a nucleotide sequence selected from the following:

nucleotides 82-814 of SEQ ID NO:1 or SEQ ID NO:3 for a 32716CAR nucleotides 82-792 of SEQ ID NO:2 or SEQ ID NO:4 for a 26292CAR; or Said nucleotide sequences encode amino acid sequences selected from the following:

residues 23-266 of SEQ ID NO:9 or SEQ ID NO:11 when used in a 32716CAR; or residues 23-259 of SEQ ID NO:10 or SEQ ID NO:12 when used in a 26292CAR.

In certain embodiments, the anti-CD123 scFv region may be modified to enhance binding or to reduce immunogenicity. For example, in one aspect, the anti-CD123 scFv region may be a humanized anti-CD123 scFv region.

The hinge region may include at least a portion of an immunoglobulin (e.g., IgG1, IgG2, IgG3, IgG4) that falls between the CH2-CH3 domains. In some embodiments, the hinge regions is a modified hinge. The modified hinge may have one or more amino acid substitutions or modifications that contribute to reducing the CD123CAR's off-target effects, thereby increasing its specificity and efficacy. An "amino acid modification" or an "amino acid substitution" or a "substitution," as used herein, mean an amino acid substitution, insertion, and/or deletion in a protein or peptide sequence. An "amino acid substitution" or "substitution" as used herein, means a replacement of an amino acid at a particular position in a parent peptide or protein sequence with another amino acid. For example, the substitution S228P refers to a variant protein or peptide, in which the serine at position 228 is replaced with proline.

Amino acid substitutions can be made by mutation such that a particular codon in the nucleic acid sequence encoding the protein or peptide is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein.

The following are examples of various groupings of amino acids:

Amino acids with nonpolar R groups: Alanine, Valine, Leucine, Isoleucine, Proline, Phenylalanine, Tryptophan, Methionine Amino acids with uncharged polar R groups: Glycine, Serine, Threonine, Cysteine, Tyrosine, Asparagine, Glutamine Amino acids with charged polar R groups (negatively charged at Ph 6.0): Aspartic acid, Glutamic acid Basic amino acids (positively charged at pH 6.0): Lysine, Arginine, Histidine (at pH 6.0)

Another grouping may be those amino acids with phenyl groups: Phenylalanine, Tryptophan, Tyrosine.

Another grouping may be according to molecular weight (i.e., size of R groups) as shown below:

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

In certain embodiments, the modified hinge is derived from an IgG1, IgG2, IgG3, or IgG4 that includes one or more amino acid residues substituted with an amino acid residue different from that present in an unmodified hinge. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified hinge is derived from an IgG1, IgG2, IgG3, or IgG4 that includes, but is not limited to, one or more of the following amino acid residue substitutions: C220S, C226S, S228P, C229S, P230S, E233P, V234A, L234V, L234F, L234A, L235A, L235E, G236A, G237A, P238S, S239D, F243L, P247I, S267E, H268Q, S280H, K290S, K290E, K290N, R292P, N297A, N297Q, S298A, S298G, S298D, S298V, T299A, Y300L, V305I, V309L, E318A, K326A, K326W, K326E, L328F, A330L, A330S, A331S, P331S, I332E, E333A, E333S, E333S, K334A, A339D, A339Q, P396L, or a combination thereof (50).

In some embodiments, the modified hinge is derived from an IgG4 hinge having the following amino acid sequence:

```
                                         (SEQ ID NO: 13)
Pos. 219
ESKYGPPCPS CPAPEFLGGP SVFLFPPKPK DTLMISRTPE

VTCVVVDVSQ EDPEVQFNWY

Pos. 279
VDGVEVHNAK TKPREEQFNS TYRVVSVLTV LHQDWLNGKE

YKCKVSNKGL PSSIEKTISK

Pos. 339
AKGQPREPQV YTLPPSQEEM TKNQVSLTCL VKGFYPSDIA

VEWESNGQPE NNYKTTPPVL

Pos. 399
DSDGSFFLYS RLTVDKSRWQ EGNVFSCSVM HEALHNHYTQ

KSLSLSLGK
```

In certain embodiments, the modified hinge is derived from IgG4 that includes one or more amino acid residues substituted with an amino acid residue different from that present in an unmodified hinge. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified hinge is derived from an IgG4 that includes, but is not limited to, one or more of the following amino acid residue substitutions: 220S, 226S, 228P, 229S, 230S, 233P, 234A, 234V, 234F, 234A, 235A, 235E, 236A, 237A, 238S, 239D, 243L, 247I, 267E, 268Q, 280H, 290S, 290E, 290N, 292P, 297A, 297Q, 298A, 298G, 298D, 298V, 299A, 300L, 305I, 309L, 318A, 326A, 326W, 326E, 328F, 330L, 330S, 331S, 331S, 332E, 333A, 333S, 333S, 334A, 339D, 339Q, 396L, or a combination thereof, wherein the amino acid in the unmodified hinge is substituted with the above identified amino acids at the indicated position.

In some embodiments, the modified IgG4 hinge includes, but is not limited to, a substitution of proline (P) in place of serine (S) at position 228 (S228P), a substitution of leucine (L) in place of glutamic acid (E) at position 235 (L235E), a substitution of asparagine (N) in place of glutamine (Q) at position 297 (N297Q). In certain embodiments, a modified IgG4 hinge region may include a nucleotide sequence selected from the following:

nucleotides 814-1500 of SEQ ID NO:1 or SEQ ID NO:3 for a 32716CAR; or nucleotides 793-1479 of SEQ ID NO:2 or SEQ ID NO:4 for a 26292CAR.

Said nucleotide sequences encode amino acid sequences selected from the following:

residues 267-495 of SEQ ID NO:1 or SEQ ID NO:3 when used in a 32716CAR; or residues 260-488 of SEQ ID NO:2 or SEQ ID NO:4 when used in a 26292CAR.

In one embodiment, the modified IgG4 hinge region includes an S228P substitution and an L235E substitution ("S228P+L235E") (See FIGS. 10 and 11). In another embodiment, the modified IgG4 hinge region includes an S228P substitution, an L235E substitution, and an N297Q substitution ("S228P+L235E+N297Q") (See FIGS. 12 and 13).

In some embodiments, the hinge may be modified to substitute the Fc spacer region in the C123CAR for a spacer that has no Fc binding, such as the hinge region of CD8a. Alternatively, the Fc spacer region of the hinge may be deleted. Such substitutions would reduce or eliminate Fc binding.

The term "position," as used herein, is a location in the sequence of a protein. Positions may be numbered sequentially, or according to an established format, for example a Kabat position or an EU position or EU index as in Kabat. For all positions discussed herein, numbering is according to the EU index or EU numbering scheme (Kabat et al., 1991, Sequences of *Proteins of Immunological Interest*, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al., 1969, Proc Natl Acad Sci USA 63:78-85, which is hereby entirely incorporated by reference). Kabat positions, while also well known in the art, may vary from the EU position for a given position. For example, the S228P and L235E substitutions described above refer to the EU position. However, these substitutions may also correspond to Kabat positions 241 (S241P) and 248 (L248E) [21].

The costimulatory signaling domain may include any suitable costimulatory domain including, but not limited to a 4-1BB costimulatory domain, an OX-40 costimulatory domain, a CD27 costimulatory domain, or a CD28 costimulatory domain. According to the embodiments described herein, a CD123CAR may include at least one costimulatory signaling domain. In one aspect the CD123CAR has a single costimulatory signaling domain, or it may include two or more costimulatory signaling domains such as those described above. In another aspect, the costimulatory domain may be made up of a single costimulatory domain such as those described above, or alternatively, may be made up of two or more portions of two or more costimulatory domains. Alternatively, in some embodiments, the CD123CAR does not include a costimulatory signaling domain.

In one embodiment, the CD123CAR includes a costimulatory signaling domain which is a CD28 costimulatory domain. The CD28 signaling domain may include a modified CD28 transmembrane domain. In one embodiment, such a modified CD28 transmembrane domain has one or more amino acid substitutions or modifications including, but not limited to a substitution of leucine-leucine (LL) to glycine-glycine (GG) at amino acid residues 530-531 of SEQ ID NO:10 or SEQ ID NO:12; or residues 523-524 of SEQ ID NO:11 or SEQ ID NO:13 (e.g., RLLH→RGGH [22]). In certain embodiments, a modified costimulatory signaling domain region may include a nucleotide sequence selected from the following:

nucleotides 1501-1707 of SEQ ID NO:1 or SEQ ID NO:3 for a 32716CAR; or nucleotides 1480-1686 of SEQ ID NO:2 or SEQ ID NO:4 for a 26292CAR.

Said nucleotide sequences encode amino acid sequences selected from the following:

residues 498-564 of SEQ ID NO:1 or SEQ ID NO:3 when used in a 32716CAR; or.

residues 489-557 of SEQ ID NO:2 or SEQ ID NO:4 when used in a 26292CAR.

The intracellular signaling domain may include any suitable T cell receptor (TCR) complex, signaling domain portion thereof. In some embodiments, the intracellular signaling domain is a TCR zeta-chain (ζ-chain) signaling domain. In certain embodiments, a ζ-chain signaling domain may include a nucleotide sequence selected from the following:

nucleotides 1717-2052 of SEQ ID NO:1 or SEQ ID NO:3 for a 32716CAR; or.

nucleotides 1696-2031 of SEQ ID NO:2 or SEQ ID NO:4 for a 26292CAR.

Said nucleotide sequences encode amino acid sequences selected from the following:

residues 568-679 of SEQ ID NO:1 or SEQ ID NO:3 when used in a 32716CAR;

residues 561-672 of SEQ ID NO:2 or SEQ ID NO:4 when used in a 26292CAR.

Therefore, in accordance with the embodiments described above, the CD123CAR gene may include a nucleotide sequence selected from SEQ ID NO:1, SEQ ID NO:2, SEQ ID NO:3 or SEQ ID NO:4. In other embodiments, the CD123CAR gene may encode an amino acid sequence selected from SEQ ID NO:9, SEQ ID NO:10, SEQ ID NO:11 or SEQ ID NO:12. (FIGS. 10, 11, 12, 13).

Expression of CD123CAR Genes and Transduction of T Cells

In some embodiments, the CD123CAR gene is part of an expression cassette. In some embodiments, the expression cassette may—in addition to the CD123CAR gene—also include an accessory gene. When expressed by a T cell, the accessory gene may serve as a transduced T cell selection marker, an in vivo tracking marker, or a suicide gene for transduced T cells.

In some embodiments, the accessory gene is a truncated EGFR gene (EGFRt). An EGFRt may be used as a non-immunogenic selection tool (e.g., immunomagnetic selection using biotinylated cetuximab in combination with anti-biotin microbeads for enrichment of T cells that have been lentivirally transduced with EGFRt-containing constructs), tracking marker (e.g., flow cytometric analysis for tracking T cell engraftment), and suicide gene (e.g., via Cetuximab/Erbitux® mediated antibody dependent cellular cytotoxicity (ADCC) pathways). An example of a truncated EGFR (EGFRt) gene that may be used in accordance with the embodiments described herein is described in International Application No. PCT/US2010/055329, the subject matter of which is hereby incorporated by reference as if fully set forth herein. In other embodiments, the accessory gene is a truncated CD19 gene (CD19t).

In another embodiment, the accessory gene is an inducible suicide gene. A suicide gene is a recombinant gene that will cause the cell that the gene is expressed in to undergo programmed cell death or antibody mediated clearance at a desired time. In one embodiment, an inducible suicide gene that may be used as an accessory gene is an inducible caspase 9 gene (see Straathof et al. (2005) An inducible caspase 9 safety switch for T-cell therapy. *Blood*. June 1; 105(11): 4247-4254, the subject matter of which is hereby incorporated by reference as if fully set forth herein).

In some embodiments, the expression cassette that include a CD123CAR gene described above may be inserted into a vector for delivery—via transduction or transfection—of a target cell. Any suitable vector may be used, for example, a bacterial vector, a viral vector, or a plasmid. In some embodiments, the vector is a viral vector selected from a retroviral vector, a lentiviral vector, a poxvirus vector, an adenoviral vector, or an adeno-associated viral vector In some embodiments, the vector may transduce a population of healthy T cells. Successfully transduced or transfected target cells express the one or more genes that are part of the expression cassette.

As such, one or more populations of T cells may be transduced with a CD123CAR gene. In some embodiments, the CD123CAR gene includes a nucleotide sequence selected from SEQ ID NO:1, SEQ ID NO:2, SEQ ID NO:3 or SEQ ID NO:4. Accordingly, in some embodiments, the transduced T cells express a CD123CAR gene that encodes an amino acid sequence selected from SEQ ID NO:9, SEQ ID NO:10, SEQ ID NO:11 or SEQ ID NO:12. (FIGS. 10, 11, 12, 13). The transduced T cells may be from a donor, or may be from a subject having AML and who is in need of a treatment for AML. In some embodiments, the transduced T cells are used in an adoptive immunotherapy treatment for the treatment of AML Further, the one or more populations of T cells may be part of a pharmaceutically acceptable composition for delivery for administration to a subject. In addition to the CD123CAR-transduced T cells, the pharmaceutically effective composition may include one or more pharmaceutically effective carriers. A "pharmaceutically acceptable carrier" as used herein refers to a pharmaceutically acceptable material, composition, or vehicle that is involved in carrying or transporting a treatment of interest from one tissue, organ, or portion of the body to another tissue, organ, or portion of the body. Such a carrier may comprise, for example, a liquid, solid, or semi-solid filler, solvent, surfactant, diluent, excipient, adjuvant, binder, buffer, dissolution aid, solvent, encapsulating material, sequestering agent, dispersing agent, preservative, lubricant, disintegrant, thickener, emulsifier, antimicrobial agent, antioxidant, stabilizing agent, coloring agent, or some combination thereof.

Each component of the carrier is "pharmaceutically acceptable" in that it must be compatible with the other ingredients of the composition and must be suitable for contact with any tissue, organ, or portion of the body that it may encounter, meaning that it must not carry a risk of toxicity, irritation, allergic response, immunogenicity, or any other complication that excessively outweighs its therapeutic benefits.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) natural polymers such as gelatin, collagen, fibrin, fibrinogen, laminin, decorin, hyaluronan, alginate and chitosan; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as trimethylene carbonate, ethyl oleate and ethyl laurate; (13) agar; (14) buffering agents, such as magnesium hydroxide and aluminum hydroxide; (15) alginic acid (or alginate); (16) pyrogen-free water; (17) isotonic saline; (18) Ringer's solution; (19) alcohol, such as ethyl alcohol and propane alcohol; (20) phosphate buffer solutions; (21) thermoplastics, such as polylactic acid, polyglycolic acid, (22) polyesters, such as polycaprolactone; (23) self-assembling peptides; and (24) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of CD123CAR-transduced T cells in these formulations can vary widely, and will be selected primarily based on fluid volumes, viscosities, organ size, body weight and the like in accordance with the particular mode of administration selected and the biological system's needs.

In certain embodiments, populations of T cells transduced with a CD124CAR gene (i.e., CD124CAR-transduced T cells) such as those described herein cells used in the methods for targeting and killing AML cells may be grown in a cell culture. In certain aspects of this embodiment, the method may be used in an in vitro or research setting to investigate the role of CD123 in the etiology of AML, or to evaluate the targeting abilities of new CD123CAR constructs.

Treatment of AML with CD123CAR-Transduced T Cells

Figure 8:
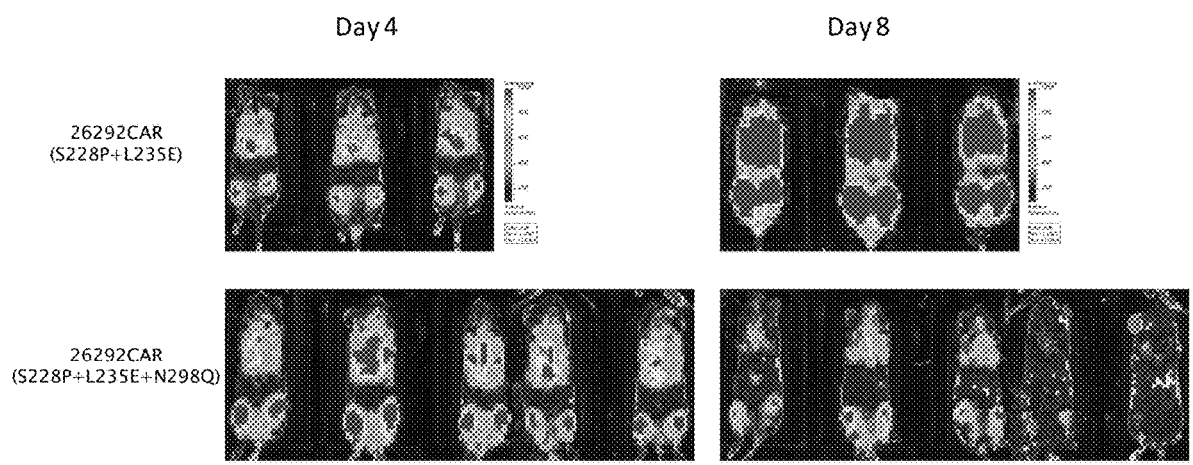
FIG. 8 shows changes in tumor size as shown by bioluminescent imaging of NSG mice that were treated five days after injection of the AML cell line KG1a modified to express firefly luciferase (day 5) with CD123CAR-transduced T cells (26292) containing either the S228P+L235E mutations or the S228P+L235E+N297Q mutations.

According to some embodiments, CD123CAR genes and populations of T cells that are transduced with CD123CAR genes such as those described above may be used in methods for treating AML in a subject. Such methods may include a step of administering a therapeutically effective amount of at least one population of T cells transduced with at least one CD123CAR gene to the subject. In these embodiments, the population of CD123CAR-transduced T-cells express one or more CD123CAR genes, such as those described above. In certain embodiments, the T cells are transduced with and express a 32716CAR(S228P+L235E+N297Q) gene construct (FIG. 12) or a 26292CAR(S228P+L235E+N297Q) gene construct (FIG. 13). When such cells are administered via an adoptive immunotherapy treatment, the transduced T cells specifically target and lyse CD123 expressing cells (i.e., AML cells) in vivo, thereby delivering their therapeutic effect of eliminating cancer cells. As described in the Examples below, CD123CAR gene constructs having the S228P and L235E mutations in the hinge range provides sufficient protection from off-target effects to generate a sufficient response in cultured cells in vitro. However, this data should not be extrapolated to these constructs' effect in vivo. Researchers often give great deference to in vitro data with respect to its transferability of a treatment's effect to in vivo data. Sometimes, in vitro data does coincide with in vivo data. However, this correlation is unpredictable, because as FIG. 8 shows, CD123CAR(S228P+L235E) gene constructs (FIGS. 10-11) which showed a highly effective anti-tumor cell effect in vitro did not have the same effects in vivo. Consequently, an additional mutation was made in the hinge region (N297Q) to generate CD123CAR(S228P+ L235E+N297Q) constructs. In contrast to the CD123CAR (S228P+L235E) gene constructs administration of these constructs resulted in significant reduction of leukemic burden.

The population or populations of T cells transduced with the CD123CAR gene or genes that may be used in accordance with the methods described herein may be administered, by any suitable route of administration, alone or as part of a pharmaceutical composition. A route of administration may refer to any administration pathway known in the art, including but not limited to intracranial, parenteral, or transdermal. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intratumoral, intrauterine, intravenous, subarachnoid, subcapsular, subcutaneous, transmucosal, or transtracheal. In certain embodiments, transduced T cells are administered intravenously or intrathecally.

The term "effective amount" as used herein refers to an amount of an agent, compound, treatment or therapy that produces a desired effect. For example, a population of cells may be contacted with an effective amount of an agent, compound, treatment or therapy to study its effect in vitro (e.g., cell culture) or to produce a desired therapeutic effect ex vivo or in vitro. An effective amount of an agent, compound, treatment or therapy may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a compound and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, PA, 2005, which is hereby incorporated by reference as if fully set forth herein. Agents, compounds treatments or therapies that may be used in an effective amount or therapeutically effective amount to produce a desired effect in accordance with the embodiments described herein may include, but are not limited to, a CD123CAR gene, an expression cassette that includes a CD123CAR gene, a vector that delivers an expression cassette that includes a CD123CAR gene to a target cell such as a T cell, and a population of T cells that are transduced with a CD123CAR gene.

The terms "treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition.

The term "subject" as used herein refers to a human or animal, including all mammals such as primates (particularly higher primates), sheep, dog, rodents (e.g., mouse or rat), guinea pig, goat, pig, cat, rabbit, and cow. In some embodiments, the subject is a human.

In certain embodiments, the methods for treating AML may include a step of administering a therapeutically effective amount of a first population of T cells transduced with a first CD123CAR gene in combination with a therapeutically effective amount of a second population of T cells transduced with a second CD123CAR gene.

In other embodiments, CD123CAR-transduced T cells may be administered in combination with one or more additional anti-cancer therapies. "In combination" or "in combination with," as used herein, means in the course of treating the same cancer in the same subject using two or more agents, drugs, therapeutics, procedures, treatment regimens, treatment modalities or a combination thereof, in any order. This includes simultaneous administration, as well as in a temporally spaced order of up to several days apart. Such combination treatment may also include more than a single administration of any one or more of the agents, drugs, therapeutics, procedures, treatment regimens, and treatment modalities. Further, the administration of the two or more agents, drugs, therapeutics, procedures, treatment regimens, treatment modalities or a combination thereof may be by the same or different routes of administration.

Additional anti-cancer therapies that may be used in accordance with the methods described herein may include one or more anti-cancer procedures, treatment modalities, anti-cancer therapeutics or a combination thereof. In some embodiments, the CD123CAR-transduced T cells may be administered in combination with one or more anti-cancer procedures or treatment modalities including, but not limited to, stem cell transplantation (e.g., bone marrow transplant or peripheral blood stem cell transplant using allogenic stem cells, autologous stem cells; or a non-myeloablative transplant), radiation therapy, or surgical resection. In other embodiments, the CD123CAR-transduced T cells may be administered in combination with one or more anti-cancer therapeutics or drugs that may be used to treat AML including, but not limited to, chemotherapeutics and other anti-cancer drugs, immunotherapeutics, targeted therapeutics, or a combination thereof.

Chemotherapeutics and other anti-cancer drugs that may be administered in combination with the CD123CAR-transduced T cells in accordance with the embodiments described herein include, but are not limited to, all-trans-retinoic acid (ATRA), arsenic trioxide, anthracycline antibiotics and pharmaceutically acceptable salts thereof (e.g., doxorubicin hydrochloride, daunorubicin hydrochloride, idarubicin, mitoxantrone), alkylating agents (e.g., cyclophosphamide, laromustine), antimetabolite analogs (cytarabine, 6-thioguanine, 6-mercaptopurine, methotrexate), demethylating agents (e.g., decitabine, 5-azacytidine), nucleic acid synthesis inhibitors (e.g., hydroxyurea), topoisomerase inhibitors (e.g., etoposide), vinca alkaloids (e.g., vincristine sulfate), or a combination thereof (e.g., "ADE," which is a combination treatment that includes a combination of Cytarabine (Ara-C), Daunorubicin Hydrochloride and Etoposide).

Immunotherapeutics that may be administered in combination with the CD123CAR-transduced T cells in accordance with the embodiments described herein include, but are not limited to, immune modulatory reagents (e.g., STAT3 inhibitors, Lenalidomide) and therapeutic monoclonal antibodies. The therapeutic monoclonal antibodies may be designed (i) to target one or more AML antigens including, but not limited to, CD33 (e.g., gemtuzumab, lintuzumab), MUC1 (e.g., cantuzumab ravtansine, clivatuzumab tetraxetan, pemtumomab); (i) a B cell antigen (e.g., rituximab, ofatumumab); or a vasculature modulator such as VEGF or VEGFR (e.g., alacizumab pegol, bevacizumab, icrucumab, ramucirumab, ranibizumab).

Targeted therapeutics that may be administered in combination with the CD123CAR-transduced T cells in accordance with the embodiments described herein include, but are not limited to, tyrosine kinase inhibitors (imatinib, dasatinib, nilotinib, sunitinib), farnesyl transferase inhibitors (e.g., tipifarnib), FLT inhibitors, and c-Kit (or CD117) inhibitors (imatinib, dasatinib, nilotinib).

Example 1: CD123Car-Transduced T Cells Exhibit Potent Cytolytic Activity and Multiple Effector Functions Against AML In Vitro Materials and Methods Cell lines. Unless stated otherwise, all cell lines were maintained in RPMI 1640 (Irvine Scientific) supplemented with 2 mM L-glutamine, 25 mM HEPES, and 10% heat-inactivated FCS (Hyclone), hereafter referred to as complete media (CM). Peripheral blood mononuclear cells (PBMCs) were transformed with Epstein-Barr virus to generate lymphoblastoid cell lines (LCL) as previously described [19]. LCL-OKT3 cells express membrane bound OKT3 and are grown in CM supplemented with 0.4 mg/ml hygromycin [20]. K562 cells were obtained from ATCC and cultured as recommended. KG1a cells (kindly provided by Dr. Ravi Bhatia) were maintained in IMDM (Irvine Scientific) with 25 mM HEPES, 4 mM L-glutamine (Irvine Scientific), and 20% FCS. 293T cells (a kind gift from the Center for Biomedicine and Genetics at City of Hope) were maintained in DMEM+10% heat inactivated FCS.

Primary AML samples. Primary AML samples were obtained from peripheral blood of patients (referred to herein as AML Sample ID Nos. 179. 373, 493, 519, 545, 559, 605, 722 and 813). The characteristics of the samples are summarized in Table 1 below.

[Table 1 is on following page]

TABLE 1

Characteristics of primary AML samples.

| AML Sample ID | Age/Sex | Cytogenetics | Flt3 Mutational Status | Clinical Status | Sample Type | CD123 (RFI)$^a$ | CD123 % positive |
|---|---|---|---|---|---|---|---|
| 179 | 74/M | Intermediate-risk t(1; 7), t(14; 15) | ND | Relapsed | PB | 428.32 | 99.22 |
| 373 | 47/M | Poor-risk Complex abnormalities in 3 cell lines | ND | Relapsed | PB | 1052.83 | 99.66 |
| 493 | 46/F | Intermediate-risk Trisomy 8 | ND | Relapsed | PB | 23.98 | 76.80 |
| 519 | 44/F | del(17p), dic (11; 7), clonal loss of TP53/17p13.1 | ND | Relapsed | PB | 63.18 | 97.40 |
| 545 | 58/M | Intermediate-risk t(3; 6), del(7) | ND | Induction failure | PB | 52.73 | 99.32 |
| 559 | 59/M | Complex abnormalities, Massive hyperdiploidy | Negative | Relapsed | Apheresis | 9.30 | 45.0 |

TABLE 1-continued

Characteristics of primary AML samples.

| AML Sample ID | Age/Sex | Cytogenetics | Flt3 Mutational Status | Clinical Status | Sample Type | CD123 (RFI)[a] | CD123 % positive |
|---|---|---|---|---|---|---|---|
| 605 | 55/M | Normal | Negative | Persistent | PB | 58.48 | 99.91 |
| 722 | 22/M | Intermediate risk t(14; 21), del(9q) | Negative | Untreated | PB | 33.53 | 92.74 |
| 813 | 48/F | Complex abnormalities, Trisomy 8, Trisomy 21, add(17) | ND | Untreated | PB | 37.19 | 90.93 |

[a]Relative Fluorescence Index (RFI) is the ratio of the median of the 9F5-stained signal to isotype matched control stain in the CD34+ population
[b]Gated on CD34+ population
ND—not determined
PB—peripheral blood Flow Cytometry. Fluorochrome conjugated isotype controls, anti-CD4, anti-CD8, anti-T-cell receptor-αβ (TCRαβ), anti-CD123 (9F5), anti-CD34 (8G12), and anti-CD38 (HIT2) were purchased from BD Biosciences. Biotinylated anti-Fc was purchased from Jackson ImmunoResearch Laboratories. Biotinylated cetuximab (Erbitux) was purchased from the COH pharmacy and has been previously described [20]. Biotinylated anti-CD2, anti-CD3, anti-CD7, anti-CD10, anti-CD11b, anti-CD19, anti-CD33, and ant-CD235A were purchased from eBioscience. Data acquisition was performed on a FACSCalibur, LSRII (BD Biosciences), or MACSQuant Analyzer (Miltenyi Biotec) and analyzed using FCS Express, Version 3 (De Novo Software).

Transfection of 293T cells with CD123. CD123 cDNA was amplified from CD123-pMD18-T (Sino Biological Inc.) using polymerase chain reaction and primers (CD123-F: 5'-ATAAGGCCTGCCGCCAC-CATGGTCCTCCTTTGGCTCACG-3' and CD123-R 5'-ATAGCTAGCT-CAAGTTTTCTGCACGACCTGTACTTC-3'). The PCR product was cloned into pMGPac using StuI and NheI restriction sites. 293T cells were transfected using Lipofectamine 2000 (Life Technologies) per manufacturer's instructions. 24 hours post-transfection, expression of CD123 was confirmed by flow cytometry Generation of Lentiviral vectors. To generate the CAR constructs used in this study, codon optimized DNA sequences encoding for the VH and VL chains, a modified IgG4 hinge and a modified CD28 transmembrane domain (RLLH→RGGH [22]) were synthesized (GENEART) and cloned into CD19RCAR-T2AEGFRt_epHIV7 [20] using NheI and RsrII sites to replace the CD19RCAR. Lentivirus was produced by transfecting 293T cells with a lentivrial vector and the packaging vectors pCMV-Rev2, pCHGP-2, and pCMV-G using CalPhos™ mammalian cell transfection kit (Clontech). These 26292 and 32716 CAR constructs are also referred to herein as 26292CAR(S228P+L235E) or 26292CAR(S228P+L235EN297Q) (FIGS. 11 and 13) and 32716CAR(S228P+L235E) or 32716CAR(S228P+L235E+N297Q) (FIGS. 10 and 12). Lentiviral supernatants were collected at 24, 48, and 72 hours post-transfection and concentrated by ultracentrifugation.

Transduction of healthy donor and AML Patient PBMCs. Deidentified PBMCs were obtained from consented healthy donors and patients under institutional review board approved protocols. For healthy donors, T cells were activated using OKT3 (30 ng/ml) in CM supplemented 3 times a week with 25 U/ml IL-2 and 0.5 ng/ml IL-15 (herein referred to as T cell media). 72 hours post-activation, T cells were spinoculated with lentivirus at MOI=3 by centrifuging for 30 minutes at 800 g and 32° C. CAR expression was analyzed by flow cytometry 12-14 days post lentiviral transduction. EGFRt expressing T cells were enriched as previously described [20]. T cells were expanded in T cell media by rapid expansion method [23].

For genetic modification of T cells from AML patients, thawed peripheral blood or apheresis product were stimulated using Dynabeads® Human T-Expander CD3/CD28 (Life Technologies) at a 3:1 bead:CD3+ cell ratio in T cell media. 72 hours post-bead stimulation, cells were spinoculated with lentivirus at a MOI=3. Beads were removed 9-14 days after initial stimulation using a DynaMag™-50 magnet (Life Technologies) and T cells were maintained in T cell media. CAR-expressing AML patient derived T cell lines were not immunomagnetically selected prior to use in killing assays.

CFSE proliferation assay. T cells were labeled with 0.5 µM carboxyfluoroscein succinimidyl ester (CFSE; Molecular Probes) per manufacturer's instructions. Labeled T cells were cocultured with, or without, stimulator cells at an E:T ratio of 2:1 in CM supplemented with 10 U/ml IL-2. After 72-96 hours, cells were harvested and stained with biotinylated cetuximab as well as propidium iodide or DAPI to exclude dead cells from analysis. Samples were analyzed by flow cytometry to evaluate proliferation of live EGFRt-positive cells by CFSE dilution.

Chromium-release assay and cytokine secretion assay. Target cells were labeled for 1 hour with 51Cr (PerkinElmer), washed five times, and aliquoted in triplicate at 5×103 cells/well with effector cells at various effector to target (E:T) ratios. Following a 4 hour co-culture, supernatants were harvested and radioactivity was measured using a gamma counter or a Topcount (PerkinElmer). Percent-specific lysis was calculated as previously described [24]. Cytokine production following a 24 hour co-culture at a 10:1 E:T ratio was measured as previously described [25].

CD107a degranulation and intracellular cytokine production. T cells were cocultured with target cells at an E:T of 2:1 for six hours at 37° C. in the presence of GolgiStop™ (BD Biosciences) and anti-CD107a clone H4A3 or isotype matched control antibody. At the completion of the six hour incubation, cells were harvested, washed and stained with anti-CD3, CD4, CD8, and biotinylated cetuximab followed by a secondary stain using PE-conjugated streptavidin. Cells were then fixed and permeabilized (Cytofix/Cytoperm™ BD Biosciences) per manufacturer's instructions and stained with anti-IFN-_ (BD Biosciences clone B27) and anti-TNF-α (BD Biosciences clone MAb11). Data acquisition was performed using MACSQuant analyzer (Miltenyi Biotec) and analysis was done using FCS Express Version 3 (De Novo Software).

Colony Forming Cell Assay. CD34+ cells from cord blood (CB) mononuclear cells or primary AML samples were selected using immunomagnetic column separation (Miltenyi Biotech). 103 CD34+ CB cells were cocultured with 25×103 effector cells for 4 hours prior to plating in semisolid methylcellulose progenitor culture in duplicate wells [26]. 14 to 18 days later, colonyforming unit granulocyte-macrophage (CFU-GM) and burst-forming unit erythroid (BFUE) colonies were enumerated. For AML samples, 5×103 CD34+ AML cells were cocultured with 125×103 effector cells for 4 hours prior to plating in semisolid methylcellulose progenitor culture in duplicate wells.

Statistics analysis. Statistical analyses were performed using Graphpad Prism v5.04. Unpaired Student's t-test were used to identify significant differences between treatment groups.

Results

Generation of CD123 CAR Expression T Cells

Figure 1:
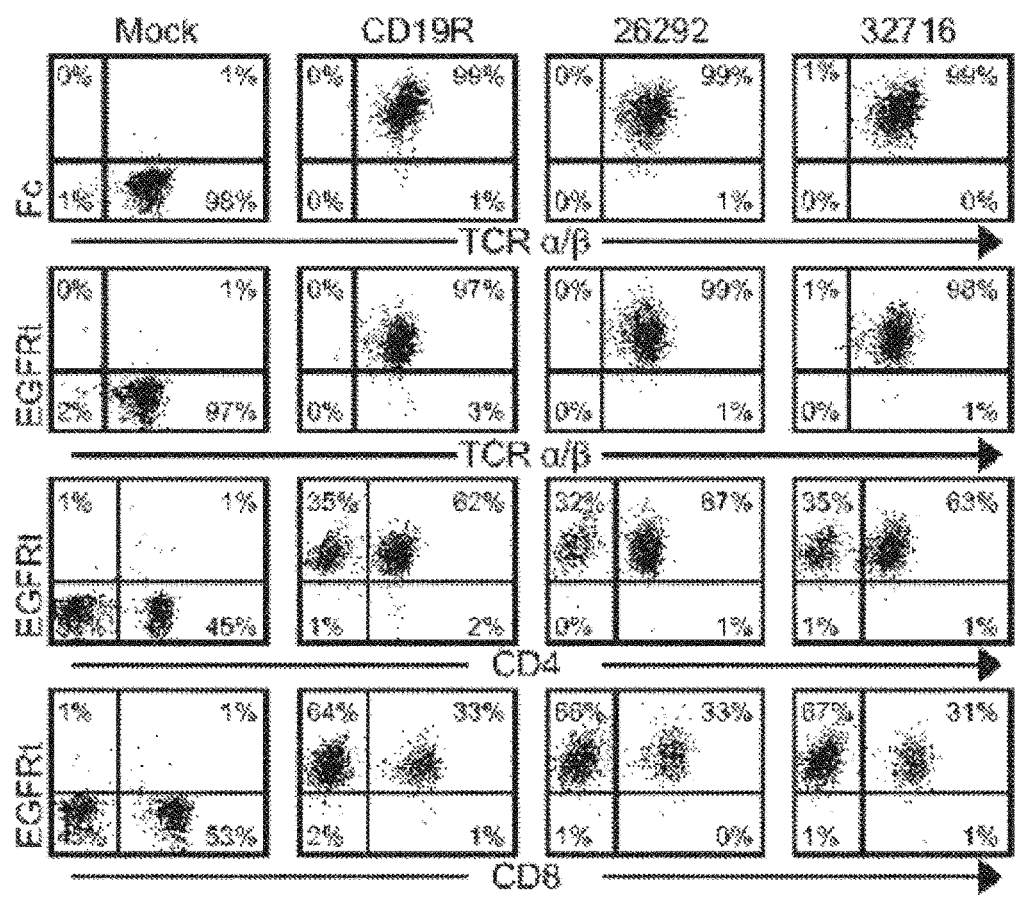
FIG. 1 shows that CD123-specific CARs can be expressed in healthy donor human T cells. (A) Schematic diagram of the CAR containing a modified IgG4 hinge, a modified transmembrane and intracellular signaling domain of CD28, and the CD3ζ signaling domain. The T2A ribosomal skip sequence and the truncated EGFR (EGFRt) transduction marker are also indicated. (B) Representative phenotype of mock and lenti-transduced T cells derived from a single healthy donor. After immunomagnetic selection and one cycle of expansion, CAR modified T cells were stained with biotinylated anti-Fc or biotinylated anti-EGFR followed by PE-conjugated streptavidin and anti-TCRα/β, anti-CD4, or anti-CD8 and analyzed by flow cytometry. Quadrant placement is based on staining with isotype controls, and the percentage of cells falling in each quadrant is indicated. (C) Expression of indicated cell surface markers from three different health donor T cell lines following immunomagnetic selection and one cycle of expansion. Data represents mean values±SEM.

To redirect T cell specificity, lentiviral vectors encoding CD123 CARs were developed. Each of the CARs includes codon-optimized sequences encoding one of two CD123-specific scFvs, 26292 and 32716 [18], respectively. The scFvs are fused in-frame to the human IgG4 Fc region, a CD28 costimulatory domain, and the CD3ζ signaling domain. Just downstream of the CAR sequence is a T2A ribosome skip sequence and a truncated human EGFR (EGFRt) transduction marker (FIG. 1A). OKT3 stimulated PBMCs from healthy donors were lenti-transduced and CAR expressing T cells were isolated by immunomagnetic selection using a biotinylated-Erbitux antibody followed by a secondary stain with anti-biotin magnetic beads. Following one REM cycle, the isolated cells were analyzed by flow cytometry for CAR surface expression and T-cell phenotype. Both Fc and EGFRt expression was greater than 90% in the generated T cell lines from three healthy donors and final T cell products consisted of a mixture of CD4 and CD8 positive T cells (FIGS. 1B, 1C).

CD123 CAR T Cells Specifically Target CD123 Expressing Tumor Cell Lines

Figure 2:
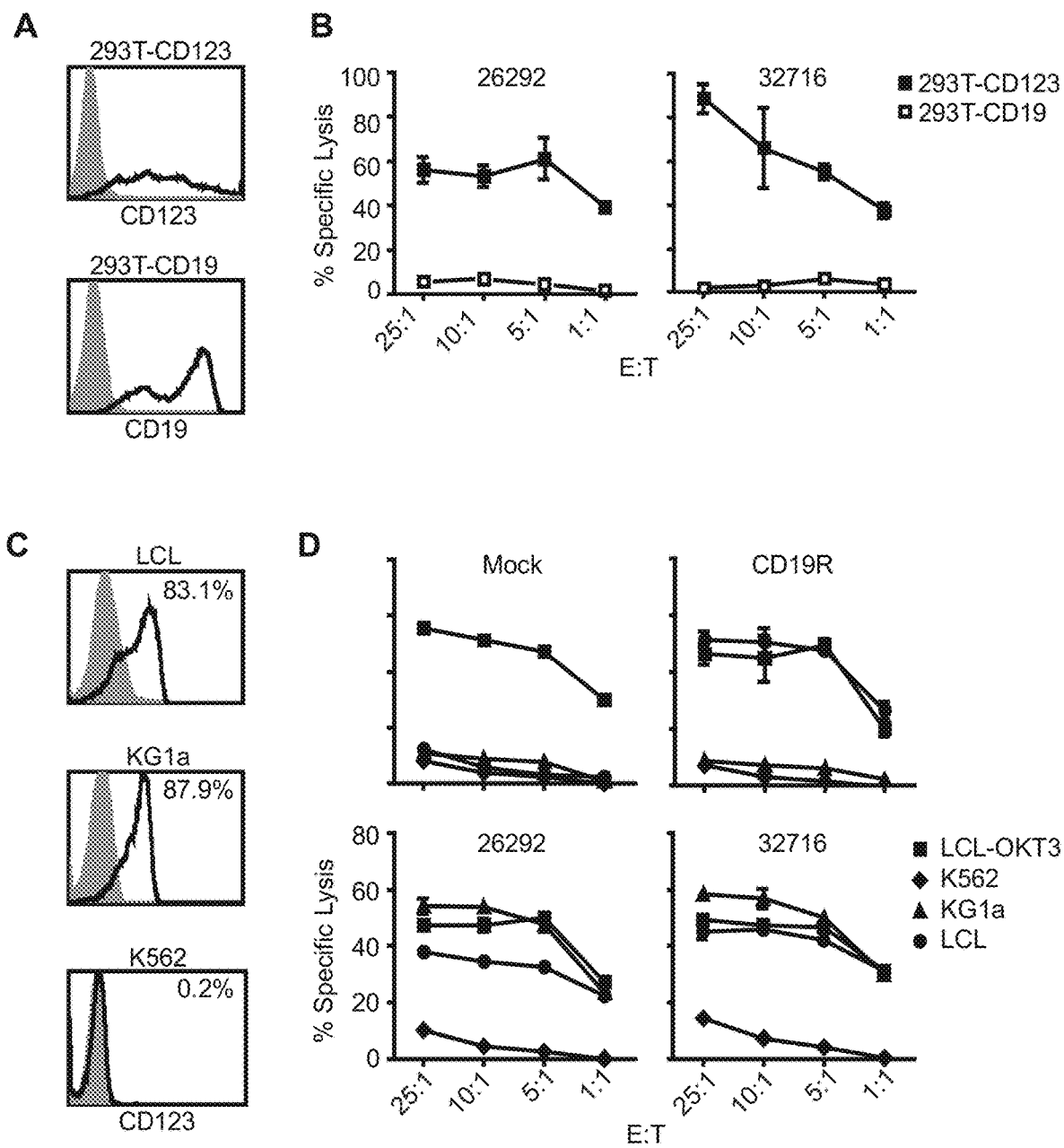
FIG. 2 shows that CD123-specific CAR expressing T cells lyse CD123-expressing tumor cell lines. (A) Flow kilometric analysis of 293T cells transiently transfected to express CD123 (top, black line) or CD19 (bottom, black line). Parental mock transduced 293T cells were stained with either anti-CD123 or anti-CD19 antibodies (grey filled, top and bottom) to determine background expression levels. (B) Specific cytotoxicity of CD123-CAR expressing T cells (26292 and 32716) against 293T cells expressing either CD123 (293T-CD123) or CD19 (293T-CD19) by chromium release assay. Data represents mean values of triplicate wells+S.D. (C) Flow kilometric analysis of CD123 on the AML cell line KG1a, the EBV-transformed LCL cell line, and the CML cell line K562. Percentage of cells positive for CD123 staining (black line) over isotype controls (grey filled) are indicated in each histogram. (D) Specific cytotoxicity of CD123-CAR T cells (26292 and 32716) against the CD19+ CD123+ LCL cell line and the CD19-CD123+ cell line KG1a by chromium release assay. OKT3 expressing LCL (LCL-OKT3) and the CD19-CD123-K562 cell lines were used as positive and negative control cell lines, respectively. Data represents mean values of triplicate wells+S.D.

To confirm the specificity of the CD123 CAR T cells, the ability of the genetically modified T cells to lyse 293T cells transiently transfected to express CD123 was examined (293T-CD123; FIG. 2A). Both CD123 CAR T cells generated efficiently lysed 293T-CD123, but not 293T cells transiently transfected to express CD19, demonstrating the specific recognition of CD123 (FIG. 2B). Next, the in vitro cytolytic capacity of CD123-specific T cells was investigated against tumor cell lines endogenously expressing CD123. Expression of CD123 on the cell lines LCL and KG1a were confirmed by flow cytometry (FIG. 2C). Both CD123-specific T cell lines efficiently lysed LCL and KG1a target lines, but not the CD123-K562 cell line (FIG. 2C). Pair-matched CD19-specific T cells effectively lysed CD19+ LCL targets, but not CD19-KG1a or K562 targets (FIG. 2D). Mock transduced parental cells lysed only the positive control LCL-OKT3 cell line (FIG. 2D).

Figure 3:
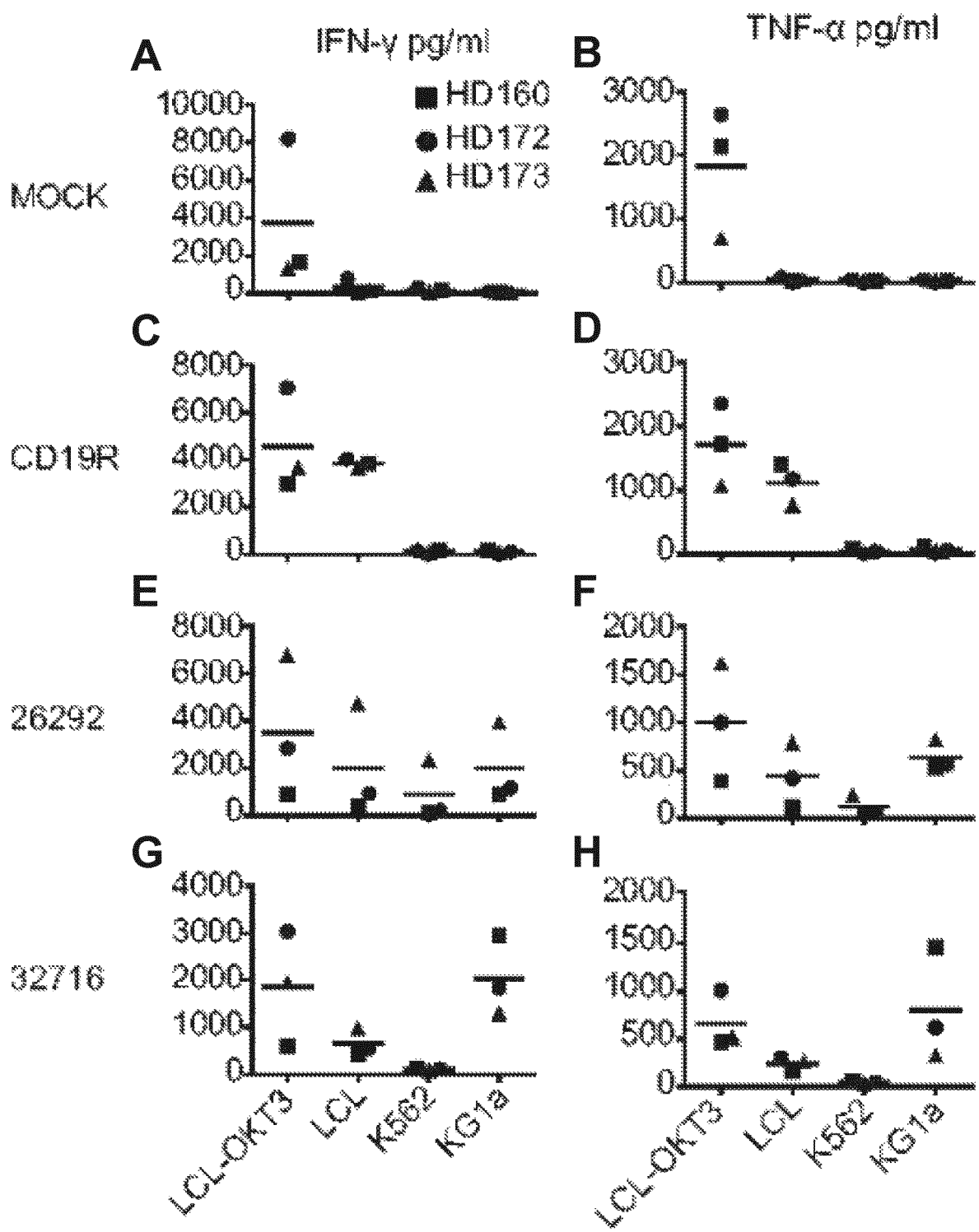
FIG. 3 shows that CD123-specific T cells release IFN-γ and TNF-α and proliferate in response to CD123 expressing target cells. (A)-(H) CD123 CAR T cells, or control pair matched T cells, from three healthy donors were co-cultured with the indicated cell lines for 24 hours at an E:T of 10:1 and the release of IFN-γ and TNF-α were quantified by Luminex multiplex bead technology. (I-T) Pair-matched CFSE labeled CD19 or CD123 specific T cells were co-cultured with the indicated stimulator cell lines for 96 hours at an E:T of 2:1, and analyzed by flow cytometry for CFSE dilution. Unstimulated T cells (filled histograms) were used as baseline T cell proliferation controls.
Figure 3:
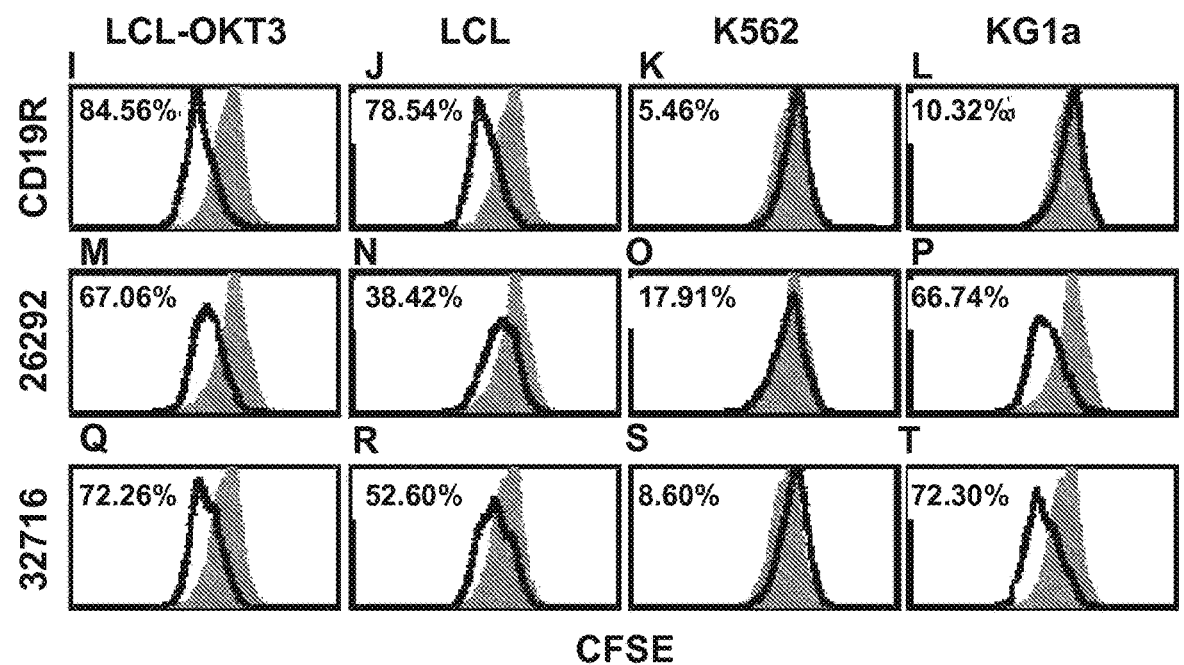

CD123 CAR T Cells Activate Multiple Effector Functions when Cocultured with CD123-Positive Target Cells To examine the effector function of CD123-specific T cells, the secretion of IFN-γ and TNF-α was measured following co-culture with various tumor cell lines (FIGS. 3C-3H). T cells expressing either CD123 CAR produced both IFN-γ and TNF-α when cocultured with CD123+ target cells (FIGS. 3E-3H), while pair-matched CD19-specific T cells secreted these cytokines only when cocultured with the CD19+ LCL or LCL-OKT3 cell line (FIGS. 3C and 3D). Additionally, both CD123-specific T cell lines proliferated when cocultured with either of the CD123+ cell lines LCL, LCL-OKT3, or KG1a, but not with the CD123-K562 cell line (FIGS. 3M-T). In contrast, pair-matched CD19 CAR-expressing T cells proliferated only when cocultured with LCL or LCL-OKT3 (FIGS. 3i-L).

Figure 15:
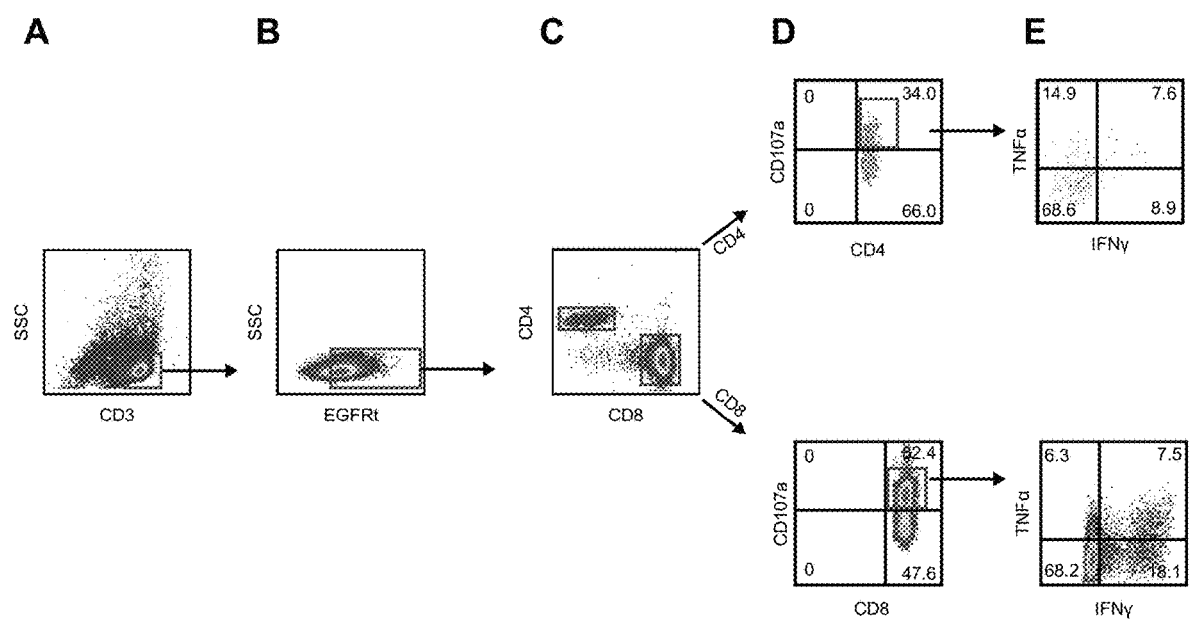
FIG. 15 illustrates a gating strategy used to investigate the activation of multiple effector functions by CD123-specific T cells in response to incubation with primary AML patient samples. The gating strategy for polychromatic flow cytometry to identify T cell effector functions is shown for CD123 CAR (26292-based) T cells following co-culture with AML 373. (A) An initial gate is set on CD3$^+$ cells. (B) A secondary gate, established using a fluorescence minus one control, is set on EGFRt$^+$ cells. (C) A tertiary gate is set for CD4$^+$ and CD8$^+$ populations. (D) A final gate is set on CD107a$^+$ cells. (E) IFN-γ and TNF-α production within the CD107a$^+$ populations. Quadrants were established using isotype control stained samples. Percentages in each quadrant are noted.

CD123 CAR T Cells Activate Multiple Effector Functions when Cocultured with Primary AML Samples The over-expression of CD123 on primary AML samples is well documented [27-29] and confirmed in this study (FIG. 14). Multifaceted T cell responses are critical for robust immune responses to infections and vaccines and may also play a role in the anti-tumor activity of CAR redirected T cells [30]. To investigate the ability CD123 CAR T cells to activate multiple effector pathways against primary AML samples, engineered T cells were cocultured with three different AML patient samples (179, 373, and 605) for 6 hours and evaluated for upregulation of CD107a and production of IFN-γ and TNF-α using polychromatic flow cytometry (gating strategy shown in FIG. 15). Cell surface mobilization of CD107a was observed in both the CD4 and CD8 compartments of CD123-specific T cells while pair-matched CD19R T cells no appreciable degranulation against primary AML samples (FIG. 4A, bar graphs). Further, subpopulations of CD107a+ CD123 CAR T cells also produced either IFN-γ, TNF-α, or both cytokines (FIG. 4A, pie charts). This multifunctional response was observed for both CD4 and CD8 populations (FIGS. 4A and 4B). Additionally, the ability of CAR engineered T cells to proliferate in response to co-culture with primary AML samples was examined. Both CD123-specific T cell lines were capable of proliferating following co-culture with AML 813 or pre B-ALL 802 samples (FIG. 4C). Proliferation was observed for in both the CD4 and CD8 populations (FIG. 16). Pair-matched CD19-specific T cells proliferated when cocultured with CD19+ pre B-ALL 802, but not when cocultured with AML 813.

CD123 CAR Expressing T Cells Target Primary AML Cells In Vitro

Figure 6:
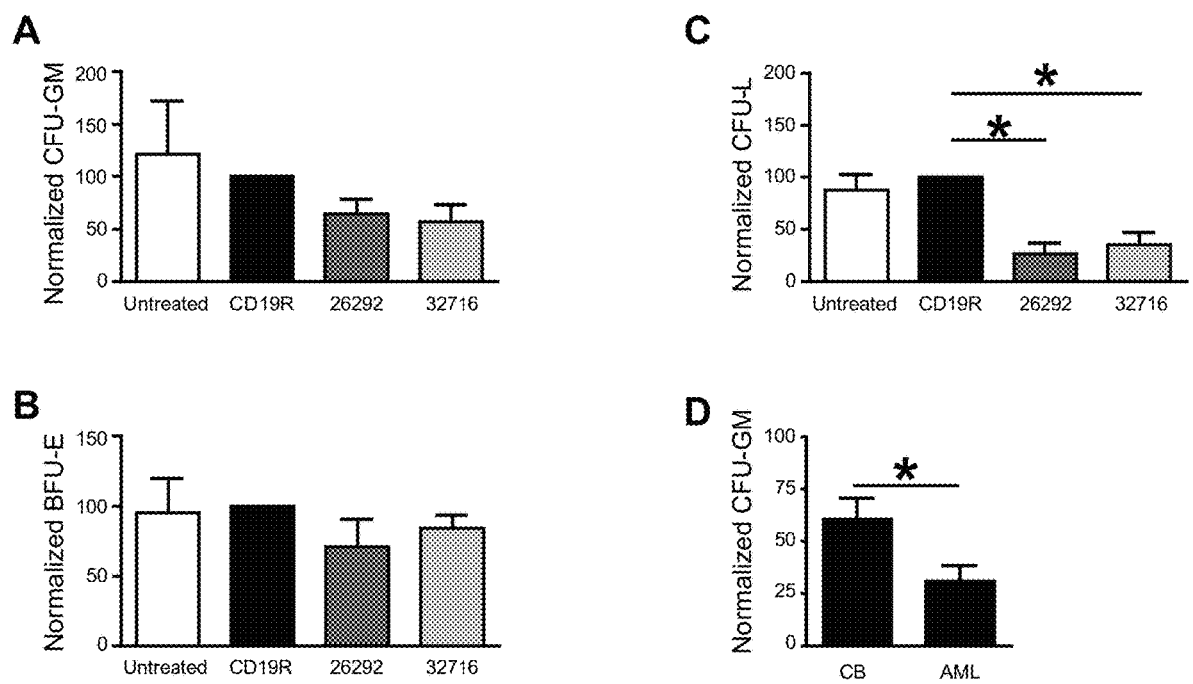
FIG. 6 shows the effect of CD123 CAR expressing T cells on normal and leukemic progenitor cells in vitro. (A and B) CD34+ cord blood (CB) cells (n=3) were CD34 immunomagnetically selected and cocultured with either CD19 or CD123-specific pair matched T cells or media alone (untreated) for 4 hours at an E:T of 25:1. The cells were then plated in semisolid methylcellulose progenitor culture for 14-18 days and scored for the presence of granulocyte-macrophage colony forming unit (CFU-GM, A) and burst forming unit erythroid (BFU-E, B) colonies. Percentages are normalized to CD19-specific T cell controls. Data represents mean values±SEM for three different CB samples. (C) CD34+ primary AML patient samples (AML 493, 519, or 545) were immunomagnetically selected and cocultured with either CD19 or CD123-specific pair matched T cells or media alone (untreated) for 4 hours at an E:T of 25:1. The cells were then plated in semisolid methylcellulose progenitor culture for 14-18 days and scored for the presence of leukemia colony forming units (CFU-L). Percentages are normalized to CD19-specific T cell controls. Data represents mean values±SEM for three different primary AML patient samples. *, p<0.05 using the unpaired Student's t-test comparing 26292 and 32716 to CD19R. (D) Combined colony formation of CB from (A) or AML cells from (C) treated with either CD123 targeting CAR construct (26292 or 32716) normalized to CD19R. *, p<0.05 using the unpaired Student's t-test.

CD123-Specific T Cells Do Not Eliminate Colony Formation by Cord Blood Cells In Vitro Given that CD123 is expressed on common myeloid progenitors (CMPs) [31], the effect of the engineered T cells on the colony forming ability of CD34-enriched normal cord blood (CB) samples was investigated. Myeloid and erythroid colony formation by CB samples was not significantly reduced following a 4 hour co-culture with CD123-CAR expressing T cells at an E:T of 25:1 when compared to pair-matched CD19R CAR T cells (FIGS. 6 A&B). Next, the ability of CD123-specific T cells to inhibit the growth of primary clonogenic AML cells was examined in vitro. Both CD123 CAR T cell lines significantly decreased the formation of leukemic colonies compared to pair-matched CD19R T cells (FIG. 6C). Notably, CD123-specific T cells had a greater impact on leukemic colony formation compared to normal myeloid colony formation (FIG. 6D, 69% reduction vs 31% reduction, respectively).

Figure 5:
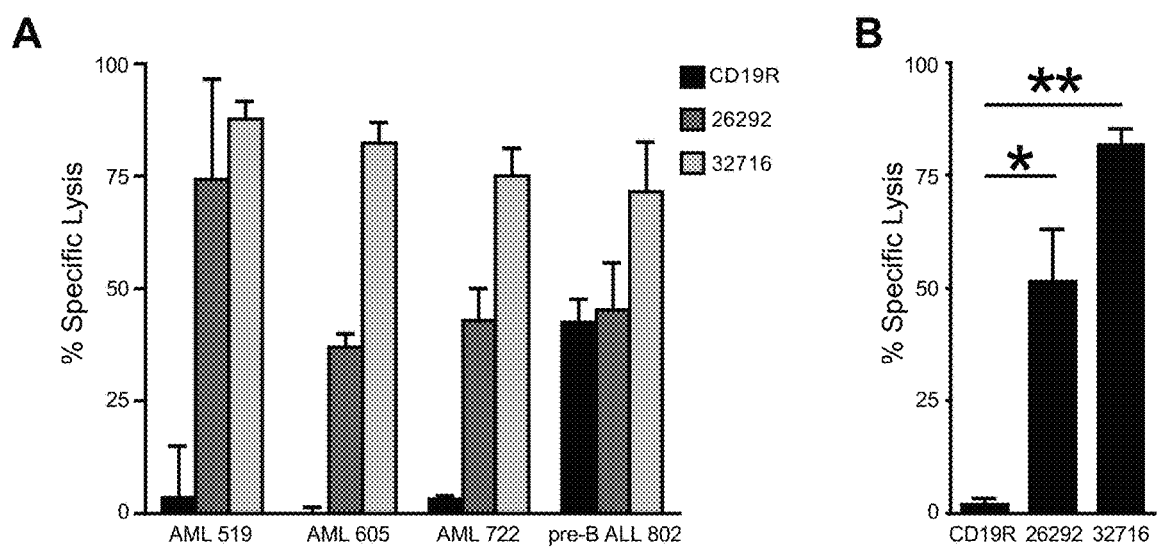
FIG. 5 shows that primary AML cells are specifically targeted by CD123 specific T cells. (A) Pair-matched CD19 or CD123-specific T cells were cocultured for 4 hours with 51Cr labeled CD34+ primary AML samples at an E:T of 25:1. LCL and K562 cell lines serve as positive and negative controls, respectively. Pre B-ALL 802 is a primary patient sample double positive for CD19 and CD123. Data represents mean values of triplicate wells+S.D. (B) Specific lysis of AML blasts from the three primary AML patient samples in (A). Data represents mean values±SEM. *, p<0.05 and **, p<0.0005 using the unpaired Student's t-test comparing 26292 and 32716 to CD19R.

T Cells from AML Patients can be Genetically Modified to Express CD123 CARs and Specifically Target Autologous Tumor Cells AML patient derived T cells are known to poorly repolarize actin and form defective immune synapses with autologous blasts [32]. Additionally, to the best of our knowledge, CAR expressing T cells derived from AML patients have yet to be described. Therefore, it was determined whether T cells from AML patients could be genetically modified to express CD123 CARs. Cryopreserved PBMCs (AML 605 and AML 722) or apheresis product (AML 559) were CD3/CD28 bead stimulated, and lentivirally transduced to express either of the CD123 CARs or a CD19R control CAR. All three patient sample derived T cells expressed the 26292 CAR (40-65% transduction efficiency), the 32716 CAR (46-70% transduction efficiency) and the CD19R CAR (To evaluate the ability of CD123-specific T cells to kill primary AML cells, pair-matched CD19R CAR or CD123 CAR expressing T cells were cocultured with primary CD34-enriched AML patient samples in a 4 hour $^{51}$Cr release assay. In contrast to pair-matched CD19R T cells, both CD123 CAR T cell lines robustly lysed all primary AML patient samples tested (FIG. 5A). Additionally, whereas no statistical difference was noted between the cytolytic capability of the CD123 CAR expressing T cells, both CD123-specific T cells demonstrated significantly enhanced cytotoxicity when compared to pair-matched CD19R-CAR T cells (FIG. 5B).

Figure 7A:
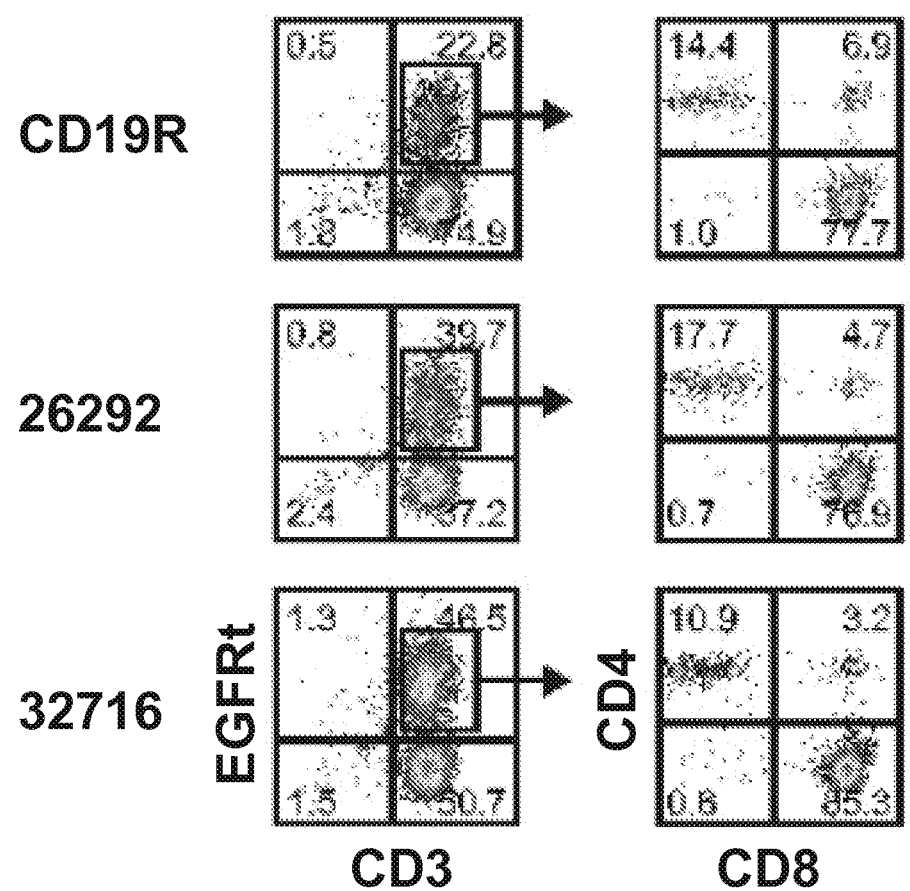
FIGS. 7A, 7B and 7C show that CD123 CAR redirected T cells derived from AML patients specifically lyse autologous blasts in vitro. (A) T cells from three AML patients were lentivirally transduced to express either CD19R, 26292, or 32716 CARs. Shown are T cell lines from AML 722 19 days post-transduction. (B) CD123 expression on target cells used in 51Cr release assay. The percentage of CD123+ cells and the relative fluorescence index (RFI) of each sample is indicated. (C) Results of 4 hour autologous killing assays using T cells engineered from three AML patient samples as effectors and 51Cr-labeled autologous CD34-enriched blasts as target cells. Data represents mean values of triplicate wells+S.D.
Figure 7B:
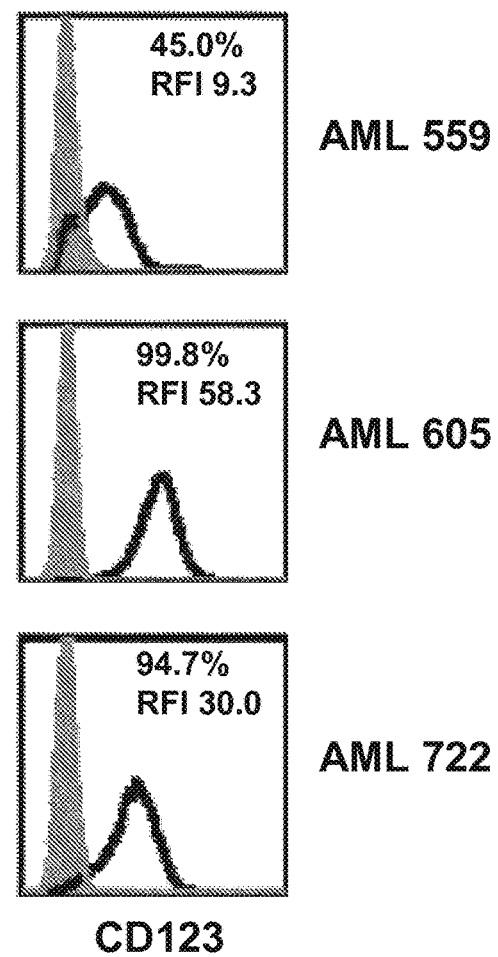
Figure 7C:
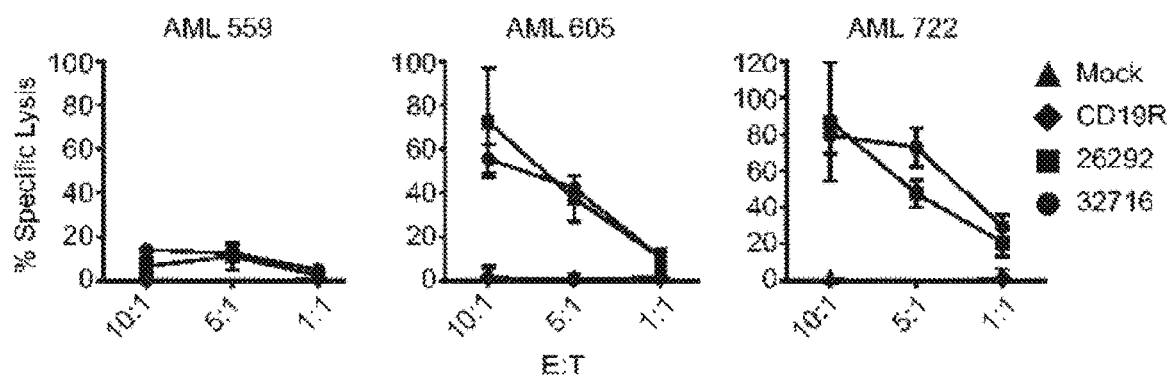

23-37% transduction efficiency). A representative example of the phenotype of AML patient derived CAR T cells is shown in FIG. 7A. Next, the cytolytic potential of AML patient derived CAR T cells against autologous CD34-enriched target cells was examined in a 4 hour $^{51}$Cr release assay. All of the autologous CD34-enriched cells expressed CD123, albeit at varying percentages and intensities (FIG. 7B). T cells derived from AML 605 and 722 efficiently lysed autologous blasts while T cells derived from AML 559 displayed low levels of autologous blast lysis likely due to the low and heterogeneous expression of CD123 on AML 559 blasts (FIG. 7C).

Discussion

The embodiments described herein include the generation of two novel CD123 targeting CARs using scFvs from recombinant immunotoxins (RITs), 26292 and 32716, which bind distinct epitopes and have similar binding affinities for CD123 [18]. When expressed by a population of T cells, these CD123 targeting CARs redirect T cell specificity against CD123 expressing cells. Using a standard 4 hour chromium-51 (51Cr) release assay, healthy donor T cells that were engineered to express the CD123 CARs efficiently lysed CD123+ cell lines and primary AML patient samples. Additionally, both of the CD123 CAR T cells activated multiple effector functions following co-culture with CD123+ cell lines and primary AML patient samples. Further, CD123-targeting T cells did not significantly reduce the number of colony-forming unit granulocyte-macrophage (CFU-GM) or burst-forming unit erythroid (BFU-E) colonies from cord blood (CB) when compared to CD19 CAR T cells. Notably, while CD19-specific T cells had little impact on leukemic colony formation of primary AML samples, CD123-targeting T cells significantly reduced leukemic colony formation in vitro. It was also shown that AML patient derived T cells can express CD123 CARs and lyse autologous blasts in vitro.

T cells expressing either of the two CD123-specific CARs can specifically lyse CD123 expressing cell lines and primary AML patient samples, and activate multiple effector functions in an antigen specific manner in vitro demonstrating that both epitopes are potential targets for treatment. No major differences were observed between the CD123 CAR engineered T cell lines with respect to target cell killing, cytokine secretion, or proliferation when cocultured with CD123+ cells. One possible explanation for this is the binding affinities of the CD123-specific scFvs used in the CD123-CARs are in the nanomolar range and differ by less than 3-fold and thus offer no significant advantage in target antigen binding is conferred by either scFv [18].

The expression of multiple cell surface antigens on AML cells has been well documented [4, 27, 34]. Targeting some of these antigens via CAR-expressing T cells may not be feasible. For instance, the AML associated antigen TIM-3 is expressed on a subset of exhausted T cells [35, 36] and targeting TIM-3 using CAR-engineered T cells may result in the autolysis of genetically modified cells. Additionally, CD47 is ubiquitously expressed [37] and thus unlikely targetable by CAR-engineered T cells. The CD33 differentiation antigen is predominately expressed on myeloid cells and immunotherapies targeting CD33 such as Gemtuzumab ozogamicin, CD33/CD3 bispecific T cell engaging antibodies, and a CD33 CAR are currently used in clinical and pre-clinical settings [17, 38, 39]. Like TIM-3, CD33 is expressed on a subset of T cells making it a non-ideal target for a CAR based therapy [40]. Additionally, the antileukemic activity of CD33-targeting therapies was often accompanied with slow recovery of hematopoiesis and cytopenias likely the result of CD33 expression on long-term self-renewing normal hematopoietic stem cells (HSCs) [41]. Further, hepatotoxicities are a common side effect of CD33-targeted treatments and are possibly due to the unintended targeting of CD33+ Kupffer cells [42].

Expression of CD123 is absent on T cells, predominantly restricted to cells of the myeloid lineage [43], and largely absent on HSCs [27]. Together, these observations made CD123 an attractive target for CAR mediated T cell therapy. Therapeutics specific for CD123 have displayed favorable safety profiles in phase I trials (ClinicalTrials.gov ID: NCT00401739 and NCT00397579). Unfortunately, these therapies have failed to induce responses in the vast majority of treated patients. The CD123-CAR expressing T cells generated here displayed potent cytolytic capacity in vitro against CD123+ cell lines and primary AML samples. The studies described below show that primary samples from patients with poor-risk AML were susceptible to CD123 CAR T cell mediated cytotoxicity. Collectively, in the small cohort of primary samples used for short-term cytotoxicity assays, AML patient samples that exhibited high-risk features at diagnosis and/or chemoresistant were sensitive to CD123 CAR killing similar to what was observed in experiments using CD123+ cell lines. Further analysis will need to be done to confirm that these results will hold true for a larger cohort of samples.

Multifunctional T cell responses correlate with the control of virus infection and may be important in an anti-tumor CAR T cell response [44]. Indeed, patients responsive to CD19 CAR T cell therapy have detectable T cell responses (i.e. degranulation, cytokine secretion or proliferation) post-therapy in response to CD19+ targets ex vivo [11, 12, 14]. In the Examples below, it was demonstrated that the functionality of CD123-CAR expressing T cells by analyzing the upregulation of CD107a, production of inflammatory cytokines and proliferation of CD123-specific T cells in response to both CD123+ cell lines and primary AML samples. Further, multifunctionality was observed in both the CD4+ and CD8+ compartments, which may promote sustained anti-leukemic activity and boost anti-leukemic activity within the tumor microenvironment [45, 46]. The inclusion of other costimulatory domains such as 4-1BB, and the use of "younger" less differentiated T cells may further augment CD123 CAR responses and are an area of active research [9, 47].

Further, CD123-specific T cells do not inhibit normal progenitor colony formation—even at an E:T of 25:1. Expression of CD123 on lineage-CD34+ CD38-cells is a hallmark of the common myeloid progenitor cell and thus a likely target of CD123 CAR T cells [31]. While a decrease in the relative percentage of myeloid-derived colonies was observed when CB cells were incubated with CD123-specific T cells, the decrease was not significantly less than pair-matched CD19R CAR T cells. It is possible that the limited sample size attributes to this result and further experimentation may reveal a significant decrease in CFU-GM formation in CD123 CAR T cell treated cord blood samples. Additionally, the 4 hour co-culture of T cells and CB cells prior to plating may not be a long enough time period to observe an effect on normal myeloid progenitor colony formation and that longer incubation times may decrease the number of observed myeloid derived colonies. However, using the same methodology as was used for CB cells, a substantial decrease in the number of leukemic colonies formed was observed when primary CD34-enriched AML patient samples were incubated with CD123 CAR T cells, suggesting that the 4 hour incubation time is sufficient to observe an effect between leukemic and normal colony formation. Alternatively, the lower relative expression of CD123 on CB cells compared to AML cells may in part result in the inability of CD123 CAR T cells to alter myeloid derived colony formation in vitro. While others have demonstrated that CD123 is expressed only in a small fraction of lineage-CD34+CD38-HSCs, and two phase I trials using agents targeting CD123 revealed no long term myelosuppression, further studies are needed to evaluate the effect of CD123 CAR T cell therapy on hematopoiesis. In order to control unwanted off-target toxicities, EGFRt was included in the lentiviral construct to allow for ablation of CAR expressing T cells. Other strategies to modulate CAR T cell activity such as the inducible caspase 9 apoptosis switch [48] or electroporation of CAR mRNA [49] are also of high interest given the potential for killing of normal cells expressing CD123.

Further, it was demonstrated that cryopreserved PBMCs from AML patients with active disease can be genetically modified to express CD123 CARs and exhibit potent cytolytic activity against autologous leukemic blasts in 2/3 of the samples. While CD123 CAR-expressing T cells from AML 559 failed to lyse autologous blasts which expressed low levels of CD123, these CAR T cells did lyse CD123+ LCL and KG1a cell lines (data not shown) suggesting that the generated T cells have the potential to target CD123-expressing target cells. To our knowledge, this is the first demonstration that AML patient-derived T cells can be engineered to express a CAR and exhibit redirected antigen specific cytotoxicity against autologous blasts.

Collectively, the results of the studies described in the Examples below demonstrate that CD123 CAR T cells can distinguish between CD123+ and CD123-cells, and can activate multiple T cell effector functions against a panel of poor-risk primary AML patient samples. Notably, CD123-specific T cells did not significantly alter normal progenitor colony formation but considerably reduced the growth of clonogenic myeloid leukemic progenitors in vitro. It was also demonstrated that T cells derived from AML patients can be genetically modified to express CD123-specific CARs and lyse autologous blasts in vitro. Therefore, CD123 CAR T cells are a promising candidate for immunotherapy of AML.

Example 2: CD123CAR-Transduced T Cells Delay Leukemic Progression In Vivo

CD123CAR Constructs. 26292CAR(S228P+L235E) and 32716CAR(S228P+L235E) constructs were generated as described in Example 1 above. Two additional CD123CAR constructs were also generated that included an additional mutation in the IgG4 hinge at position 297 (N297Q) for each scFv ("26292CAR(S228P+L235E+N297Q)" and "32716CAR(S228P+L235E+N297Q)") (FIGS. 12 and 13, mutations bolded and underlined).

NSG mice implanted with AML tumor cells (day 0), and were treated with $5.0 \times 10^6$ CAR+ T cells expressing either the 26292CAR(S228P+L235E) or the 26292CAR(S228P+L235E+N297Q) on day 5, and leukemic progression was monitored by bioluminescent imaging. As shown in FIG. 8, leukemic burden progressed on day 8 as compared to the day of treatment in mice treated with T-cells transduced with 26292CAR(S228P+L235E), indicating that cells transduced with the CD123CAR construct having hinge region mutations at positions S228P and L235E had no effect in vivo. In contrast, mice treated with T cells transduced with 26292CAR(S228P+L235E+N297Q) showed a reduction in tumor size as compared to the day of treatment, indicating that the addition of a hinge region mutation at position 297 (N297Q) results in a CD123CAR construct that is able to delay leukemic progression in vivo.

REFERENCES

The references, patents and published patent applications listed below, and all references cited in the specification above are hereby incorporated by reference in their entirety, as if fully set forth herein.
1. Eaves, C. J. and R. K. Humphries, Acute myeloid leukemia and the Wnt pathway. N Engl J Med, 2010. 362(24): p. 2326-7.
2. Dohner, H., et al., Diagnosis and management of acute myeloid leukemia in adults: recommendations from an international expert panel, on behalf of the European LeukemiaNet. Blood, 2010. 115(3): p. 453-74.
3. Majeti, R., Monoclonal antibody therapy directed against human acute myeloid leukemia stem cells. Oncogene, 2011. 30(9): p. 1009-19.

4. Kikushige, Y., et al., TIM-3 is a promising target to selectively kill acute myeloid leukemia stem cells. Cell Stem Cell, 2010. 7(6): p. 708-17.
5. Jena, B., G. Dotti, and L. J. Cooper, Redirecting T-cell specificity by introducing a tumor-specific chimeric antigen receptor. Blood, 2010. 116(7): p. 1035-44.
6. Cooper, L. J., et al., T-cell clones can be rendered specific for CD19: toward the selective augmentation of the graft-versus-B-lineage leukemia effect. Blood, 2003. 101(4): p. 1637-44.
7. Hudecek, M., et al., The B-cell tumor-associated antigen ROR1 can be targeted with T cells modified to express a ROR1-specific chimeric antigen receptor. Blood, 2010. 116(22): p. 4532-41.
8. Kochenderfer, J. N., et al., Construction and preclinical evaluation of an anti-CD19 chimeric antigen receptor. J Immunother, 2009. 32(7): p. 689-702.
9. Milone, M. C., et al., Chimeric receptors containing CD137 signal transduction domains mediate enhanced survival of T cells and increased antileukemic efficacy in vivo. Mol Ther, 2009. 17(8): p. 1453-64.
10. Brentjens, R. J., et al., Eradication of systemic B-cell tumors by genetically targeted human T lymphocytes co-stimulated by CD80 and interleukin-15. Nat Med, 2003. 9(3): p. 279-86.
11. Brentjens, R. J., et al., Safety and persistence of adoptively transferred autologous CD19-targeted T cells in patients with relapsed or chemotherapy refractory Bcell leukemias. Blood, 2011. 118(18): p. 4817-28.
12. Kochenderfer, J. N., et al., B-cell depletion and remissions of malignancy along with cytokine-associated toxicity in a clinical trial of anti-CD19 chimeric antigen-receptor-transduced T cells. Blood, 2011.
13. Savoldo, B., et al., CD28 costimulation improves expansion and persistence of chimeric antigen receptor-modified T cells in lymphoma patients. J Clin Invest, 2011. 121(5): p. 1822-6.
14. Kalos, M., et al., T cells with chimeric antigen receptors have potent antitumor effects and can establish memory in patients with advanced Leukemia. Sci Transl Med, 2011. 3(95): p. 95ra73.
15. Till, B. G., et al., CD20-specific adoptive immunotherapy for lymphoma using a chimeric antigen receptor with both CD28 and 4-1BB domains: pilot clinical trial results. Blood, 2012.
16. Peinert, S., et al., Gene-modified T cells as immunotherapy for multiple myeloma and acute myeloid leukemia expressing the Lewis Y antigen. Gene Ther, 2010. 17(5): p. 678-86.
17. Dutour, A., et al., In Vitro and In Vivo Antitumor Effect of Anti-CD33 Chimeric Receptor-Expressing EBV-CTL against CD33 Acute Myeloid Leukemia. Adv Hematol, 2012. 2012: p. 683065.
18. Du, X., M. Ho, and I. Pastan, New immunotoxins targeting CD123, a stem cell antigen on acute myeloid leukemia cells. J Immunother, 2007. 30(6): p. 607-13.
19. Pelloquin, F., J. P. Lamelin, and G. M. Lenoir, Human B lymphocytes mmortalization by Epstein-Barr virus in the presence of cyclosporin A. In Vitro Cell Dev Biol, 1986. 22(12): p. 689-94.
20. Wang, X., et al., A transgene-encoded cell surface polypeptide for selection, in vivo tracking, and ablation of engineered cells. Blood, 2011. 118(5): p. 1255-63.
21. Reddy, M. P., et al., Elimination of Fc receptor-dependent effector functions of a modified IgG4 monoclonal antibody to human CD4. J Immunol, 2000. 164(4): p. 1925-33.
22. Nguyen, P., I. Moisini, and T. L. Geiger, Identification of a murine CD28 dileucine motif that suppresses single-chain chimeric T-cell receptor expression and function. Blood, 2003. 102(13): p. 4320-5.
23. Jensen, M. C., et al., Human T lymphocyte genetic modification with naked DNA. Mol Ther, 2000. 1(1): p. 49-55.
24. Riddell, S. R. and P. D. Greenberg, The use of anti-CD3 and anti-CD28 monoclonal antibodies to clone and expand human antigen-specific T cells. J Immunol Methods, 1990. 128(2): p. 189-201.
25. Brown, C. E., et al., Recognition and killing of brain tumor stem-like initiating cells by CD8+ cytolytic T cells. Cancer Res, 2009. 69(23): p. 8886-93.
26. Bhatia, R., et al., Abnormal function of the bone marrow microenvironment in chronic myelogenous leukemia: role of malignant stromal macrophages. Blood, 1995. 85(12): p. 3636-45.
27. Jordan, C. T., et al., The interleukin-3 receptor alpha chain is a unique marker for human acute myelogenous leukemia stem cells. Leukemia, 2000. 14(10): p. 1777-84.
28. Jin, L., et al., Monoclonal antibody-mediated targeting of CD123, IL-3 receptor alpha chain, eliminates human acute myeloid leukemic stem cells. Cell Stem Cell, 2009. 5(1): p. 31-42.
29. Munoz, L., et al., Interleukin-3 receptor alpha chain (CD123) is widely expressed in hematologic malignancies. Haematologica, 2001. 86(12): p. 1261-9.
30. Seder, R. A., P. A. Darrah, and M. Roederer, T-cell quality in memory and protection: implications for vaccine design. Nat Rev Immunol, 2008. 8(4): p. 247-58.
31. Manz, M. G., et al., Prospective isolation of human clonogenic common myeloid progenitors. Proc Natl Acad Sci USA, 2002. 99(18): p. 11872-7.
32. Le Dieu, R., et al., Peripheral blood T cells in acute myeloid leukemia (AML) patients at diagnosis have abnormal phenotype and genotype and form defective immune synapses with AML blasts. Blood, 2009. 114(18): p. 3909-16.
33. Oka, Y., et al., Induction of WT1 (Wilms' tumor gene)-specific cytotoxic T lymphocytes by WT1 peptide vaccine and the resultant cancer regression. Proc Natl Acad Sci USA, 2004. 101(38): p. 13885-90.
34. Majeti, R., et al., CD47 is an adverse prognostic factor and therapeutic antibody target on human acute myeloid leukemia stem cells. Cell, 2009. 138(2): p. 286-99.
35. Golden-Mason, L., et al., Negative immune regulator Tim-3 is overexpressed on T cells in hepatitis C virus infection and its blockade rescues dysfunctional CD4+ and CD8+ T cells. J Virol, 2009. 83(18): p. 9122-30.
36. Jin, H. T., et al., Cooperation of Tim-3 and PD-1 in CD8 T-cell exhaustion during chronic viral infection. Proc Natl Acad Sci USA, 2010. 107(33): p. 14733-8.
37. Brown, E. J. and W. A. Frazier, Integrin-associated protein (CD47) and its ligands. Trends Cell Biol, 2001. 11(3): p. 130-5.
38. Walter, R. B., et al., Acute myeloid leukemia stem cells and CD33-targeted immunotherapy. Blood, 2012. 119(26): p. 6198-208.
39. Aigner, M., et al., T lymphocytes can be effectively recruited for ex vivo and in vivo lysis of AML blasts by a novel CD33/CD3-bispecific BiTE((R)) antibody construct. Leukemia, 2012.
40. Hernandez-Caselles, T., et al., A study of CD33 (SI-GLEC-3) antigen expression and function on activated 41. Sievers, E. L., et al., Efficacy and safety of gemtuzumab ozogamicin in patients with CD33-positive acute myeloid leukemia in first relapse. J Clin Oncol, 2001. 19(13): p. 3244-54.
42. Tsimberidou, A. M., et al., The role of gemtuzumab ozogamicin in acute leukaemia therapy. Br J Haematol, 2006. 132(4): p. 398-409.
43. Sato, N., et al., Expression and factor-dependent modulation of the interleukin-3 receptor subunits on human hematopoietic cells. Blood, 1993. 82(3): p. 752-61.
44. Appay, V., D. C. Douek, and D. A. Price, CD8+ T cell efficacy in vaccination and disease. Nat Med, 2008. 14(6): p. 623-8.
45. Moeller, M., et al., Sustained antigen-specific antitumor recall response mediated by gene-modified CD4+T helper-1 and CD8+ T cells. Cancer Res, 2007. 67(23): p. 11428-37.
46. Schietinger, A., et al., Bystander killing of cancer requires the cooperation of CD4(+) and CD8(+) T cells during the effector phase. J Exp Med, 2010. 207(11): p. 2469-77.
47. Gattinoni, L., et al., A human memory T cell subset with stem cell-like properties. Nat Med, 2011. 17(10): p. 1290-7.
48. Straathof, K. C., et al., An inducible caspase 9 safety switch for T-cell therapy. Blood, 2005. 105(11): p. 4247-54.
49. Yoon, S. H., et al., Adoptive immunotherapy using human peripheral blood lymphocytes transferred with RNA encoding Her-2/neu-specific chimeric immune receptor in ovarian cancer xenograft model. Cancer Gene Ther, 2009. 16(6): p. 489-97.
50. Strohl, W. R., Optimization of Fc-mediated effector functions of monoclonal antibodies. Curr Op Biotech. 2009. 20:685-691.

What is claimed is:

1. A method of treating acute myeloid leukemia comprising administering to a patient in need thereof a pharmaceutical composition comprising a population of human T cells harboring an expression vector comprising a nucleic acid molecule encoding a chimeric antigen receptor comprising: an anti-CD123 scFv region, an IgG4 hinge region comprising SEQ ID NO: 13 having an N to Q amino acid substitution at position 79 and a L to E amino acid substitution at position 17 and, optionally, an S to P amino acid substitution at position 10, and a T cell receptor zeta chain signaling domain.

2. The method of claim 1, wherein the human T cells are allogenic or autologous to the patient.

3. The method of claim 1, further comprising treating the patient with one or more anticancer therapies selected from stem cell transplantation, radiation therapy, surgical resection, chemotherapeutics, immunotherapeutics, targeted therapeutics or a combination thereof.

4. The method of claim 1, wherein the IgG4 hinge region comprising SEQ ID NO:13 has a S to P amino acid substitution at position 10.

5. The method of claim 1, wherein the chimeric antigen receptor further comprises a co-stimulatory signaling domain selected from the group consisting of: a CD27 co-stimulatory signaling domain, a CD28 co-stimulatory signaling domain, a 4-1BB co-stimulatory signaling domain, and an OX40 co-stimulatory signaling domain.

6. The method of claim 1, wherein the anti-CD123 scFV domain comprises: the VL and VH domain of recombinant immunotoxin 26292 or the VL and VH domain of recombinant immunotoxin 32716.

7. The method of claim 1, wherein the chimeric antigen receptor comprises an amino acid sequence selected from the group consisting of: SEQ ID NO:11 and SEQ ID NO:12.

8. The method of claim 1, wherein the expression vector comprises a nucleotide sequence selected from the group consisting of: SEQ ID NO: 1, SEQ ID NO:2, SEQ ID NO:3 and SEQ ID NO:4.

9. The method of claim 1, wherein the chimeric antigen receptor comprises a CD28 transmembrane domain.

10. The method of claim 1, wherein the expression vector is a viral vector.

11. The method of claim 10, wherein the viral vector is a lentiviral vector.

12. The method of claim 1, wherein the anti-CD123 scFv region is a humanized anti-CD123 scFv region.

13. The method of claim 1, wherein the wherein the anti-CD123 scFv region comprises amino acids 23-266 of SEQ ID NO:9.

14. The method of claim 1, wherein the anti-CD123 scFv region comprises amino acids 23-259 of SEQ ID NO:10.

15. The method of claim 1, wherein the wherein the IgG4 hinge region comprises amino 267-495 of SEQ ID NO:9.

16. The method of claim 1, wherein the chimeric antigen receptor further comprises a 4-IBB co-stimulatory signaling domain.

17. The method of claim 1, wherein the wherein the chimeric antigen receptor further comprises a CD28 co-stimulatory signaling domain.

18. The method of claim 1, wherein the CD28 co-stimulatory domain comprises amino acids 498-564 of SEQ ID NO:9.

19. The method of claim 1, wherein the CD28 co-stimulatory domain comprises amino acids 489-557 of SEQ ID NO:10.

20. The method of claim 1, wherein the T cell receptor zeta chain signaling domain comprises amino acids 568-679 of SEQ ID NO:9.

* * * * *

SEQUENCE LISTING

```
<160> NUMBER OF SEQ ID NOS: 13

<210> SEQ ID NO 1
<211> LENGTH: 2052
<212> TYPE: DNA
<213> ORGANISM: Artificial Sequence
<220> FEATURE:
<223> OTHER INFORMATION: antisense nucleotide sequence of the
      32716CAR(S228P+L235E) construct

<400> SEQUENCE: 1
gctagcgccg ccaccatgct gctgctggtg accagcctgc tgctgtgcga gctgccccac      60
cccgcctttc tgctgatccc ccagattcag ctggtgcaga gcggcccgga actgaaaaaa     120
ccgggcgaaa ccgtgaaaat tagctgcaaa gcgagcggct atatttttac caactatggc     180
atgaactggg tgaaacaggc gccgggcaaa agctttaaat ggatgggctg gattaacacc     240
tataccggcg aaagcaccta tagcgcggat tttaaaggcc gctttgcgtt tagcctggaa     300
accagcgcga gcaccgcgta tctgcatatt aacgatctga aaaacgaaga taccgcgacc     360 tattttttgcg cgcgcagcgg cggctatgat ccgatggatt attggggcca gggcaccagc     420
gtgaccgtga gcagcggcgg cggcggcagc ggcggcggcg gcagcggcgg cggcggcagc     480
gatattgtgc tgacccagag cccggcgagc ctggcggtga gcctgggcca gcgcgcgacc     540
attagctgcc gcgcgagcga aagcgtggat aactatggca cacctttat gcattggtat     600 cagcagaaac cgggccagcc gccgaaactg ctgatttatc gcgcgagcaa cctggaaagc     660
ggcattccgg cgcgctttag cggcagcggc agccgcaccg atttaccct gaccattaac     720 ccggtggaag cggatgatgt ggcgacctat tattgccagc agagcaacga agatccgccg     780
acctttggcg cgggcaccaa actggaactg aaagagagca gtacggccc tccctgcccc     840 ccttgccctg ccccgagtt cgaggcgga cccagcgtgt tcctgttccc cccaagccc     900 aaggacaccc tgatgatcag ccggacccc gaggtgacct gcgtggtggt ggacgtgagc     960
caggaagatc ccgaggtcca gttcaattgg tacgtggacg gcgtggaagt gcacaacgcc    1020
aagaccaagc ccagagagga acagttcaac agcacctacc gggtggtgtc tgtgctgacc    1080
gtgctgcacc aggactggct gaacggcaaa gaatacaagt gcaaggtgtc caacaagggc    1140
ctgcccagca gcatcgaaaa gaccatcagc aaggccaagg gccagcctcg cgagcccag    1200 gtgtacaccc tgcctccctc ccaggaagag atgaccaaga accaggtgtc cctgacctgc    1260
```

```
ctggtgaagg gcttctaccc cagcgacatc gccgtggagt gggagagcaa cggccagcct      1320
gagaacaact acaagaccac ccctcccgtg ctggacagcg acggcagctt cttcctgtac      1380
agccggctga ccgtggacaa gagccggtgg caggaaggca acgtctttag ctgcagcgtg      1440
atgcacgagg ccctgcacaa ccactacacc agaagagcc tgagcctgtc cctgggcaag      1500
atgttctggg tgctggtggt ggtgggcggg gtgctggcct gctacagcct gctggtgaca      1560
gtggccttca tcatcttttg ggtgcggagc aagcggagca gaggcggcca cagcgactac      1620
atgaacatga ccccagacg gcctggcccc accggaagc actaccagcc ctacgcccca      1680
cccagggact tgccgccta ccgtccggc ggagggcggg tgaagttcag cagaagcgcc      1740
gacgcccctg cctaccagca gggccagaat cagctgtaca cgagctgaa cctgggcaga      1800 agggaagagt acgacgtcct ggataagcgg agaggccggg accctgagat gggcggcaag      1860
cctcggcgga agaaccccca ggaaggcctg tataacgaac tgcagaaaga caagatggcc      1920
gaggcctaca gcgagatcgg catgaagggc gagcggaggc ggggcaaggg ccacgacggc      1980
ctgtatcagg gcctgtccac cgccaccaag ataccctacg acgccctgca catgcaggcc      2040
ctgcccccaa gg                                                         2052

<210> SEQ ID NO 2
<211> LENGTH: 2031
<212> TYPE: DNA
<213> ORGANISM: Artificial Sequence
<220> FEATURE:
<223> OTHER INFORMATION: antisense nucleotide sequence of the
      26292CAR(S228P+L235E) construct

<400> SEQUENCE: 2
gctagcgccg ccaccatgct gctgctggtg accagcctgc tgctgtgcga gctgccccac        60
cccgcctttc tgctgatccc ccaggtgcag ctgcagcagc cgggcgcgga actggtgcgc       120
ccgggcgcga gcgtgaaact gagctgcaaa gcgagcggct tacctttac cagctattgg       180 atgaactggg tgaaacagcg cccggatcag ggcctggaat ggattggccg cattgatccg       240
tatgatagcg aaacccatta taaccagaaa tttaaagata agcgattct gaccgtggat       300 aaaagcagca gcaccgcgta tatgcagctg agcagcctga ccagcgaaga tagcgcggtg       360
tattattgcg cgcgcggcaa ctgggatgat tattggggcc agggcaccac cctgaccgtg       420
agcagcggcg gcggcggcag cggcggcggc ggcagcggcg gcggcggcag cgatgtgcag       480
attacccaga gcccgagcta tctggcggcg agcccgggcg aaaccattac cattaactgc       540
cgcgcgagca aaagcattag caaagatctg gcgtggtatc aggaaaaacc gggcaaaacc       600
aacaaactgc tgatttatag cggcagcacc ctgcagagcg gcattccgag ccgctttagc       660
ggcagcggca gcggcaccga ttttaccctg accattagca gcctggaacc ggaagatttt       720
gcgatgtatt attgccagca gcataacaaa tatccgtata cctttggcgg cggcaccaaa       780
ctggaaatta agagagcaa gtacggccct cctgcccc cttgccctgc cccgagttc      840 gagggcggac ccagcgtgtt cctgttcccc ccaagccca aggacaccct gatgatcagc       900 cggaccccg aggtgacctg cgtggtggtg gacgtgagcc aggaagatcc cgaggtccag       960
ttcaattggt acgtggacgg cgtggaagtg cacaacgcca agaccaagcc cagagaggaa      1020
cagttcaaca gcacctaccg ggtggtgtct gtgctgaccg tgctgcacca ggactggctg      1080
aacggcaaag aatacaagtg caaggtgtcc aacaagggcc tgcccagcag catcgaaaag      1140
accatcagca aggccaaggg ccagcctcgc gagccccagg tgtacaccct gcctccctcc      1200
```

```
caggaagaga tgaccaagaa ccaggtgtcc ctgacctgcc tggtgaaggg cttctacccc    1260
agcgacatcg ccgtggagtg ggagagcaac ggccagcctg agaacaacta caagaccacc    1320
cctcccgtgc tggacagcga cggcagcttc ttcctgtaca gcggctgacg cgtggacaag    1380
agccggtggc aggaaggcaa cgtctttagc tgcagcgtga tgcacgaggc cctgcacaac    1440
cactacaccc agaagagcct gagcctgtcc ctgggcaaga tgttctgggt gctggtggtg    1500
gtgggcgggg tgctggcctg ctacagcctg ctggtgacag tggccttcat catcttttgg    1560
gtgcggagca agcggagcag aggcggccac agcgactaca tgaacatgac ccccagacgg    1620
cctggcccca cccggaagca ctaccagccc tacgcccacc caggggactt tgccgcctac    1680
cggtccggcg agggcgggt gaagttcagc agaagcgccg acgcccctgc ctaccagcag    1740
ggccagaatc agctgtacaa cgagctgaac ctgggcagaa gggaagagta cgacgtcctg    1800
gataagcgga gaggccggga ccctgagatg gcggcaagc ctcggcggaa gaaccccag    1860 gaaggcctgt ataacgaact gcagaaagac aagatggccg aggcctacag cgagatcggc    1920
atgaagggcg agcggaggcg gggcaagggc cacgacggcc tgtatcaggg cctgtccacc    1980
gccaccaagg atacctacga cgccctgcac atgcaggccc tgccccaag g              2031

<210> SEQ ID NO 3
<211> LENGTH: 2052
<212> TYPE: DNA
<213> ORGANISM: Artificial Sequence
<220> FEATURE:
<223> OTHER INFORMATION: antisense nucleotide sequence of the
      32716CAR(S228P+L235E+N297Q) construct

<400> SEQUENCE: 3
gctagcgccg ccaccatgct gctgctggtg accagcctgc tgctgtgcga gctgccccac     60
cccgcctttc tgctgatccc ccagattcag ctggtgcaga gcggcccgga actgaaaaaa    120
ccgggcgaaa ccgtgaaaat tagctgcaaa gcgagcggct atattttac caactatggc    180 atgaactggg tgaaacaggc gccgggcaaa gctttaaat ggatgggctg gattaacacc    240
tataccggcg aaagcaccta tagcgcgat tttaaaggcc gctttgcgtt tagcctggaa    300
accagcgcga gcaccgcgta tctgcatatt aacgatctga aaaacgaaga taccgcgacc    360 tattttttgcg cgcgcagcgg cggctatgat ccgatggatt attggggcca gggcaccagc    420
gtgaccgtga gcagcggcgg cggcggcagc ggcggcggcg gcagcggcgg cggcggcagc    480
gatattgtgc tgacccagag cccggcgagc ctggcggtga gcctgggcca gcgcgcgacc    540
attagctgcc gcgcgagcga aagcgtggat aactatggca cacctttat gcattggtat    600 cagcagaaac cggcccagcc gccgaaactg ctgatttatc gcgcgagcaa cctggaaagc    660
ggcattccgg cgcgctttag cggcagcggc agccgcaccg attttaccct gaccattaac    720
ccggtggaag cggatgatgt ggcgacctat tattgccagc agagcaacga agatccgccg    780 accttggcg cgggcaccaa actggaactg aaagagagca agtacggccc tcctgcccc    840 ccttgccctg ccccgagtt cgagggcgga cccagcgtgt tcctgttccc ccccaagccc    900
aaggacaccc tgatgatcag ccggaccccc gaggtgacct gcgtggtggt ggacgtgagc    960
caggaagatc ccgaggtcca gttcaattgg tacgtggacg gcgtggaagt gcacaacgcc   1020
aagaccaagc ccagagagga acagttccar agcacctacc gggtggtgtc tgtgctgacc   1080
gtgctgcacc aggactggct gaacggcaaa gaatacaagt gcaaggtgtc caacaagggc   1140
ctgcccagca gcatcgaaaa gaccatcagc aaggccaagg gccagcctcg cgagcccag   1200
```

```
gtgtacaccc tgcctccctc ccaggaagag atgaccaaga accaggtgtc cctgacctgc    1260
ctggtgaagg gcttctaccc cagcgacatc gccgtggagt gggagagcaa cggccagcct    1320
gagaacaact acaagaccac ccctcccgtg ctggacagcg acggcagctt cttcctgtac    1380
agccggctga ccgtggacaa gagccggtgg caggaaggca cgtctttag ctgcagcgtg     1440 atgcacgagg ccctgcacaa ccactacacc cagaagagcc tgagcctgtc cctgggcaag    1500
atgttctggg tgctggtggt ggtgggcggg gtgctggcct gctacagcct gctggtgaca    1560
gtggccttca tcatcttttg ggtgcggagc aagcggagca gaggcggcca cagcgactac    1620
atgaacatga ccccccagacg gcctggcccc acccggaagc actaccagcc ctacgcccca   1680
cccagggact tgccgcctac ccggtccggc ggagggcggg tgaagttcag cagaagcgcc    1740
gacgcccctg cctaccagca gggccagaat cagctgtaca cgagctgaa cctgggcaga    1800 agggaagagt acgacgtcct ggataagcgg agaggccggg accctgagat gggcggcaag    1860
cctcggcgga agaaccccca ggaaggcctg tataacgaac tgcagaaaga caagatggcc    1920
gaggcctaca gcgagatcgg catgaagggc gagcggaggc ggggcaaggg ccacgacggc    1980
ctgtatcagg gcctgtccac cgccaccaag gataccctacg acgccctgca catgcaggcc   2040 ctgccccaa gg                                                         2052

<210> SEQ ID NO 4
<211> LENGTH: 2031
<212> TYPE: DNA
<213> ORGANISM: Artificial Sequence
<220> FEATURE:
<223> OTHER INFORMATION: antisense nucleotide sequence of the
      26292CAR(S228P+L235E+N297Q) construct

<400> SEQUENCE: 4
gctagcgccg ccaccatgct gctgctggtg accagcctgc tgctgtgcga gctgcccccac    60 cccgcctttc tgctgatccc ccaggtgcag ctgcagcagc cgggcgcgga actggtgcgc    120
ccgggcgcga gcgtgaaact gagctgcaaa gcgagcggct ataccttac cagctattgg    180 atgaactggg tgaaacagcg cccggatcag ggcctggaat ggattggccg cattgatccg    240
tatgatagcg aaacccatta taaccagaaa tttaaagata agcgattct gaccgtggat     300 aaaagcagca gcaccgcgta tatgcagctg agcagcctga ccagcgaaga tagcgcggtg    360
tattattgcg cgcgcggcaa ctgggatgat tattggggcc agggcaccac cctgaccgtg    420
agcagcggcg gcggcggcag cggcggcggc ggcagcggcg gcggcggcag cgatgtgcag    480
attacccaga gcccgagcta tctggcggcg agcccgggcg aaaccattac cattaactgc    540
cgcgcgagca aaagcattag caaagatctg gcgtggtatc aggaaaaacc gggcaaaacc    600
aacaaactgc tgatttatag cggcagcacc ctgcagagcg gcattccgag ccgctttagc    660
ggcagcggca gcggcaccga ttttacccctg accattagca gcctggaacc ggaagatttt    720
gcgatgtatt attgccagca gcataacaaa tatccgtata cctttggcgg cggcaccaaa    780
ctggaaatta agagagcaa gtacggccct cctgcccccc cttgccctgc cccgagttc      840 gagggcggac ccagcgtgtt cctgttcccc ccaagcccca ggacaccct gatgatcagc     900 cggacccccg aggtgacctg cgtggtggtg gacgtgagcc aggaagatcc cgaggtccag    960
ttcaattggt acgtggacgg cgtggaagtg cacaacgcca agaccaagcc cagagaggaa    1020
cagttcaara gcacctaccg ggtggtgtct gtgctgaccg tgctgcacca ggactggctg    1080
aacggcaaag aatacaagtg caaggtgtcc aacaagggcc tgcccagcag catcgaaaag    1140
```

```
accatcagca aggccaaggg ccagcctcgc gagccccagg tgtacaccct gcctccctcc    1200
caggaagaga tgaccaagaa ccaggtgtcc ctgacctgcc tggtgaaggg cttctacccc    1260
agcgacatcg ccgtggagtg ggagagcaac ggccagcctg agaacaacta caagaccacc    1320
cctcccgtgc tggacagcga cggcagcttc ttcctgtaca gccggctgac cgtggacaag    1380
agccggtggc aggaaggcaa cgtctttagc tgcagcgtga tgcacgaggc cctgcacaac    1440
cactacaccc agaagagcct gagcctgtcc ctgggcaaga tgttctgggt gctggtggtg    1500
gtgggcgggg tgctggcctg ctacagcctg ctggtgacag tggccttcat catcttttgg    1560
gtgcggagca gcggagcag aggcggccac agcgactaca tgaacatgac ccccagacgg    1620
cctggcccca cccggaagca ctaccagccc tacgccccac ccagggactt gccgcctac    1680 cggtccggcg agggcgggt gaagttcagc agaagcgccg acgcccctgc ctaccagcag    1740
ggccagaatc agctgtacaa cgagctgaac ctgggcagaa gggaagagta cgacgtcctg    1800
gataagcgga gaggccggga ccctgagatg gcggcaagc tcggcggaa gaaccccag    1860 gaaggcctgt ataacgaact gcagaaagac aagatggccg aggcctacag cgagatcggc    1920
atgaagggcg agcggaggcg gggcaaggc cacgacggcc tgtatcaggg cctgtccacc    1980
gccaccaagg atacctacga cgccctgcac atgcaggccc tgcccccaag g             2031
```

<210> SEQ ID NO 5
<211> LENGTH: 2052
<212> TYPE: DNA
<213> ORGANISM: Artificial Sequence
<220> FEATURE:
<223> OTHER INFORMATION: sense nucleotide sequence of the
      32716CAR(S228P+L235E) construct

<400> SEQUENCE: 5

```
cgatcgcggc ggtggtacga cgacgaccac tggtcggacg acgacacgct cgacggggtg     60
gggcggaaag acgactaggg ggtctaagtc gaccacgtct cgccgggcct tgactttttt    120
ggcccgcttt ggcactttta atcgacgttt cgctcgccga tataaaaatg gttgataccg    180
tacttgaccc actttgtccg cggcccgttt tcgaaattta cctacccgac ctaattgtgg    240
atatggccgc tttcgtggat atcgcgccta aaatttccgg cgaaacgcaa atcggacctt    300
tggtcgcgct cgtggcgcat agacgtataa ttgctagact ttttgcttct atggcgctgg    360
ataaaaacgc gcgcgtcgcc gccgatacta ggctacctaa taaccccggt cccgtggtcg    420
cactggcact cgtcgccgcc gccgccgtcg ccgccgccgc cgtcgccgcc gccgccgtcg    480
ctataacacg actgggtctc gggccgctcg gaccgccact cggaccggt cgcgcgctgg    540 taatcgacgg cgccgctcgct tcgcaccta ttgataccgt tgtggaaata cgtaaccata    600 gtcgtcttttg gccggtcgg cggctttgac gactaaatag cgcgctcgtt ggaccttcg     660 ccgtaaggcc gcgcgaaatc gccgtcgccg tcggcgtggc taaaatggga ctggtaattg    720
ggccaccttc gcctactaca ccgctggata ataacgtcg tctcgttgct tctaggcggc    780
tggaaaccgc gcccgtggtt tgaccttgac tttctctcgt tcatgccggg agggacgggg    840
ggaacgggac ggggctcaa gctcccgcct gggtcgcaca aggacaaggg ggggttcggg    900
ttcctgtggg actactagtc ggcctggggg ctccactgga cgcaccacca cctgcactcg    960
gtccttctag ggctccaggt caagttaacc atgcacctgc cgcaccttca cgtgttgcgg   1020
ttctggttcg ggtctctcct tgtcaagttg tcgtggatgg cccaccacag acacgactgg   1080
cacgacgtgg tcctgaccga cttgccgttt cttatgttca cgttccacag gttgttcccg   1140
```

```
gacgggtcgt cgtagctttt ctggtagtcg ttccggttcc cggtcggagc gctcggggtc    1200
cacatgtggg acggagggag ggtccttctc tactggttct tggtccacag ggactggacg    1260
gaccacttcc cgaagatggg gtcgctgtag cggcacctca ccctctcgtt gccggtcgga    1320
ctcttgttga tgttctggtg gggagggcac gacctgtcgc tgccgtcgaa gaaggacatg    1380
tcggccgact ggcacctgtt ctcggccacc gtccttccgt tgcagaaatc gacgtcgcac    1440
tacgtgctcc gggacgtgtt ggtgatgtgg gtcttctcgg actcggacag ggacccgttc    1500
tacaagaccc acgaccacca ccacccgccc cacgaccgga cgatgtcgga cgaccactgt    1560
caccggaagt agtagaaaac ccacgcctcg ttcgcctcgt ctccgccggt gtcgctgatg    1620
tacttgtact gggggtctgc cggaccgggg tgggccttcg tgatggtcgg gatgcggggt    1680
gggtccctga acggcggat ggccaggccg cctcccgccc acttcaagtc gtcttcgcgg    1740
ctgcggggac ggatggtcgt cccggtctta gtcgacatgt tgctcgactt ggacccgtct    1800
tcccttctca tgctgcagga cctattcgcc tctccggccc tgggactcta cccgccgttc    1860
ggagccgcct tcttgggggt ccttccggac atattgcttg acgtctttct gttctaccgg    1920
ctccggatgt cgctctagcc gtacttcccg ctcgcctccg ccccgttccc ggtgctgccg    1980
gacatagtcc cggacaggtg gcggtggttc ctatggatgc tgcgggacgt gtacgtccgg    2040
gacgggggtt cc                                                        2052

<210> SEQ ID NO 6
<211> LENGTH: 2031
<212> TYPE: DNA
<213> ORGANISM: Artificial Sequence
<220> FEATURE:
<223> OTHER INFORMATION: sense nucleotide sequence of the
      26292CAR(S228P+L235E) construct

<400> SEQUENCE: 6
cgatcgcggc ggtggtacga cgacgaccac tggtcggacg acgacacgct cgacggggtg      60
gggcggaaag acgactaggg ggtccacgtc gacgtcgtcg gcccgcgcct tgaccacgcg     120
ggcccgcgct cgcactttga ctcgacgttt cgctcgccga tatggaaatg gtcgataacc     180
tacttgaccc actttgtcgc gggcctagtc ccggaccttt cctaaccggc gtaactaggc     240
atactatcgc tttgggtaat attggtcttt aaatttctat ttcgctaaga ctggcaccta     300
ttttcgtcgt cgtggcgcat atacgtcgac tcgtcggact ggtcgcttct atcgcgccac     360
ataataacgc gcgcgccgtt gaccctacta taaccccgg tcccgtggtg ggactggcac     420
tcgtcgccgc cgccgccgtc gccgccgccg ccgtcgccgc cgccgccgtc gctacacgtc     480
taatgggtct cgggctcgat agaccgccgc tcgggcccgc tttggtaatg gtaattgacg     540
gcgcgctcgt tttcgtaatc gtttctagac cgcaccatag tccttttttgg cccgttttgg     600 ttgtttgacg actaaatatc gccgtcgtgg gacgtctcgc cgtaaggctc ggcgaaatcg     660
ccgtcgccgt cgccgtggct aaaatgggac tggtaatcgt cggaccttgg ccttctaaaa     720
cgctacataa taacggtcgt cgtattgttt ataggcatat ggaaaccgcc gccgtggttt     780
gacctttaat ttctctcgtt catgccggga gggacggggg gaacgggacg ggggctcaag     840
ctcccgcctg ggtcgcacaa ggacaagggg gggttcgggt tcctgtggga ctactagtcg     900
gcctgggggc tccactggac gcaccaccac ctgcactcgg tccttctagg gctccaggtc     960
aagttaacca tgcacctgcc gcaccttcac gtgttgcgct tctggttcgg gtctctcctt    1020
gtcaagttgt cgtggatggc ccaccacaga cacgactggc acgacgtggt cctgaccgac    1080
```

```
ttgccgtttc ttatgttcac gttccacagg ttgttcccgg acgggtcgtc gtagcttttc    1140
tggtagtcgt tccggttccc ggtcggagcg ctcggggtcc acatgtggga cggagggagg    1200
gtccttctct actggttctt ggtccacagg gactggacgg accacttccc gaagatgggg    1260
tcgctgtagc ggcacctcac cctctcgttg ccggtcggac tcttgttgat gttctggtgg    1320
ggagggcacg acctgtcgct gccgtcgaag aaggacatgt cggccgactg cacctgttc     1380 tcggccaccg tccttccgtt gcagaaatcg acgtcgcact acgtgctccg ggacgtgttg    1440
gtgatgtggg tcttctcgga ctcggacagg gacccgttct acaagaccca cgaccaccac    1500
cacccgcccc acgaccggac gatgtcggac gaccactgtc accggaagta gtagaaaacc    1560
cacgcctcgt tcgcctcgtc tccgccggtg tcgctgatgt acttgtactg ggggtctgcc    1620
ggaccggggt gggccttcgt gatggtcggg atgcggggtg ggtccctgaa acggcggatg    1680
gccaggccgc ctcccgccca cttcaagtcg tcttcgcggc tgcggggacg gatggtcgtc    1740
ccggtcttag tcgacatgtt gctcgacttg gacccgtctt cccttctcat gctgcaggac    1800
ctattcgcct ctccggccct gggactctac ccgccgttcg gagccgcctt cttggggtc     1860 cttccggaca tattgcttga cgtctttctg ttctaccggc tccggatgtc gctctagccg    1920
tacttcccgc tcgcctccgc cccgttcccg gtgctgccgg acatagtccc ggacaggtgg    1980
cggtggttcc tatggatgct gcgggacgtg tacgtccggg acggggttc c              2031
```

<210> SEQ ID NO 7  
<211> LENGTH: 2052  
<212> TYPE: DNA  
<213> ORGANISM: Artificial Sequence  
<220> FEATURE:  
<223> OTHER INFORMATION: sense nucleotide sequence of the  
     32716CAR(S228P+L235E+N297Q) construct

<400> SEQUENCE: 7

```
cgatcgcggc ggtggtacga cgacgaccac tggtcggacg acgacacgct cgacggggtg     60
gggcggaaag acgactaggg ggtctaagtc gaccacgtct cgccgggcct tgacttttt     120 ggcccgcttt ggcactttta atcgacgttt cgctcgccga tataaaaatg gttgataccg    180
tacttgaccc actttgtccg cggcccgttt tcgaaattta cctacccgac ctaattgtgg    240
atatggccgc tttcgtggat atcgcgccta aaatttccgg cgaaacgcaa atcggacctt    300
tggtcgcgct cgtggcgcat agacgtataa ttgctagact ttttgcttct atggcgctgg    360
ataaaaacgc gcgcgtcgcc gccgatacta ggctacctaa taaccccggt cccgtggtcg    420
cactggcact cgtcgccgcc gccgccgtcg ccgccgccgc cgtcgccgcc gccgccgtcg    480
ctataacacg actgggtctc gggccgctcg gaccgccact cggacccggt cgcgcgctgg    540
taatcgacgg cgcgctcgct ttcgcaccta ttgataccgt tgtggaaata cgtaaccata    600
gtcgtctttg gcccgtcgg cggctttgac gactaaatag cgcgctcgtt ggaccttttcg    660 ccgtaaggcc gcgcgaaatc gccgtcgccg tcggcgtggc taaaatggga ctggtaattg    720
ggccaccttc gcctactaca ccgctggata ataacggtcg tctcgttgct tctaggcggc    780
tggaaaccgc gcccgtggtt tgaccttgac tttctctcgt tcatgccggg agggacgggg    840
ggaacgggac gggggctcaa gctcccgcct gggtcgcaca aggacaaggg ggggttcggg    900
ttcctgtggg actactagtc ggcctggggg ctccactgga cgcaccacca cctgcactcg    960
gtccttctag ggctccaggt caagttaacc atgcacctgc cgcaccttca cgtgttgcgg    1020
ttctggttcg ggtctctcct tgtcaaggty tcgtggatgg cccaccacag acacgactgg    1080
```

| | | |
|---|---|---|
| cacgacgtgg tcctgaccga cttgccgttt cttatgttca cgttccacag gttgttcccg | 1140 | |
| gacgggtcgt cgtagctttt ctggtagtcg ttccggttcc cggtcggagc gctcggggtc | 1200 | |
| cacatgtggg acggagggag ggtccttctc tactggttct tggtccacag ggactggacg | 1260 | |
| gaccacttcc cgaagatggg gtcgctgtag cggcacctca ccctctcgtt gccggtcgga | 1320 | |
| ctcttgttga tgttctggtg gggagggcac gacctgtcgc tgccgtcgaa gaaggacatg | 1380 | |
| tcggccgact ggcacctgtt ctcggccacc gtccttccgt tgcagaaatc gacgtcgcac | 1440 | |
| tacgtgctcc gggacgtgtt ggtgatgtgg gtcttctcgg actcggacag ggacccgttc | 1500 | |
| tacaagaccc acgaccacca ccacccgccc acgaccggga cgatgtcgga cgaccactgt | 1560 | |
| caccggaagt agtagaaaac ccacgcctcg ttcgcctcgt ctccgccggt gtcgctgatg | 1620 | |
| tacttgtact gggggtctgc cggaccgggg tgggccttcg tgatggtcgg gatgcggggt | 1680 | |
| gggtccctga aacggcggat ggccaggccg cctcccgccc acttcaagtc gtcttcgcgg | 1740 | |
| ctgcggggac ggatggtcgt cccggtctta gtcgacatgt tgctcgactt ggacccgtct | 1800 | |
| tcccttctca tgctgcagga cctattcgcc tctccggccc tgggactcta cccgccgttc | 1860 | |
| ggagccgcct tcttggggt ccttccggac atattgcttg acgtctttct gttctaccgg | 1920 | |
| ctccggatgt cgctctagcc gtacttcccg ctcgcctccg ccccgttccc ggtgctgccg | 1980 | |
| gacatagtcc cggacaggtg gcggtggttc ctatggatgc tgcgggacgt gtacgtccgg | 2040 | |
| gacgggggtt cc | 2052 | |

<210> SEQ ID NO 8
<211> LENGTH: 2031
<212> TYPE: DNA
<213> ORGANISM: Artificial Sequence
<220> FEATURE:
<223> OTHER INFORMATION: sense nucleotide sequence of the
      26292CAR(S228P+L235E+N297Q) construct

<400> SEQUENCE: 8

| | | |
|---|---|---|
| cgatcgcggc ggtggtacga cgacgaccac tggtcggacg acgacacgct cgacggggtg | 60 | |
| gggcggaaag acgactaggg ggtccacgtc gacgtcgtcg gcccgcgcct tgaccacgcg | 120 | |
| ggcccgcgct cgcactttga ctcgacgttt cgctcgccga tatggaaatg gtcgataacc | 180 | |
| tacttgaccc actttgtcgc gggcctagtc ccggaccttda cctaaccggc gtaactaggc | 240 | |
| atactatcgc tttgggtaat attggtcttt aaatttctat ttcgctaaga ctggcaccta | 300 | |
| ttttcgtcgt cgtggcgcat atacgtcgac tcgtcggact ggtcgcttct atcgcgccac | 360 | |
| ataataacgc gcgcgccgtt gaccctacta ataaccccgg tcccgtggtg ggactggcac | 420 | |
| tcgtcgccgc cgccgccgtc gccgccgccg ccgtcgccgc cgccgccgtc gctacacgtc | 480 | |
| taatgggtct cgggctcgat agaccgccgc tcgggcccgc tttggtaatg gtaattgacg | 540 | |
| gcgcgctcgt tttcgtaatc gtttctagac cgcaccatag tcctttttgg cccgttttgg | 600 | |
| ttgtttgacg actaaatatc gccgtcgtgg gacgtctcgc cgtaaggctc ggcgaaatcg | 660 | |
| ccgtcgccgt cgccgtggct aaaatgggac tggtaatcgt cggaccttgg ccttctaaaa | 720 | |
| cgctacataa taacggtcgt cgtattgttt ataggcatat ggaaaccgcc gccgtggttt | 780 | |
| gacctttaat ttctctcgtt catgccggga gggacggggg aacgggacg ggggctcaag | 840 | |
| ctcccgcctg ggtcgcacaa ggacaagggg gggttcgggt tcctgtggga ctactagtcg | 900 | |
| gcctgggggc tccactggac gcaccaccac ctgcactcgg tccttctagg gctccaggtc | 960 | |
| aagttaacca tgcacctgcc gcaccttcac gtgttgcggt tctggttcgg gtctctcctt | 1020 | |

```
gtcaagttyt cgtggatggc ccaccacaga cacgactggc acgacgtggt cctgaccgac    1080
ttgccgtttc ttatgttcac gttccacagg ttgttcccgg acgggtcgtc gtagcttttc    1140
tggtagtcgt tccggttccc ggtcggagcg ctcggggtcc acatgtggga cggagggagg    1200
gtccttctct actggttctt ggtccacagg gactggacgg accacttccc gaagatgggg    1260
tcgctgtagc ggcacctcac cctctcgttg ccggtcggac tcttgttgat gttctggtgg    1320
ggagggcacg acctgtcgct gccgtcgaag aaggacatgt cggccgactg cacctgttc    1380 tcggccaccg tccttccgtt gcagaaatcg acgtcgcact acgtgctccg ggacgtgttg    1440
gtgatgtggg tcttctcgga ctcggacagg gacccgttct acaagaccca cgaccaccac    1500
cacccgcccc acgaccggac gatgtcggac gaccactgtc accggaagta gtagaaaacc    1560
cacgcctcgt tcgcctcgtc tccgccggtg tcgctgatgt acttgtactg ggggtctgcc    1620
ggaccggggt gggccttcgt gatggtcggg atgcggggtg ggtccctgaa acggcggatg    1680
gccaggccgc ctcccgccca cttcaagtcg tcttcgcggc tgcggggacg gatggtcgtc    1740
ccggtcttag tcgacatgtt gctcgacttg gacccgtctt cccttctcat gctgcaggac    1800
ctattcgcct ctccggccct gggactctac ccgccgttcg gagccgcctt cttggggggtc    1860 cttccggaca tattgcttga cgtctttctg ttctaccggc tccggatgtc gctctagccg    1920
tacttcccgc tcgcctccgc cccgttcccg gtgctgccgg acatagtccc ggacaggtgg    1980
cggtggttcc tatggatgct gcgggacgtg tacgtccggg acgggggttc               2031
```

<210> SEQ ID NO 9
<211> LENGTH: 679
<212> TYPE: PRT
<213> ORGANISM: Artificial Sequence
<220> FEATURE:
<223> OTHER INFORMATION: amino acid sequence of the
      32716CAR(S228P+L235E) construct

<400> SEQUENCE: 9

```
Met Leu Leu Leu Val Thr Ser Leu Leu Leu Cys Glu Leu Pro His Pro
1               5                   10                  15

Ala Phe Leu Leu Ile Pro Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Ile Phe Thr Asn Tyr Gly Met Asn Trp Val Lys Gln Ala Pro Gly
    50                  55                  60

Lys Ser Phe Lys Trp Met Gly Trp Ile Asn Thr Tyr Thr Gly Glu Ser
65                  70                  75                  80

Thr Tyr Ser Ala Asp Phe Lys Gly Arg Phe Ala Phe Ser Leu Glu Thr
                85                  90                  95

Ser Ala Ser Thr Ala Tyr Leu His Ile Asn Asp Leu Lys Asn Glu Asp
            100                 105                 110

Thr Ala Thr Tyr Phe Cys Ala Arg Ser Gly Gly Tyr Asp Pro Met Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Gly Ser Asp Ile Val Leu Thr
145                 150                 155                 160

Gln Ser Pro Ala Ser Leu Ala Val Ser Leu Gly Gln Arg Ala Thr Ile
                165                 170                 175
```

-continued

```
Ser Cys Arg Ala Ser Glu Ser Val Asp Asn Tyr Gly Asn Thr Phe Met
            180                 185                 190

His Trp Tyr Gln Gln Lys Pro Gly Gln Pro Pro Lys Leu Leu Ile Tyr
        195                 200                 205

Arg Ala Ser Asn Leu Glu Ser Gly Ile Pro Ala Arg Phe Ser Gly Ser
    210                 215                 220

Gly Ser Arg Thr Asp Phe Thr Leu Thr Ile Asn Pro Val Glu Ala Asp
225                 230                 235                 240

Asp Val Ala Thr Tyr Tyr Cys Gln Gln Ser Asn Glu Asp Pro Pro Thr
                245                 250                 255

Phe Gly Ala Gly Thr Lys Leu Glu Leu Lys Glu Ser Lys Tyr Gly Pro
            260                 265                 270

Pro Cys Pro Pro Cys Pro Ala Pro Glu Phe Glu Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Gly Leu Pro Ser Ser Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Arg Leu Thr Val Asp Lys Ser Arg
    450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys Met
                485                 490                 495

Phe Trp Val Leu Val Val Val Gly Gly Val Leu Ala Cys Tyr Ser Leu
            500                 505                 510

Leu Val Thr Val Ala Phe Ile Ile Phe Trp Val Arg Ser Lys Arg Ser
        515                 520                 525

Arg Gly Gly His Ser Asp Tyr Met Asn Met Thr Pro Arg Arg Pro Gly
    530                 535                 540

Pro Thr Arg Lys His Tyr Gln Pro Tyr Ala Pro Pro Arg Asp Phe Ala
545                 550                 555                 560

Ala Tyr Arg Ser Gly Gly Gly Arg Val Lys Phe Ser Arg Ser Ala Asp
                565                 570                 575

Ala Pro Ala Tyr Gln Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
```

```
                595                 600                 605
Asp Pro Glu Met Gly Gly Lys Pro Arg Arg Lys Asn Pro Gln Glu Gly
    610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
            660                 665                 670

Met Gln Ala Leu Pro Pro Arg
        675

<210> SEQ ID NO 10
<211> LENGTH: 672
<212> TYPE: PRT
<213> ORGANISM: Artificial Sequence
<220> FEATURE:
<223> OTHER INFORMATION: amino acid sequence of the
      26292CAR(S228P+L235E) construct

<400> SEQUENCE: 10

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Pro Gly Ala Glu
            20                  25                  30

Leu Val Arg Pro Gly Ala Ser Val Lys Leu Ser Cys Lys Ala Ser Gly
        35                  40                  45

Tyr Thr Phe Thr Ser Tyr Trp Met Asn Trp Val Lys Gln Arg Pro Asp
    50                  55                  60

Gln Gly Leu Glu Trp Ile Gly Arg Ile Asp Pro Tyr Asp Ser Glu Thr
65                  70                  75                  80

His Tyr Asn Gln Lys Phe Lys Asp Lys Ala Ile Leu Thr Val Asp Lys
                85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Gly Asn Trp Asp Asp Tyr Trp Gly
        115                 120                 125

Gln Gly Thr Thr Leu Thr Val Ser Ser Gly Gly Gly Ser Gly Gly
130                 135                 140

Gly Gly Ser Gly Gly Gly Ser Asp Val Gln Ile Thr Gln Ser Pro
145                 150                 155                 160

Ser Tyr Leu Ala Ala Ser Pro Gly Glu Thr Ile Thr Ile Asn Cys Arg
            165                 170                 175

Ala Ser Lys Ser Ile Ser Lys Asp Leu Ala Trp Tyr Gln Glu Lys Pro
        180                 185                 190

Gly Lys Thr Asn Lys Leu Leu Ile Tyr Ser Gly Ser Thr Leu Gln Ser
    195                 200                 205

Gly Ile Pro Ser Arg Phe Ser Gly Ser Gly Ser Gly Thr Asp Phe Thr
    210                 215                 220

Leu Thr Ile Ser Ser Leu Glu Pro Glu Asp Phe Ala Met Tyr Tyr Cys
225                 230                 235                 240

Gln Gln His Asn Lys Tyr Pro Tyr Thr Phe Gly Gly Gly Thr Lys Leu
                245                 250                 255

Glu Ile Lys Glu Ser Lys Tyr Gly Pro Pro Cys Pro Pro Cys Pro Ala
            260                 265                 270
```

```
Pro Glu Phe Glu Gly Gly Pro Ser Val Phe Leu Phe Pro Lys Pro
            275                 280                 285

Lys Asp Thr Leu Met Ile Ser Arg Thr Pro Glu Val Thr Cys Val Val
290                 295                 300

Val Asp Val Ser Gln Glu Asp Pro Glu Val Gln Phe Asn Trp Tyr Val
305                 310                 315                 320

Asp Gly Val Glu Val His Asn Ala Lys Thr Lys Pro Arg Glu Glu Gln
                325                 330                 335

Phe Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Gly
        355                 360                 365

Leu Pro Ser Ser Ile Glu Lys Thr Ile Ser Lys Ala Lys Gly Gln Pro
    370                 375                 380

Arg Glu Pro Gln Val Tyr Thr Leu Pro Pro Ser Gln Glu Glu Met Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Arg Leu Thr Val Asp Lys Ser Arg Trp Gln Glu Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Leu Gly Lys Met Phe Trp Val Leu Val Val Val
                485                 490                 495

Gly Gly Val Leu Ala Cys Tyr Ser Leu Leu Val Thr Val Ala Phe Ile
            500                 505                 510

Ile Phe Trp Val Arg Ser Lys Arg Ser Arg Gly Gly His Ser Asp Tyr
        515                 520                 525

Met Asn Met Thr Pro Arg Arg Pro Gly Pro Thr Arg Lys His Tyr Gln
    530                 535                 540

Pro Tyr Ala Pro Pro Arg Asp Phe Ala Ala Tyr Arg Ser Gly Gly Gly
545                 550                 555                 560

Arg Val Lys Phe Ser Arg Ser Ala Asp Ala Pro Ala Tyr Gln Gln Gly
                565                 570                 575

Gln Asn Gln Leu Tyr Asn Glu Leu Asn Leu Gly Arg Arg Glu Glu Tyr
            580                 585                 590

Asp Val Leu Asp Lys Arg Arg Gly Arg Asp Pro Glu Met Gly Gly Lys
        595                 600                 605

Pro Arg Arg Lys Asn Pro Gln Glu Gly Leu Tyr Asn Glu Leu Gln Lys
    610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
            660                 665                 670

<210> SEQ ID NO 11
<211> LENGTH: 679
<212> TYPE: PRT
```

<213> ORGANISM: Artificial Sequence
<220> FEATURE:
<223> OTHER INFORMATION: amino acid sequence of the
      32716CAR(S228P+L235E+N297Q) construct

<400> SEQUENCE: 11

Met Leu Leu Leu Val Thr Ser Leu Leu Leu Cys Glu Leu Pro His Pro
1               5                   10                  15

Ala Phe Leu Leu Ile Pro Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Ile Phe Thr Asn Tyr Gly Met Asn Trp Val Lys Gln Ala Pro Gly
    50                  55                  60

Lys Ser Phe Lys Trp Met Gly Trp Ile Asn Thr Tyr Thr Gly Glu Ser
65                  70                  75                  80

Thr Tyr Ser Ala Asp Phe Lys Gly Arg Phe Ala Phe Ser Leu Glu Thr
                85                  90                  95

Ser Ala Ser Thr Ala Tyr Leu His Ile Asn Asp Leu Lys Asn Glu Asp
            100                 105                 110

Thr Ala Thr Tyr Phe Cys Ala Arg Ser Gly Tyr Asp Pro Met Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Ser Asp Ile Val Leu Thr
145                 150                 155                 160

Gln Ser Pro Ala Ser Leu Ala Val Ser Leu Gly Gln Arg Ala Thr Ile
                165                 170                 175

Ser Cys Arg Ala Ser Glu Ser Val Asp Asn Tyr Gly Asn Thr Phe Met
            180                 185                 190

His Trp Tyr Gln Gln Lys Pro Gly Gln Pro Pro Lys Leu Leu Ile Tyr
        195                 200                 205

Arg Ala Ser Asn Leu Glu Ser Gly Ile Pro Ala Arg Phe Ser Gly Ser
    210                 215                 220

Gly Ser Arg Thr Asp Phe Thr Leu Thr Ile Asn Pro Val Glu Ala Asp
225                 230                 235                 240

Asp Val Ala Thr Tyr Tyr Cys Gln Gln Ser Asn Glu Asp Pro Pro Thr
                245                 250                 255

Phe Gly Ala Gly Thr Lys Leu Glu Leu Lys Glu Ser Lys Tyr Gly Pro
            260                 265                 270

Pro Cys Pro Pro Cys Pro Ala Pro Glu Phe Glu Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Gln Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Gly Leu Pro Ser Ser Ile Glu Lys Thr Ile
    370                 375                 380

```
Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Arg Leu Thr Val Asp Lys Ser Arg
    450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys Met
                485                 490                 495

Phe Trp Val Leu Val Val Val Gly Gly Val Leu Ala Cys Tyr Ser Leu
            500                 505                 510

Leu Val Thr Val Ala Phe Ile Ile Phe Trp Val Arg Ser Lys Arg Ser
        515                 520                 525

Arg Gly Gly His Ser Asp Tyr Met Asn Met Thr Pro Arg Arg Pro Gly
    530                 535                 540

Pro Thr Arg Lys His Tyr Gln Pro Tyr Ala Pro Pro Arg Asp Phe Ala
545                 550                 555                 560

Ala Tyr Arg Ser Gly Gly Gly Arg Val Lys Phe Ser Arg Ser Ala Asp
                565                 570                 575

Ala Pro Ala Tyr Gln Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
        595                 600                 605

Asp Pro Glu Met Gly Gly Lys Pro Arg Arg Lys Asn Pro Gln Glu Gly
    610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
            660                 665                 670

Met Gln Ala Leu Pro Pro Arg
        675

<210> SEQ ID NO 12
<211> LENGTH: 672
<212> TYPE: PRT
<213> ORGANISM: Artificial Sequence
<220> FEATURE:
<223> OTHER INFORMATION: amino acid sequence of the
      26292CAR(S228P+L235E+N297Q) construct

<400> SEQUENCE: 12

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Pro Gly Ala Glu
            20                  25                  30

Leu Val Arg Pro Gly Ala Ser Val Lys Leu Ser Cys Lys Ala Ser Gly
        35                  40                  45

Tyr Thr Phe Thr Ser Tyr Trp Met Asn Trp Val Lys Gln Arg Pro Asp
    50                  55                  60
```

```
Gln Gly Leu Glu Trp Ile Gly Arg Ile Asp Pro Tyr Asp Ser Glu Thr
 65                  70                  75                  80

His Tyr Asn Gln Lys Phe Lys Asp Lys Ala Ile Leu Thr Val Asp Lys
                 85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Gly Asn Trp Asp Asp Tyr Trp Gly
        115                 120                 125

Gln Gly Thr Thr Leu Thr Val Ser Ser Gly Gly Gly Ser Gly Gly
130                 135                 140

Gly Gly Ser Gly Gly Gly Ser Asp Val Gln Ile Thr Gln Ser Pro
145                 150                 155                 160

Ser Tyr Leu Ala Ala Ser Pro Gly Glu Thr Ile Thr Ile Asn Cys Arg
            165                 170                 175

Ala Ser Lys Ser Ile Ser Lys Asp Leu Ala Trp Tyr Gln Glu Lys Pro
        180                 185                 190

Gly Lys Thr Asn Lys Leu Leu Ile Tyr Ser Gly Ser Thr Leu Gln Ser
            195                 200                 205

Gly Ile Pro Ser Arg Phe Ser Gly Ser Gly Ser Gly Thr Asp Phe Thr
210                 215                 220

Leu Thr Ile Ser Ser Leu Glu Pro Glu Asp Phe Ala Met Tyr Tyr Cys
225                 230                 235                 240

Gln Gln His Asn Lys Tyr Pro Tyr Thr Phe Gly Gly Gly Thr Lys Leu
            245                 250                 255

Glu Ile Lys Glu Ser Lys Tyr Gly Pro Pro Cys Pro Pro Cys Pro Ala
        260                 265                 270

Pro Glu Phe Glu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
        290                 295                 300

Val Asp Val Ser Gln Glu Asp Pro Glu Val Gln Phe Asn Trp Tyr Val
305                 310                 315                 320

Asp Gly Val Glu Val His Asn Ala Lys Thr Lys Pro Arg Glu Glu Gln
            325                 330                 335

Phe Gln Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Gly
        355                 360                 365

Leu Pro Ser Ser Ile Glu Lys Thr Ile Ser Lys Ala Lys Gly Gln Pro
        370                 375                 380

Arg Glu Pro Gln Val Tyr Thr Leu Pro Pro Ser Gln Glu Glu Met Thr
385                 390                 395                 400

Lys Asn Gln Val Ser Leu Thr Cys Leu Val Lys Gly Phe Tyr Pro Ser
            405                 410                 415

Asp Ile Ala Val Glu Trp Glu Ser Asn Gly Gln Pro Glu Asn Asn Tyr
        420                 425                 430

Lys Thr Thr Pro Pro Val Leu Asp Ser Asp Gly Ser Phe Phe Leu Tyr
            435                 440                 445

Ser Arg Leu Thr Val Asp Lys Ser Arg Trp Gln Glu Gly Asn Val Phe
        450                 455                 460

Ser Cys Ser Val Met His Glu Ala Leu His Asn His Tyr Thr Gln Lys
465                 470                 475                 480
```

-continued

```
Ser Leu Ser Leu Ser Leu Gly Lys Met Phe Trp Val Leu Val Val Val
                485                 490                 495

Gly Gly Val Leu Ala Cys Tyr Ser Leu Leu Val Thr Val Ala Phe Ile
            500                 505                 510

Ile Phe Trp Val Arg Ser Lys Arg Ser Arg Gly Gly His Ser Asp Tyr
        515                 520                 525

Met Asn Met Thr Pro Arg Arg Pro Gly Pro Thr Arg Lys His Tyr Gln
    530                 535                 540

Pro Tyr Ala Pro Pro Arg Asp Phe Ala Ala Tyr Arg Ser Gly Gly Gly
545                 550                 555                 560

Arg Val Lys Phe Ser Arg Ser Ala Asp Ala Pro Ala Tyr Gln Gln Gly
                565                 570                 575

Gln Asn Gln Leu Tyr Asn Glu Leu Asn Leu Gly Arg Arg Glu Glu Tyr
            580                 585                 590

Asp Val Leu Asp Lys Arg Arg Gly Arg Asp Pro Glu Met Gly Gly Lys
        595                 600                 605

Pro Arg Arg Lys Asn Pro Gln Glu Gly Leu Tyr Asn Glu Leu Gln Lys
    610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
            660                 665                 670

<210> SEQ ID NO 13
<211> LENGTH: 229
<212> TYPE: PRT
<213> ORGANISM: Homo sapiens

<400> SEQUENCE: 13

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190
```

```
Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

UNITED STATES PATENT AND TRADEMARK OFFICE
CERTIFICATE OF CORRECTION

| | | |
|---|---|---|
| PATENT NO. | : 11,918,606 B2 | Page 1 of 1 |
| APPLICATION NO. | : 16/859590 | |
| DATED | : March 5, 2024 | |
| INVENTOR(S) | : Stephen J. Forman, Armen Mardiros and Christine E. Brown | |

It is certified that error appears in the above-identified patent and that said Letters Patent is hereby corrected as shown below:

In the Claims

Column 60, Line 24 (approx.), Claim 13, delete "wherein the wherein the" and insert -- wherein the --

Column 60, Line 29 (approx.), Claim 15, delete "wherein the wherein the" and insert -- wherein the --

Column 60, Line 34 (approx.), Claim 17, delete "wherein the wherein the" and insert -- wherein the --

Signed and Sealed this
Seventeenth Day of December, 2024

Derrick Brent
*Acting Director of the United States Patent and Trademark Office*